US011654193B2

(12) United States Patent
Kipps et al.

(10) Patent No.: US 11,654,193 B2
(45) Date of Patent: *May 23, 2023

(54) CANCER TREATMENT COMBINATIONS

(71) Applicant: The Regents of the University of California, Oakland, CA (US)

(72) Inventors: Thomas J. Kipps, San Diego, CA (US); Liguang Chen, San Diego, CA (US); Bing Cui, San Diego, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 293 days.

This patent is subject to a terminal disclaimer.

(21) Appl. No.: 16/870,803

(22) Filed: May 8, 2020

(65) Prior Publication Data

US 2021/0038716 A1 Feb. 11, 2021

Related U.S. Application Data

(63) Continuation of application No. 15/634,802, filed on Jun. 27, 2017, now Pat. No. 10,688,181.

(60) Provisional application No. 62/355,171, filed on Jun. 27, 2016.

(51) Int. Cl.
| | |
|---|---|
| A61K 39/395 | (2006.01) |
| C07K 16/28 | (2006.01) |
| A61K 31/519 | (2006.01) |
| A61K 9/00 | (2006.01) |
| A61K 45/06 | (2006.01) |
| A61K 39/00 | (2006.01) |

(52) U.S. Cl.
CPC ...... *A61K 39/39558* (2013.01); *A61K 9/0019* (2013.01); *A61K 31/519* (2013.01); *A61K 45/06* (2013.01); *C07K 16/2803* (2013.01); *A61K 2039/505* (2013.01); *C07K 2317/24* (2013.01); *C07K 2317/56* (2013.01); *C07K 2317/73* (2013.01); *C07K 2317/76* (2013.01)

(58) Field of Classification Search
CPC .......... A61K 2039/505; A61K 2300/00; A61K 45/06
See application file for complete search history.

(56) References Cited

U.S. PATENT DOCUMENTS

| | | | |
|---|---|---|---|
| 5,219,837 A | 6/1993 | Cohen et al. | |
| 5,843,749 A | 12/1998 | Maisonpierre et al. | |
| 5,855,885 A | 1/1999 | Smith et al. | |
| 5,858,725 A | 1/1999 | Crowe et al. | |
| 5,985,279 A | 11/1999 | Waldmann et al. | |
| 6,001,575 A | 12/1999 | Huganir et al. | |
| 6,133,426 A | 10/2000 | Gonzalez et al. | |
| 6,303,341 B1 | 10/2001 | Hiatt et al. | |
| 6,586,251 B2 | 7/2003 | Economides et al. | |
| 6,596,541 B2 | 7/2003 | Murphy et al. | |
| 6,605,709 B1 | 8/2003 | Breton | |
| 6,663,863 B2 | 12/2003 | Horvath et al. | |
| 6,677,436 B1 | 1/2004 | Sato et al. | |
| 6,703,018 B2 | 3/2004 | Jardieu et al. | |
| 6,919,183 B2 | 7/2005 | Fandl et al. | |
| 7,105,348 B2 | 9/2006 | Murphy et al. | |
| 7,138,501 B2 | 11/2006 | Ruben et al. | |
| 7,193,069 B2 | 3/2007 | Isogai et al. | |
| 7,214,786 B2 | 5/2007 | Kovalic et al. | |
| 7,223,393 B2 | 5/2007 | Landolfi et al. | |
| 7,235,380 B1 | 6/2007 | Joliffe et al. | |
| 7,244,430 B2 | 7/2007 | Throsby et al. | |
| 7,314,974 B2 | 1/2008 | Cao et al. | |
| 7,323,553 B2 | 1/2008 | Fahrner et al. | |
| 7,332,582 B2 | 2/2008 | Hardy et al. | |
| 7,381,801 B2 | 6/2008 | Renner et al. | |
| 7,396,530 B2 | 7/2008 | Goffe | |
| 7,427,399 B2 | 9/2008 | Jakobovits et al. | |
| 7,429,382 B2 | 9/2008 | Albone et al. | |
| 7,435,549 B1 | 10/2008 | Kufer et al. | |
| 7,435,553 B2 | 10/2008 | Fandl et al. | |
| 7,473,423 B2 | 1/2009 | Rodriguez et al. | |
| 7,504,086 B2 | 3/2009 | Shiotsuka et al. | |
| 7,524,498 B2 | 4/2009 | Hardy et al. | |
| 7,534,604 B2 | 5/2009 | Fandl et al. | |
| 7,544,790 B2 | 6/2009 | Joliffe et al. | |
| 7,569,389 B2 | 8/2009 | Feldmann et al. | |
| 7,604,800 B2 | 10/2009 | Lin et al. | |

(Continued)

FOREIGN PATENT DOCUMENTS

| | | |
|---|---|---|
| CA | 2 705 923 A1 | 5/2009 |
| CA | 2 734 645 A1 | 2/2010 |

(Continued)

OTHER PUBLICATIONS

Kokhaei, P. et al. (2016, e-published Sep. 11, 2015). "Ibrutinib—A double-edge sword in cancer and autoimmune disorders," *Journal of Drug Targeting* 24(5):373-385.

(Continued)

*Primary Examiner* — Karen A. Canella

(74) *Attorney, Agent, or Firm* — Mintz, Levin, Cohn, Ferris, Glovsky and Popeo, P.C.

(57) ABSTRACT

There are provided, inter alia, compositions and methods for treatment of cancer. The methods include administering to a subject in need a therapeutically effective amount of a Bruton's tyrosine kinase (BTK) antagonist and a ROR-1 antagonist. Further provided are pharmaceutical compositions including a BTK antagonist, ROR-1 antagonist and a pharmaceutically acceptable excipient. In embodiments, the BTK antagonist is ibrutinib and the ROR-1 antagonist is cirmtuzumab.

13 Claims, 40 Drawing Sheets

Specification includes a Sequence Listing.

(56) References Cited

U.S. PATENT DOCUMENTS

| | | |
|---|---|---|
| 7,605,235 B2 | 10/2009 | Anderson et al. |
| 7,608,453 B2 | 10/2009 | Cattaneo et al. |
| 7,612,179 B2 | 11/2009 | Nordstedt et al. |
| 7,619,069 B2 | 11/2009 | Davies et al. |
| 7,625,561 B2 | 12/2009 | Finnern et al. |
| 7,700,098 B2 | 4/2010 | Ferlin et al. |
| 7,718,774 B2 | 5/2010 | Mather et al. |
| 7,736,647 B2 | 6/2010 | Boumsell et al. |
| 7,750,124 B2 | 7/2010 | Gurney et al. |
| 7,763,249 B2 | 7/2010 | Sugimura et al. |
| 7,807,160 B2 | 10/2010 | Presta et al. |
| 7,807,166 B2 | 10/2010 | Rodriguez et al. |
| 7,867,493 B2 | 1/2011 | Damiano et al. |
| 7,868,141 B2 | 1/2011 | Endl et al. |
| 7,910,100 B2 | 3/2011 | Stuhmer et al. |
| 7,919,089 B2 | 4/2011 | Kufer et al. |
| 7,960,515 B2 | 6/2011 | Min et al. |
| 7,968,687 B2 | 6/2011 | McDonagh et al. |
| 7,981,416 B2 | 7/2011 | Hardy et al. |
| 8,008,445 B2 | 8/2011 | Devy et al. |
| 8,043,839 B2 | 10/2011 | Weiner et al. |
| 8,062,635 B2 | 11/2011 | Hattori et al. |
| 8,067,671 B2 | 11/2011 | Boukharov et al. |
| 8,071,730 B2 | 12/2011 | Goetsch et al. |
| 8,075,885 B2 | 12/2011 | Bebbington et al. |
| 8,076,459 B2 | 12/2011 | Hofmeister et al. |
| 8,084,584 B2 | 12/2011 | Sugo et al. |
| 8,101,179 B2 | 1/2012 | Numazaki et al. |
| 8,101,722 B2 | 1/2012 | Kufer et al. |
| 8,119,130 B2 | 2/2012 | Barry et al. |
| 8,124,093 B2 | 2/2012 | Lanzavecchia et al. |
| 8,147,836 B2 | 4/2012 | Wood et al. |
| 8,163,279 B2 | 4/2012 | Bergstein |
| 8,168,757 B2 | 5/2012 | Finnefrock et al. |
| 8,183,346 B2 | 5/2012 | Leung et al. |
| 8,187,601 B2 | 5/2012 | Weng et al. |
| 8,188,234 B2 | 5/2012 | Condra et al. |
| 8,212,008 B2 | 7/2012 | Presta et al. |
| 8,212,009 B2 | 7/2012 | Kipps et al. |
| 8,258,266 B2 | 9/2012 | Deshpande et al. |
| 8,298,532 B2 | 10/2012 | Fandl et al. |
| 8,298,545 B2 | 10/2012 | Payne et al. |
| 8,298,769 B2 | 10/2012 | Smith et al. |
| 8,299,318 B2 | 10/2012 | Brover et al. |
| 8,309,693 B2 | 11/2012 | Smith et al. |
| 8,313,747 B2 | 11/2012 | Allison et al. |
| 8,314,213 B2 | 11/2012 | Bernett et al. |
| 8,318,163 B2 | 11/2012 | Appleton et al. |
| 8,323,646 B2 | 12/2012 | Swanson et al. |
| 8,343,764 B2 | 1/2013 | Abad et al. |
| 8,362,325 B2 | 1/2013 | Troukhan et al. |
| 8,410,250 B2 | 4/2013 | Ashkenazi et al. |
| 8,410,251 B2 | 4/2013 | Matsuura et al. |
| 8,414,893 B2 | 4/2013 | Biere-Citron et al. |
| 8,420,795 B2 | 4/2013 | Rodriguez et al. |
| 8,444,981 B2 | 5/2013 | Hsu et al. |
| 8,455,719 B2 | 6/2013 | Frankard et al. |
| 8,468,130 B2 | 6/2013 | Bhandari et al. |
| 8,470,324 B2 | 6/2013 | Fandl et al. |
| 8,481,692 B2 | 7/2013 | Sidhu et al. |
| 8,524,869 B2 | 9/2013 | Smith et al. |
| 8,545,847 B2 | 10/2013 | Okamoto et al. |
| 8,546,546 B2 | 10/2013 | Nakano |
| 8,551,715 B2 | 10/2013 | Gurney et al. |
| 8,568,719 B2 | 10/2013 | Williamson et al. |
| 8,575,317 B2 | 11/2013 | Kuramochi et al. |
| 8,580,257 B2 | 11/2013 | Tremblay et al. |
| 8,580,714 B2 | 11/2013 | Almagro et al. |
| 8,580,928 B2 | 11/2013 | Dennis |
| 8,586,006 B2 | 11/2013 | Hood et al. |
| 8,592,559 B2 | 11/2013 | Wakita et al. |
| 8,597,898 B2 | 12/2013 | Fandl et al. |
| 8,603,474 B2 | 12/2013 | Ritter et al. |
| 8,609,095 B2 | 12/2013 | Pedersen et al. |
| 8,632,774 B2 | 1/2014 | Misher et al. |
| 8,637,026 B2 | 1/2014 | Zauderer et al. |
| 8,637,036 B2 | 1/2014 | Mascola et al. |
| 8,673,307 B1 | 3/2014 | Nussenzweig et al. |
| 8,710,022 B2 | 4/2014 | Takahashi et al. |
| 8,715,941 B2 | 5/2014 | Abo et al. |
| 8,716,195 B2 | 5/2014 | Cappuccilli et al. |
| 8,722,046 B2 | 5/2014 | Amemiya et al. |
| 8,747,847 B2 | 6/2014 | Rotem-Yehudar et al. |
| 8,759,105 B2 | 6/2014 | Economides et al. |
| 8,790,649 B2 | 7/2014 | Setiady et al. |
| 8,816,055 B2 | 8/2014 | Sexton et al. |
| 8,846,402 B2 | 9/2014 | Economides et al. |
| 8,858,941 B2 | 10/2014 | Gurney et al. |
| 8,865,430 B2 | 10/2014 | Fandl et al. |
| 8,895,010 B2 | 11/2014 | Nadler et al. |
| 8,906,635 B2 | 12/2014 | Jin et al. |
| 8,916,160 B2 | 12/2014 | Grandea, III et al. |
| 8,926,976 B2 | 1/2015 | Corbin et al. |
| 8,927,233 B2 | 1/2015 | Fandl et al. |
| 8,937,159 B2 | 1/2015 | Harding et al. |
| 8,968,736 B2 | 3/2015 | Croll et al. |
| 8,986,972 B2 | 3/2015 | Stull et al. |
| 8,992,910 B2 | 3/2015 | Bergstein |
| 9,012,723 B2 | 4/2015 | Guo et al. |
| 9,029,508 B2 | 5/2015 | Ghayur et al. |
| 9,029,636 B2 | 5/2015 | Wu et al. |
| 9,056,910 B2 | 6/2015 | Chen et al. |
| 9,062,115 B2 | 6/2015 | Oestergaard et al. |
| 9,067,986 B2 | 6/2015 | Gurney et al. |
| 9,073,990 B2 | 7/2015 | Paas et al. |
| 9,073,991 B2 | 7/2015 | Allan et al. |
| 9,074,006 B2 | 7/2015 | Himanen et al. |
| 9,090,674 B2 | 7/2015 | Reddy et al. |
| 9,090,679 B2 | 7/2015 | Yokoseki et al. |
| 9,102,724 B2 | 8/2015 | Cummings et al. |
| 9,150,647 B2 | 10/2015 | Mellstedt et al. |
| 9,163,258 B2 | 10/2015 | Riddell et al. |
| 9,173,962 B2 | 11/2015 | Beau-Larvor et al. |
| 9,217,040 B2 | 12/2015 | Kipps et al. |
| 9,228,023 B2 | 1/2016 | Rohlff et al. |
| 9,228,208 B2 | 1/2016 | Frendewey et al. |
| 9,260,512 B2 | 2/2016 | Rodriguez et al. |
| 9,266,952 B2 | 2/2016 | Teige |
| 9,316,646 B2 | 4/2016 | Rader et al. |
| 9,758,591 B2 | 9/2017 | Kipps et al. |
| 10,344,096 B2 | 7/2019 | Kipps et al. |
| 10,688,181 B2 | 6/2020 | Kipps et al. |
| 2006/0030015 A1 | 2/2006 | Uda et al. |
| 2008/0318212 A1 | 12/2008 | Wilson et al. |
| 2009/0137416 A1 | 5/2009 | Fandl et al. |
| 2009/0203886 A1 | 8/2009 | Uchiyama et al. |
| 2010/0129817 A1 | 5/2010 | Wei et al. |
| 2011/0104053 A1 | 5/2011 | Rodriguez et al. |
| 2011/0165650 A1 | 7/2011 | Fandl et al. |
| 2012/0058051 A1 | 3/2012 | Rader et al. |
| 2012/0282177 A1 | 11/2012 | Rohlff et al. |
| 2013/0039925 A1 | 2/2013 | Bansal |
| 2013/0131139 A1 | 5/2013 | Tyner et al. |
| 2013/0251642 A1 | 9/2013 | Rader et al. |
| 2014/0065167 A1 | 3/2014 | Rodriguez et al. |
| 2014/0072979 A1 | 3/2014 | Fandl et al. |
| 2014/0072980 A1 | 3/2014 | Fandl et al. |
| 2014/0134719 A1 | 5/2014 | Despande et al. |
| 2015/0232569 A1 | 8/2015 | Kipps et al. |
| 2018/0066063 A1 | 3/2018 | Kipps et al. |

FOREIGN PATENT DOCUMENTS

| | | |
|---|---|---|
| CA | 2 851 941 A1 | 5/2013 |
| CA | 2 854 126 A1 | 5/2013 |
| CN | 103792364 A | 5/2014 |
| EP | 2 617 320 A1 | 7/2013 |
| JP | 2006-311857 A | 11/2006 |
| KR | 2014-0008308 A | 1/2014 |
| WO | WO-2003/018632 A2 | 3/2003 |
| WO | WO-2003/018632 A3 | 3/2003 |
| WO | WO-2004/009805 A1 | 1/2004 |
| WO | WO-2006/106959 A1 | 10/2006 |
| WO | WO-2007/102230 A1 | 9/2007 |

(56) References Cited

FOREIGN PATENT DOCUMENTS

| | | |
|---|---|---|
| WO | WO-2007/146957 A2 | 12/2007 |
| WO | WO-2007/146957 A3 | 12/2007 |
| WO | WO-2008/062063 A1 | 5/2008 |
| WO | WO-2008/076868 A2 | 6/2008 |
| WO | WO-2008/076868 A3 | 6/2008 |
| WO | WO-2008/103849 A2 | 8/2008 |
| WO | WO-2008/103849 A3 | 8/2008 |
| WO | WO-2008/103849 A4 | 8/2008 |
| WO | WO-2009/031230 A1 | 3/2009 |
| WO | WO-2009/101611 A1 | 8/2009 |
| WO | WO-2009/154283 A1 | 12/2009 |
| WO | WO-2010/008069 A1 | 1/2010 |
| WO | WO-2010/124188 A1 | 10/2010 |
| WO | WO-2011/054007 A1 | 5/2011 |
| WO | WO-2011057788 A1 | 5/2011 |
| WO | WO-2011/079902 A2 | 7/2011 |
| WO | WO-2011/079902 A3 | 7/2011 |
| WO | WO-2011/107957 A1 | 9/2011 |
| WO | WO-2011/131407 A1 | 10/2011 |
| WO | WO-2012/008494 A1 | 1/2012 |
| WO | WO-2012/069550 A1 | 5/2012 |
| WO | WO-2012/075158 A1 | 6/2012 |
| WO | WO-2012/076066 A1 | 6/2012 |
| WO | WO-2012/076727 A1 | 6/2012 |
| WO | WO-2012/097313 A2 | 7/2012 |
| WO | WO-2012/097313 A3 | 7/2012 |
| WO | WO-2012/156018 A1 | 11/2012 |
| WO | WO-2013/019730 A1 | 2/2013 |
| WO | WO-2013/059738 A2 | 4/2013 |
| WO | WO-2013/125636 A1 | 8/2013 |
| WO | WO-2013/125654 A1 | 8/2013 |
| WO | WO-2013/147153 A1 | 10/2013 |
| WO | WO-2013/147169 A1 | 10/2013 |
| WO | WO-2013/147176 A1 | 10/2013 |
| WO | WO-2013/152020 A1 | 10/2013 |
| WO | WO-2013/172961 A1 | 11/2013 |
| WO | WO-2013/174264 A1 | 11/2013 |
| WO | WO-2014/031174 A1 | 2/2014 |
| WO | WO-2014/130879 A2 | 8/2014 |
| WO | WO-2014/130879 A3 | 8/2014 |
| WO | WO-2014/167022 A1 | 10/2014 |
| WO | WO-2014/174111 A1 | 10/2014 |
| WO | WO-2014/189973 A2 | 11/2014 |
| WO | WO-2014/189973 A3 | 11/2014 |
| WO | WO-2015/014376 A1 | 2/2015 |
| WO | WO-2015/031693 A1 | 3/2015 |
| WO | WO-2015/069794 A2 | 5/2015 |
| WO | WO-2015/069794 A3 | 5/2015 |
| WO | WO-2015/069794 A9 | 5/2015 |
| WO | WO-2015/089344 A1 | 6/2015 |
| WO | WO-2015/095392 A1 | 6/2015 |
| WO | WO-2015/099838 A2 | 7/2015 |
| WO | WO-2015/099838 A3 | 7/2015 |
| WO | WO-2015/116653 A1 | 8/2015 |
| WO | WO-2015/127407 A1 | 8/2015 |
| WO | WO-2015/150327 A1 | 10/2015 |
| WO | WO-2015/157252 A1 | 10/2015 |
| WO | WO-2015/157252 A8 | 10/2015 |
| WO | WO-2015/162293 A1 | 10/2015 |
| WO | WO-2018/005519 A2 | 1/2018 |
| WO | WO-2018/005519 A3 | 1/2018 |
| WO | WO-2018/237335 A1 | 12/2018 |

OTHER PUBLICATIONS

Balmana, J. et al. (May 20, 2009). "BRCA in breast cancer: ESMO clinical recommendations," *Ann Oncol* 20 Suppl 4:19-20.

Baskar, S. et al. (Jan. 1, 2008). Targeting Human B Cell Chronic Lymphocytic Leukemia with a Monoclonal Antibody Specific for the receptor Tyrosine Kinane ROR1, *Journal of Immunotherapy* 31(9):969.

Brand, F.X. et al. (Jan.-Feb. 2006). "Prospect for anti-HER2 receptor therapy in breast cancer," *Anticancer Res* 26(16):463-470.

Burger, J.A. et al. (Dec. 17, 2015, e-published Dec. 6, 2015). "Ibrutinib as Initial Therapy for Patients with Chronic Lymphocytic Leukemia," *N Engl J Med* 373(25):2425-2437

Casset, F. et al. (Jul. 18, 2003). "A peptide mimetic of an anti-CD4 monoclonal antibody by rational design," *Biochem Biophys Res Commun* 307(1):198-205.

Choi, M. et al. (Jun. 2015). "Pre-clinical Specificity and Safety of UC-961, a First-In-Class Monoclonal Antibody Targeting ROR1," *Clin Lymphoma Myeloma Luek* 15 Suppl:S167-169.

Chou, T-C. (Sep. 2006). "Theoretical basis, experimental design, and computerized simulation of synergism and antagonism in drug combination studies," *Pharmacol Rev* 58(3):621-681.

Cui, B. et al. (2013). "Cirmtuzumab Vedotin (UC-961ADC3), An Anti-ROR1-Monomethyl Auristatin E Antibody-Drug Conjugate, Is a Potential Treatment for ROR1-Positive Leukemia and Solid Tumors," *Blood* 122:1637.

Daneshmanesh, A.H. et al. (Sep. 1, 2008). "Ror1, a cell surface receptor tyrosine kinase is expressed in chronic lymphocytic leukemia and may serve as a putative target for therapy," *Int J Cancer* 123(5):1190-1195.

De Pascalis, R. et al. (2002). "Grafting of "Abbreviated" Complementarity-Determining Regions Containing Specificity-Determining Residues Essential for Ligand Contact to Engineer a Less Immunogenic Humanized Monoclonal Antibody," *The Journal of Immunology* 169:3076-3084.

Dermer, G.B. (Mar. 1994). "The Last Word: Another Anniversary for the War on Cancer," *Bio/Technology* 12(3):320.

Eswaran, J. et al. (Aug. 2015, e-published May 6, 2015). "The pre-B-cell receptor checkpoint in acute lymphoblastic leukaemia," *Leukemia* 29(8):1623-1631.

Extended European Search Report dated Jan. 20, 2020, for EP Patent Application No. 17821087.8, 9 pages.

Freshney, R.I. (1983). *Culture of Animal Cells: A Manual of Basic Technique*, 4 pages.

George, J. et al. (Mar. 10, 1998). "Differential effects of anti-beta2-glycoprotein I antibodies on endothelial cells and on the manifestations of experimental antiphospholipid syndrome," *Circulation* 97(9):900-906.

Gura, T. et al. (Nov. 7, 1997). "Systems for identifying new drugs are often faulty," *Science* 278(5340):1041-1042.

International Search Report dated Sep. 9, 2013, for PCT Application No. PCT/US2013/032572, filed Mar. 15, 2013, 5 pages.

International Search Report dated Jan. 2, 2018, for PCT Application No. PCT/US2017/039536, filed Jun. 27, 2017, 5 pages.

Jain, R.K. (Jul. 1994). "Barriers to drug delivery in solid tumors," *Sci Am* 271(1):58-65.

Karoven, H. et al. (Apr. 15, 2017). "Targeting ROR1 identifies new treatment strategies in hematological cancers," *Biochem Soc Trans* 45(2):457-464.

Kataja, V. et al. (May 2009). "Primary breast cancer: ESMO clinical recommendations for diagnosis, treatment and follow-up," *Annals of Oncology* 20(Suppl 4):10-14.

Lippincott-Schwartz, J. (2002). "Antibodies as Cell Biological Tools," Chapter 16 in *Current Protocols in Cell Biology* 16.0.1-16.0.2.

Miyako, H. et al. (2006). *Surgery Frontier*, vol. 13, No. 3, pp. 40-43.

NCT01744691, ClinicalTrials.gov, Jan. 9, 2017, 21 pages.

NCT03088878, ClinicalTrials.gov, Mar. 27, 2017, 15 pages.

Nelson, H.D. et al. (Nov. 17, 2009). "Screening for breast cancer: an update for the U.S. Preventive Services Task Force," *Ann Intern Med* 151(10):727-737.

Parker, B. (Jun. 12, 2012). "ROR1 Expression in Human Breast Cancer," *AIM #3*, methods, paragraphs 1-3, 4 pages.

Paul, W.E. (1993). *Fundamental Immunology*, $3^{rd}$ Edition, pp. 292-295.

Ren, L. et al. (Feb. 2016, e-published Dec. 1, 2015). "Analysis of the Effects of the Bruton's tyrosine kinase (BTK) Inhibitor Ibrutinib on Monocyte Fcγ Receptor (FcγR) Function," *J Biol Chem* 291(6):3043-3052.

Rudikoff, S. et al. (Mar. 1982). "Single amino acid substitution altering antigen-binding specificity," *PNAS USA* 79(6):1979-1983.

(56) References Cited

OTHER PUBLICATIONS

Rushworth, S.A. et al. (Feb. 2014, e-published Dec. 4, 2013). "Identification of Bruton's tyrosine kinase as a therapeutic target in acute myeloid leukemia," *Blood* 123(8):1229-1238.

Skarzynski, M. et al. (Jan. 1, 2016, e-published Aug. 17, 2015). "Interactions between Ibrutinib and Anti-CD20 Antibodies: Competing Effects on the Outcome of Combination Therapy," *Clin Cancer Res* 22(1):86-95.

Strome, S.E et al. (Sep. 2007). "A mechanistic perspective of monoclonal antibodies in cancer therapy beyond target-related effects," *Oncologist* 12(9):1084-1095

University of California et al. (Mar. 23, 2017). "A Study of Cirmtuzumab and Ibrutinib in Patients with B-Cell Lymphoid Malignancies," located at https://clinicaltrials.gov/ct2/show/NCT03088878?term=cirmtuzumab&draw=2&rank=4, retrieved Jan. 10, 2020, 13 pages.

Written Opinion dated Sep. 9, 2013, for PCT Application No. PCT/US2013/032572, filed Mar. 15, 2013, 6 pages.

Written Opinion dated Jan. 2, 2018, for PCT Application No. PCT/US2017/039536, filed Jun. 27, 2017, 9 pages.

Yu, J. et al. (Jun. 2017, e-published Dec. 1, 2016). "Cirmtuzumab inhibits Wnt5a-induced Rac1 activation in chronic lymphocytic leukemia treated with ibrutinib," *Leukemia* 31(6):1333-1339.

Zhang, S. et al. (Dec. 2012). "The Onco-Embryonic Antigen ROR1 is Expressed by a Variety of Human Cancers," *Journal of Pathology* 181(6):1902-1910.

Zhao, X. et al. (Mar. 2015, e-published Oct. 4, 2014). "Combination of ibrutinib with ABT-199: synergistic effects on proliferation inhibition and apoptosis in mantle cell lymphoma cells through perturbation of BTK, AKT and BCL2 pathways," *Br J Haematol* 168(5):765-768.

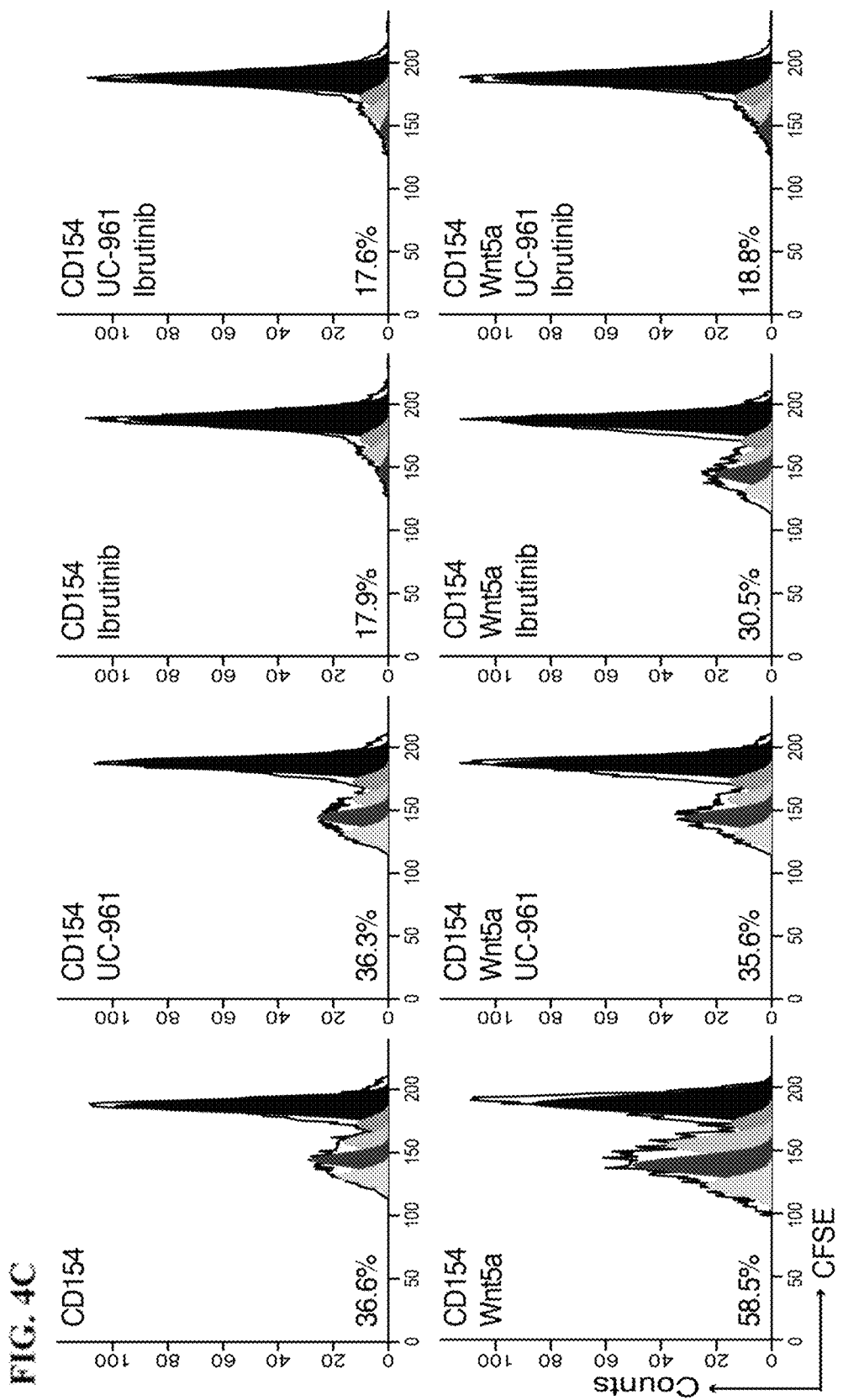

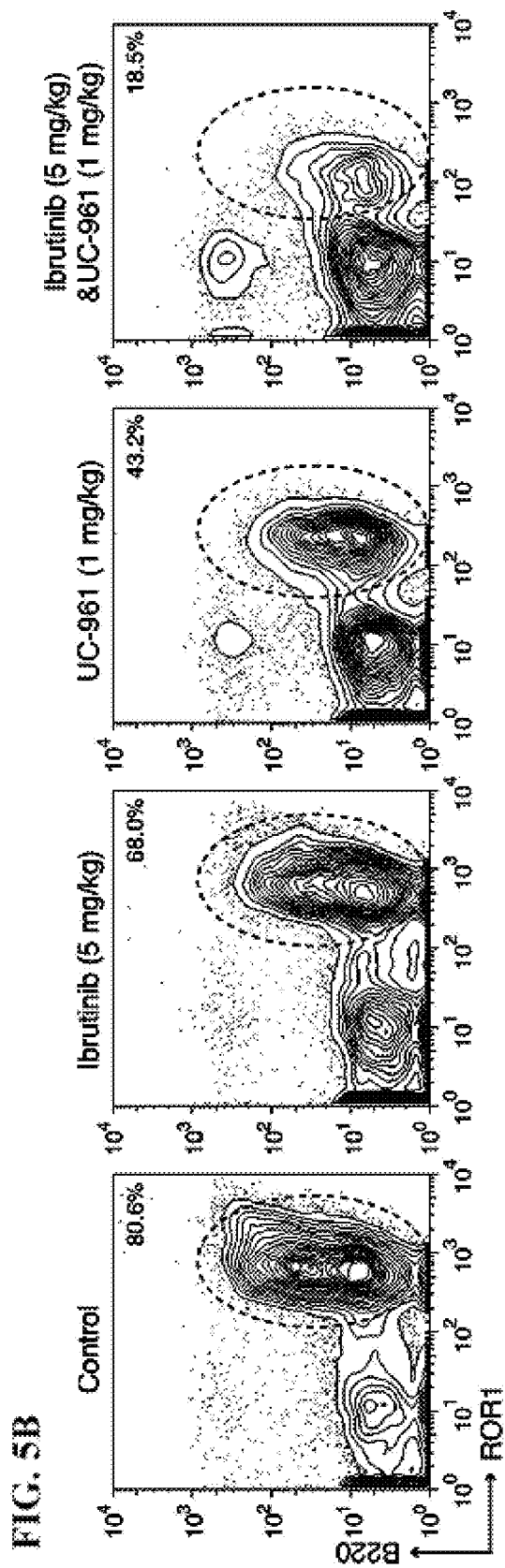

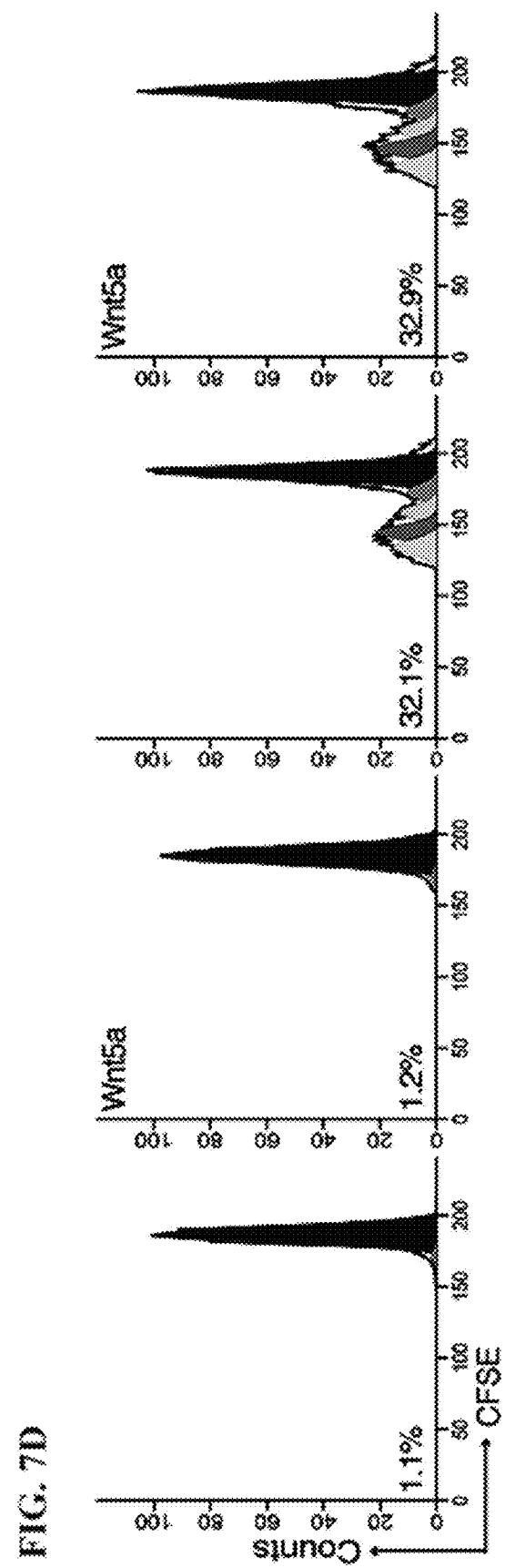

CANCER TREATMENT COMBINATIONS

CROSS-REFERENCES TO RELATED APPLICATIONS

This application is a continuation of U.S. patent application Ser. No. 15/634,802, filed Jun. 27, 2017, which claims priority to U.S. Provisional Application No. 62/355,171, filed Jun. 27, 2016, all of which are hereby incorporated by reference in their entireties and for all purposes.

STATEMENT AS TO RIGHTS TO INVENTIONS MADE UNDER FEDERALLY SPONSORED RESEARCH AND DEVELOPMENT

This invention was made with government support under Grant No. CA081534 awarded by the National Institutes of Health. The government has certain rights in the invention.

REFERENCE TO A "SEQUENCE LISTING," A TABLE, OR A COMPUTER PROGRAM LISTING APPENDIX SUBMITTED AS AN ASCII FILE

The Sequence Listing written in file 048537-582C01US_SEQUENCE_LISTING_ST25.txt, created on May 5, 2020, 10,963 bytes bytes, machine format IBM-PC, MS-Windows operating system, is hereby incorporated by reference.

BACKGROUND

Signaling via BCR (B-Cell Receptor) signaling is thought to play a role in the pathogenesis and/or progression of disease, e.g., chronic lymphocytic leukemia (CLL). Moreover, agents that target B-cell receptor (BCR) signaling in lymphoid and leukemia malignancies including ibrutinib and acalabrutinib (4-{8-Amino-3-[(2S)-1-(2-butynoyl)-2-pyrrolidinyl]imidazo[1,5-a]pyrazin-1-yl}-N-(2-pyridinyl) benzamide), which inhibit Bruton's tyrosine kinase (BTK), have shown significant clinical activity. By disrupting B-cell signaling pathways, BTK treatment has been associated with a dramatic lymph node response, but eradication of disease and relapse in high risk disease remain challenges.

Provided here are solutions to these and other problems in the art.

SUMMARY

The compositions and methods provided herein are, inter alia, useful for the treatment of leukemia. For example, provided herein are surprisingly effective methods for using the combination of anti-ROR-1 antibody with BCR inhibitors to treat chronic lymphocytic leukemia (CLL).

In an aspect is provided a method of treating cancer in a subject in need thereof, the method including administering to the subject a therapeutically effective amount of a Bruton's tyrosine kinase (BTK) antagonist and a tyrosine kinase-like orphan receptor 1 (ROR-1) antagonist.

In an aspect is provided a pharmaceutical composition including a BTK antagonist, a ROR-1 antagonist and a pharmaceutically acceptable excipient.

In an aspect is provided a pharmaceutical composition including a BTK antagonist, an anti-ROR-1 antibody and a pharmaceutically acceptable excipient, wherein the BTK antagonist and the anti-ROR-1 antibody are present in a combined synergistic amount, wherein the combined synergistic amount is effective to treat cancer in a subject in need thereof.

In an aspect, there is provided a method of treating cancer in a subject in need thereof. The method includes administering to the subject a therapeutically effective amount of a Bruton's tyrosine kinase (BTK) antagonist and an anti-ROR-1 antibody.

In another aspect, there is provided a pharmaceutical composition including a Bruton's tyrosine kinase (BTK) antagonist, an anti-ROR-1 antibody, and a pharmaceutically acceptable excipient.

BRIEF DESCRIPTION OF THE DRAWINGS

(FIG. 1A) Activated Rac1 was measured in CLL cells incubated with or without Wnt5a and treated with UC-961 or ibrutinib, as indicated on the top of each lane. (FIG. 1B) Wnt5a-induced activation of Rac1 in CLL cells without treatment or treated with UC-961 (10 µg/ml) and/or ibrutinib (0.5 µM). Mean Rac1 activation observed in five independent experiments is shown (n=5). (FIG. 1C) CLL cells were collected from ibrutinib treated patients (n=5). Activated Rac1 was measured in these CLL cells treated with or without Wnt5a or UC-961 indicated above each lane in vitro. (FIG. 1D) Rac1 activation was measured in CLL cells collected from patient treated with ibrutinib, which were treated with Wnt5a and/or UC-961. Mean Rac1 activation observed in five independent experiments is shown (n=5). The numbers below each lane are ratios of band IOD of activated versus total GTPase normalized to untreated samples. Data are shown as mean±SEM for each group. P<0.01; *P<0.001; ****P<0.0001, as calculated using one-way ANOVA with Tukey's multiple comparisons test.

(FIG. 2A) CD154-induced proliferation of CFSE-labeled CLL cells (n=6) with or without Wnt5a and treated with UC-961 or ibrutinib. One representative CLL sample is shown with the percent of dividing cells. (FIG. 2B) The bars indicate the mean proportions of CLL cells with diminished CFSE fluorescence from each of 6 different patients for each culture condition indicated at the bottom. Data are shown as mean±SEM, *P<0.05; **P<0.01, as determined by one-way ANOVA with Tukey's multiple comparisons test.

FIGS. 4A-4D. UC-961 inhibits Wnt5a-enhanced proliferation in ibrutinib-treated ROR-1×TCL1 leukemia cells. (FIG. 4A) Activated Rac1 was measured in ROR-1×TCL1 leukemia cells incubated with or without Wnt5a and treated with UC-961 (10 µg/ml) and/or ibrutinib (0.5 µM), as indicated on the top of each lane. The numbers below each lane are ratios of band IOD of activated versus total GTPase normalized to untreated samples. (FIG. 4B) Wnt5a-induced activation of Rac1 in ROR-1×TCL1 leukemia cells without treatment or treated with UC-961 (10 μg/ml) and/or ibrutinib (0.5 μM). Mean Rac1 activation observed in five independent experiments is shown (n=5). (FIG. 4C) CD154-induced proliferation of CFSE-labeled ROR-1×TCL1 leukemia cells (n=6) with or without Wnt5a and treated with UC-961 or ibrutinib. One representative ROR-1×TCL1 leukemia cell sample is shown with the percent of dividing cells. (FIG. 4D) The bars indicate the mean proportions of ROR-1×TCL1 leukemia cells with diminished CFSE fluorescence from each of 5 different mice for each culture condition indicated at the bottom. Data are shown as mean±SEM; P<0.01; *P<0.001; ****P<0.0001, as calculated using one-way ANOVA with Tukey's multiple comparisons test.

FIGS. 5A-5C. Additive inhibitory effect of UC-961 and ibrutinib in ROR-1×TCL1 leukemia xenograft mice. (FIG. 5A) Representative spleens of $Rag2^{-/-}\gamma_c^{-/-}$ mice were shown, which were collected 25 days after receiving an intravenous infusion of $2\times10^4$, ROR-1×TCL1 leukemia cells. (FIG. 5B) Combination of UC-961 and ibrutinib inhibits engraftment of ROR-1×TCL1 leukemia cells in $Rag2^{-/-}\gamma_c^{-/-}$ mice. $Rag2^{-/-}\gamma_c^{-/-}$ mice were engrafted with $2\times10^4$, ROR-1×TCL1 leukemia cells and then given single i.v injection of 1 mg/kg UC-961 on day 1 or daily does 5-mg/kg ibrutinib. Contour plots depicting the fluorescence of splenic lymphocytes harvested on day 25 post adoptive transfer from representative mice (n=5) that received treatment indicated at the top, as determined by light scatter characteristics, after staining the cells with fluorochrome-conjugated mAb specific for B220 (abscissa) and human ROR-1 (ordinate). The percentages in the top right of each contour plot indicate the proportion of the blood mononuclear cells having $CD5^+B220^{low}ROR-1^+$ phenotype of the leukemia cells. (FIG. 5C) Total number of ROR-1×TCL1 leukemia cells in spleens of recipient $Rag2^{-/-}\gamma_c^{-/-}$ mice 25 days after adoptive transfer of $2\times10^4$, ROR-1×TCL1 leukemia cells that received single injection of 1-mg/kg UC-961 or daily injections of 5-mg/kg ibrutinib, as determined by flow cytometric analysis and cell count. Each shape represents the number of leukemia cells found in individual mice. Data are shown as mean±SEM for each group of animals (n=5); ***P<0.001, as calculated using one-way ANOVA with Tukey's multiple comparisons test.

(FIG. 6A) Activated Rac1 was measured in CLL cells incubated with or without WntSa or ibrutinib at concentrations of 0, 0.25, 0.5 or 1.0 μM, as indicated on the top of each lane. (FIG. 6B) CLL cells were treated with increasing doses of ibrutinib for 1 hour and then assayed for occupancy of the BTK active site. (FIG. 6C) Anti-μ-induced calcium mobilization in CLL cells after treatment with or without different dose of ibrutinib. The relative mean fluorescence intensity in intracellular calcium is plotted as a function of time. The arrow labeled "IgM" indicates the time at which the anti-μ was added to the cells. (FIG. 6D) Determination of cell viability by staining with DiOC6 and PI. Presented are dot maps of CLL cells from a representative patient defining the relative green (DiOC6) and red (PI) fluorescence intensities of the leukemia cells on the horizontal and vertical axes, respectively. The vital cell population (DiOC6$^+$PI$^-$) was determined for CLL cells after treatment with different doses of ibrutinib. The percentage of vital cells is displayed in each dot map.

FIGS. 7A-7E. Wnt5a induces Rac1 activation in CLL cells treated with ibrutinib. (FIG. 7A) CF SE assay for CLL proliferation induced by Wnt5a without CD154. Fluorescence of CFSE-labeled CLL cells (n=6) co-cultured for 5 days with wild-type HeLa cells without (left panel) or with (right panel) exogenous Wnt5a in the presence of IL-4/10. The results of assays on one representative CLL sample are shown with the percent of dividing cells indicated in the lower left of each panel. (FIG. 7B) CFSE assay for ROR-1×TCL1 leukemia cell proliferation induced by Wnt5a without CD154. Fluorescence of CFSE-labeled CLL cells (n=6) co-cultured for 5 days with HeLa cells without (left panel) or with (right panel) exogenous Wnt5a in the presence of IL-4/10. The results of assays on one representative CLL sample are shown with the percent of dividing cells indicated in the lower left of each panel. (FIG. 7C) Rac1 activation was measured in serum starved TCL1 leukemia cells, which were treated with Wnt5a for 30 min. Whole-cell lysates were run on parallel gels to examine total Rac1. The numbers below each lane are ratios of band IOD of activated versus total GTPase, normalized with respect to that of untreated samples. (FIG. 7D) CFSE assay for TCL1 leukemia cell proliferation induced by Wnt5a and/or CD154. Fluorescence of CF SE-labeled TCL1 leukemia cells (n=3) co-cultured for 5 days with wild-type HeLa or HeLacD154 cells without or with exogenous Wnt5a in the presence of IL-4/10. The results of assays on one representative TCL1 leukemia sample are shown with the percent of dividing cells indicated in the lower left of each panel. (FIG. 7E) Mean proportions of dividing CLL cells from TCL1 leukemia cells (n=3) under conditions indicated at the bottom. Data are shown as mean±SEM for each group; p-values were calculated using one-way ANOVA with Tukey's multiple comparisons test; ns: non-significant.

(FIG. 8A) Dose-dependent inhibitory effect of ibrutinib in ROR-1×TCL1 leukemia xenograft mice. (FIG. 8B) Dose-dependent inhibitory effect of UC-961 in ROR-1×TCL1 leukemia xenograft mice. Each shape represents the number of leukemia cells found in individual mice. Data are shown as mean±SEM for each group of animals (n=6); *P<0.05; ***P<0.001, as calculated using one-way ANOVA with Tukey's multiple comparisons test.

(FIG. 12A) Activated Rac1 was measured in the freshly isolated ibrutinib-treated CLL cells or isolated ibrutinib-treated CLL cells cultured in serum free media without or with exogenous Wnt5a (200 ng/ml), as indicated on the top of each lane. (FIG. 12B) Activated Rac1 was measured in the freshly isolated ibrutinib-treated CLL cells or isolated ibrutinib-treated CLL cells cultured in serum free media with or without Wnt5a (200 ng/ml). Mean Rac1 activation observed in four independent experiments is shown (n=4). (FIG. 12C) CLL cells were collected from ibrutinib treated patients (n=4). Activated Rac1 was measured in CLL cells treated with or without Wnt5a (200 ng/ml) or cirmtuzumab (10 μg/ml), as indicated above each lane of the immunoblot (FIG. 12D) Rac1 activation was measured in CLL cells collected from patients undergoing therapy with ibrutinib, which were treated with Wnt5a (200 ng/ml) and/or cirmtuzumab (10 μg/ml). The average Rac1 activation observed in five independent experiments is shown (n=5). (FIG. 12E) Activated Rac1 was measured in CLL cells incubated with or without Wnt5a and treated with cirmtuzumab (10 µg/ml) or ibrutinib (0.5 µM), as indicated on the top of each lane. (FIG. 12F) Wnt5a-induced activation of Rac1 in CLL cells without treatment or treated with cirmtuzumab and/or ibrutinib. Mean Rac1 activation observed in five independent experiments is shown (n=5). The numbers below each lane are ratios of band IOD of activated versus total GTPase normalized to untreated samples. Data are shown as mean±SEM for each group. $P<0.01$; *$P<0.001$; ****$P<0.0001$, as calculated using one-way ANOVA with Tukey's multiple comparisons test.

(FIG. 13A) CD154-induced proliferation of CFSE-labeled CLL cells (n=6) with or without Wnt5a and treated with cirmtuzumab (10 µg/ml) or ibrutinib (0.5 µM). One representative CLL sample is shown with the percent of dividing cells. (FIG. 13B) The bars indicate the mean proportions of CLL cells with diminished CFSE fluorescence from each of 6 different patients for each culture condition indicated at the bottom. (FIG. 13C) CLL cells were co-cultured on HeLacD154 in the presence of IL-4/10 or Wnt5a, and then treated with cirmtuzumab (10 µg/ml) or ibrutinib (0.5 µM) for 4 days, subjected to cell-cycle analysis following PI staining. One representative CLL sample is shown. (FIG. 13D) The mean fraction of cells in S/G2/M phase for all 4 patients tested is presented. Data are shown as mean±SEM, *$P<0.05$; **$P<0.01$, as determined by one-way ANOVA with Tukey's multiple comparisons test.

(FIG. 14A) CLL cells were injected to the peritoneal cavity of $Rag2^{-/-}\gamma_c^{-/-}$ mice 1 day before treatment. Peritoneal lavage was collected 7 days after cell injection and subjected to residual CLL determination by cell counting and flow cytometry analysis following staining with mAb specific for CD5, CD19, and CD45. The percentages shown in the top right of each contour plot indicates the proportion of CLL cells among the cells harvested from mice after treatment. (FIG. 14B) Each bar in the graph represents the percentage of CLL cells among harvested cells from mice after treatment, normalized with respect to the percentage of CLL cells among cells harvested from mice without treatment, which was to 100%. Data shown are mean±SEM from 3 different patients with 5 mice in each group; *$P<0.001$; **$P<0.0001$, as calculated using one-way ANOVA with Tukey's multiple comparisons test.

(FIG. 15A) Activated Rac1 was measured in ROR-1×TCL1 leukemia cells incubated with or without Wnt5a (200 ng/ml) and treated with cirmtuzumab (10 µg/ml) and/or ibrutinib (0.5 µM), as indicated on the top of each lane. The numbers below each lane are ratios of the band densities of activated versus total GTPase, normalized to untreated samples. (FIG. 15B) Activation of Rac1 in ROR-1×TCL1 leukemia cells treated with Wnt5a with or without cirmtuzumab (10 µg/ml) and/or ibrutinib (0.5 µM). The average Rac1 activation observed in five independent experiments is shown (n=5). (FIG. 15C) CD154-induced proliferation of CFSE-labeled ROR-1×TCL1 leukemia cells (n=5) with or without Wnt5a (200 ng/ml) and/or cirmtuzumab (10 µg/ml) or ibrutinib (0.5 µM). The bars indicate the mean proportions of ROR-1×TCL1 leukemia cells from each of 5 different mice that have diminished CFSE fluorescence for each culture condition, as indicated at the bottom. Data are shown as mean±SEM; *$P<0.05$; $P<0.01$; **$P<0.0001$, as calculated using one-way ANOVA with Tukey's multiple comparisons test.

(FIG. 16A) Representative spleens of $Rag2^{-/-}\gamma_c^{-/-}$ mice were shown, which were collected 25 days after receiving an intravenous infusion of $2\times10^4$ROR-1×TCL1 leukemia cells. (FIG. 16B) Combination of cirmtuzumab and ibrutinib inhibits engraftment of ROR-1×TCL1 leukemia cells in $Rag2^{-/-}\gamma_c^{-/-}$ mice. $Rag2^{-/-}\gamma_c^{-/-}$ mice were engrafted with $2\times10^4$, ROR-1×TCL1 leukemia cells and then given single intravenous injection of 1 mg/kg cirmtuzumab on day 1, or daily doses of 5 mg/kg ibrutinib via oral gavage. Contour plots depicting the fluorescence of lymphocytes harvested on day 25 post adoptive transfer from representative mice (n=5) that received treatment, as indicated at the top, after staining the cells with fluorochrome-conjugated mAb specific for B220 (abscissa) and human ROR-1 (ordinate). The percentages in the top right of each contour plot indicate the proportion of the blood mononuclear cells having CD5$^+$B220$^{low}$ROR-1$^+$ phenotype of the leukemia cells. (FIG. 16C) Total number of ROR-1×TCL1 leukemia cells in spleens of recipient $Rag2^{-/-}\gamma_c^{-/-}$ mice 25 days after adoptive transfer of $2\times10^4$, ROR-1×TCL1 leukemia cells that received single injection of 1 mg/kg cirmtuzumab or daily injections of 5 mg/kg ibrutinib. Each symbol represents the number of leukemia cells found in individual mice. Data are shown as mean±SEM for each group of animals (n=5); *$P<0.05$, $P<0.01$, *$P<0.001$, as calculated using one-way ANOVA with Tukey's multiple comparisons test.

(FIG. 17A) Representative spleens of ROR-1-Tg mice were shown, which were collected 25 days after receiving an intravenous infusion of $2\times10^4$ROR-1×TCL1 leukemia cells. (FIG. 17B) Combination of cirmtuzumab and ibrutinib inhibits engraftment of ROR-1×TCL1 leukemia cells in ROR-1-Tg mice. ROR-1-Tg mice were engrafted with $2\times10^4$, ROR-1×TCL1 leukemia cells and then given weekly intravenous injection of 10 mg/kg cirmtuzumab or daily does 5 mg/kg ibrutinib via oral gavage. Contour plots depicting the fluorescence of lymphocytes harvested 25 days after adoptive transfer of representative mice (n=6) that received treatment, as indicated at the top, after staining the cells with fluorochrome-conjugated mAb specific for B220 (abscissa) and human ROR-1 (ordinate). The percentages in the top right of each contour plot indicate the proportion of the blood mononuclear cells having CD5$^+$B220$^{low}$ROR-1$^+$ phenotype of the leukemia cells. (FIG. 17C) Total number of ROR-1×TCL1 leukemia cells in spleens of recipient ROR-1-Tg mice 28 days after adoptive transfer of $2\times10^4$, ROR-1×TCL1 leukemia cells that received weekly injection of 10 mg/kg cirmtuzumab and/or daily doses of ibrutinib (at 5 mg/kg). Each symbol represents the number of leukemia cells found in individual mice. Data are shown as mean±SEM for each group of animals (n=6); *$P<0.05$, **$P<0.01$, as calculated using one-way ANOVA with Tukey's multiple comparisons test.

(FIG. 18A) Gating strategy for dividing CLL cells. Cells were first gated on size and singularity followed by PI exclusion to identify live cells for further analysis. Live CD5 and CD19 CLL cells were examined for fluorescence after staining with CFSE. The percentages of dividing CLL cells were calculated by computing the proportion of cells that had lower CFSE fluorescence. (FIG. 18B) Fluorescence of CFSE-labeled CLL cells (n=6) co-cultured for 5 days with wild-type HeLa cells without (top panel) or with (lower panel) exogenous Wnt5a in the presence of IL-4/10. The results of one representative CLL sample are shown with the percent of dividing cells indicated in the lower left corner of each histogram.

FIGS. 19A-19B. Cell Cycle Analysis Of CLL Cells Treated With Cirmtuzumab Or Ibrutinib, With Or Without Exogenous Of Wnt5a. (FIG. 19A) Leukemia cells were co-cultured on HeLacD154 in the presence of IL-4/10 or Wnt5a, and then treated with cirmtuzumab (10 µg/ml) or ibrutinib (0.5 µM) for 4 days, subjected to cell-cycle analysis following PI staining. One representative leukemia sample is shown. (FIG. 19B) The mean proportions of leukemia cells in S/G2/M phase for all 3 samples tested is presented. Data are shown as mean±SEM, $*P<0.05$; $**P<0.01$, as determined by one-way ANOVA with Tukey's multiple comparisons test.

(FIG. 20A) Dose-dependent inhibitory effect of ibrutinib in ROR-1×TCL1 leukemia engrafted mice. (FIG. 20B) Dose-dependent inhibitory effect of cirmtuzumab in ROR-1×TCL1 leukemia engrafted mice. Each symbol represents the number of leukemia cells found in individual mice. Data are shown as mean±SEM for each group of animals (n=6); $*P<0.05$; $***P<0.001$, as calculated using one-way ANOVA with Tukey's multiple comparisons test.

(FIG. 22A) Gating on the MCL cells, which express CD5 and CD19 (top left). The shaded histograms show the fluorescence of the gated MCL cells stained with fluorochrome-conjugated mAb specific for other surface antigens. In contrast to CLL cells, the MCL cells failed to stain with a mAb specific for CD200 (top right) or CD23 (bottom left). Similar with CLL, MCL expresses high levels of ROR-1 (bottom right). The open histograms depict fluorescence of cells stained with an isotype control antibody. (FIG. 22B) ΔMFI of ROR-1 in MCL vs CLL. ns=Not significant. (FIG. 22C) Plasma Wnt5a in patients with MCL vs. age-matched control subjects (n=4 per group; $P<0.05$, Student's t test).

(FIG. 23A) Activated Rac1 was measured in MCL cells treated with or without Wnt5a (200 ng/ml), with or without ibrutinib (0.5 µM) or with or without cirmtuzumab (10 µg/ml), as indicated above each lane of the immunoblot. The numbers below each lane are ratios of band IOD of activated versus total GTPase normalized to untreated samples. (FIG. 23B) Wnt5a-induced activation of Rac1 in CLL cells without treatment or treated with cirmtuzumab and/or ibrutinib. Mean Rac1 activation observed in five independent experiments is shown (n=3). The numbers below each lane are ratios of band IOD of activated versus total GTPase normalized to untreated samples. Data are shown as mean±SEM for each group. $****P<0.0001$, as calculated using one-way ANOVA with Tukey's multiple comparisons test. (FIG. 23C) MCL cells were co-cultured on HeLacD154 in the presence of IL-4/10 or Wnt5a, and then treated with cirmtuzumab (10 m/ml) or ibrutinib (0.5 µM) for 4 days, subjected to cell-cycle analysis following PI staining. One representative CLL sample is shown. (FIG. 23D) The mean fraction of cells in S/G2 phase for all MCL patients tested is presented (n=3). Data are shown as mean±S.E.M.; $*P<0.05$; $**P<0.01$, as determined by one-way ANOVA with Tukey's multiple comparisons test. ns=Not significant.

DETAILED DESCRIPTION

Definitions

Figure 1A:
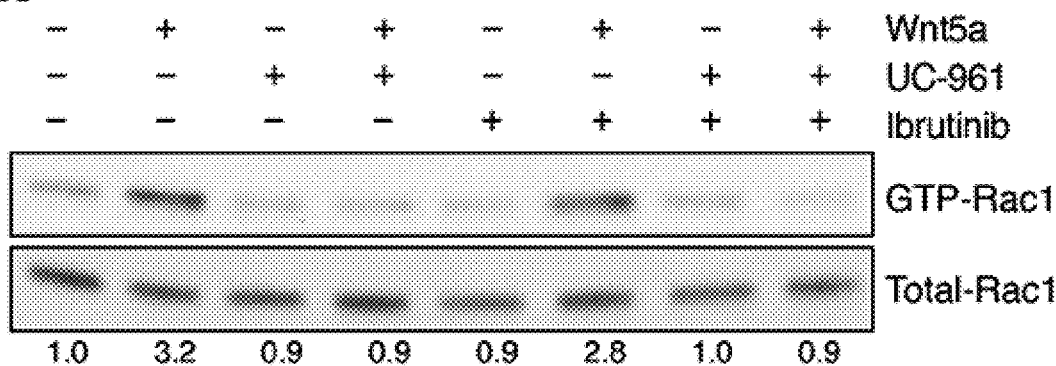
FIGS. 1A-1D. UC-961 inhibits Wnt5a-induced Rac1 activation in ibrutinib-treated CLL cells.

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e., unbranched) or branched non-cyclic carbon chain (or carbon), or combination thereof, which may be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched non-cyclic chain, or combinations thereof, including at least one carbon atom and at least one heteroatom (e.g. O, N, P, Si, and S), and wherein the nitrogen and sulfur atoms may optionally be oxidized, and the nitrogen heteroatom may optionally be quaternized. The heteroatom(s) (e.g. O, N, P, S, and Si) may be placed at any interior position of the heteroalkyl group or at the position at which the alkyl group is attached to the remainder of the molecule. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, non-aromatic cyclic versions of "alkyl" and "heteroalkyl," respectively, wherein the carbons making up the ring or rings do not necessarily need to be bonded to a hydrogen due to all carbon valencies participating in bonds with non-hydrogen atoms. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, 3-hydroxy-cyclobut-3-enyl-1,2, dione, 1H-1,2,4-triazolyl-5(4H)-one, 4H-1,2,4-triazolyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. A heterocycloalkyl moiety may include one ring heteroatom (e.g., O, N, S, Si, or P). A heterocycloalkyl moiety may include two optionally different ring heteroatoms (e.g., O, N, S, Si, or P). A heterocycloalkyl moiety may include three optionally different ring heteroatoms (e.g., O, N, S, Si, or P). A heterocycloalkyl moiety may include four optionally different ring heteroatoms (e.g., O, N, S, Si, or P). A heterocycloalkyl moiety may include five optionally different ring heteroatoms (e.g., O, N, S, Si, or P). A heterocycloalkyl moiety may include up to 8 optionally different ring heteroatoms (e.g., O, N, S, Si, or P).

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo(C$_1$-C$_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Non-limiting examples of aryl and heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene. A heteroaryl moiety may include one ring heteroatom (e.g., O, N, or S). A heteroaryl moiety may include two optionally different ring heteroatoms (e.g., O, N, or S). A heteroaryl moiety may include three optionally different ring heteroatoms (e.g., O, N, or S). A heteroaryl moiety may include four optionally different ring heteroatoms (e.g., O, N, or S). A heteroaryl moiety may include five optionally different ring heteroatoms (e.g., O, N, or S). An aryl moiety may have a single ring. An aryl moiety may have two optionally different rings. An aryl moiety may have three optionally different rings. An aryl moiety may have four optionally different rings. A heteroaryl moiety may have one ring. A heteroaryl moiety may have two optionally different rings. A heteroaryl moiety may have three optionally different rings. A heteroaryl moiety may have four optionally different rings. A heteroaryl moiety may have five optionally different rings.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein.

The term "oxo," as used herein, means an oxygen that is double bonded to a carbon atom.

The term "alkylsulfonyl," as used herein, means a moiety having the formula —S($O_2$)—R', where R' is a substituted or unsubstituted alkyl group as defined above. R' may have a specified number of carbons (e.g., "$C_1$-$C_4$ alkylsulfonyl").

Each of the above terms (e.g., "alkyl", "heteroalkyl", "cycloalkyl", "heterocycloalkyl", "aryl", and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R"', —OC(O)R', —C(O)R', —$CO_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")'NR"', —S(O)R', —S(O)$_2$R', —S(O)$_2$NR'R", —NRSO$_2$R', —NR'NR"R"', —ONR'R", —NR'C=(O)NR"NR"'R"", —CN, —NO$_2$, in a number ranging from zero to (2m'+1), where m' is the total number of carbon atoms in such radical. R, R', R", R"', and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R"', and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: —OR', —NR'R", —SR', -halogen, —SiR'R"R"', —OC(O)R', —C(O)R', —$CO_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —NR'NR"R"', —ONR'R", —NR'C=(O)NR"NR"'R"", —CN, —NO$_2$, —R', —N$_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R"', and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R'", and R""
groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In embodiments, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure.

For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R'")$_d$", where s and d are independently integers of from 0 to 3, and X' is —O—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties:
(A) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and
(B) alkyl, heteroalkyl, cycloalkyl, heterocycloalkyl, aryl, heteroaryl, substituted with at least one substituent selected from:
(i) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and
(ii) alkyl, heteroalkyl, cycloalkyl, heterocycloalkyl, aryl, heteroaryl, substituted with at least one substituent selected from:
(a) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and
(b) alkyl, heteroalkyl, cycloalkyl, heterocycloalkyl, aryl, heteroaryl, substituted with at least one substituent selected from: oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention. Salts tend to be more soluble in aqueous or other protonic solvents than are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Provided herein are agents (e.g. compounds, drugs, therapeutic agents) that may be in a prodrug form. Prodrugs of the compounds described herein are those compounds that readily undergo chemical changes under select physiological conditions to provide the final agents (e.g. compounds, drugs, therapeutic agents). Additionally, prodrugs can be converted to agents (e.g. compounds, drugs, therapeutic agents) by chemical or biochemical methods in an ex vivo environment. Prodrugs described herein include compounds that readily undergo chemical changes under select physiological conditions to provide agents (e.g. compounds, drugs, therapeutic agents) to a biological system (e.g. in a subject).

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

Certain compounds of the present invention possess asymmetric carbon atoms (optical or chiral centers) or double bonds; the enantiomers, racemates, diastereomers, tautomers, geometric isomers, stereoisomeric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^{3}H$), iodine-125 ($^{125}I$ or carbon-14 ($^{14}C$). All isotopic variations of the compounds of the present invention, whether radioactive or not, are encompassed within the scope of the present invention.

Analog" and "analogue" are used interchangeably and are used in accordance with their plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound, including isomers thereof. Accordingly, an analog is a compound that is similar or comparable in function and appearance but not in structure or origin to a reference compound.

The symbol "⌇" denotes the point of attachment of a chemical moiety to the remainder of a molecule or chemical formula.

In embodiments, a compound as described herein may include multiple instances of $R^2$ and/or other variables. In such embodiments, each variable may optional be different and be appropriately labeled to distinguish each group for greater clarity. For example, where each $R^2$ is different, they may be referred to, for example, as $R^{2.1}$, $R^{2.2}$, $R^{2.3}$, and/or $R^{2.4}$ respectively, wherein the definition of $R^2$ is assumed by $R^{2.1}$, $R^{2.2}$, $R^{2.3}$, and/or $R^{2.4}$. The variables used within a definition of $R^2$ and/or other variables that appear at multiple instances and are different may similarly be appropriately labeled to distinguish each group for greater clarity. In some embodiments, the compound is a compound described herein (e.g., in an aspect, embodiment, example, claim, table, scheme, drawing, or figure).

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Where a moiety is substituted with an R substituent, the group may be referred to as "R-substituted." Where a moiety is R-substituted, the moiety is substituted with at least one R substituent and each R substituent is optionally different. For example, where a moiety herein is $R^{12}$-substituted or unsubstituted alkyl, a plurality of $R^{12}$ substituents may be attached to the alkyl moiety wherein each $R^{12}$ substituent is optionally different. Where an R-substituted moiety is substituted with a plurality R substituents, each of the R-substituents may be differentiated herein using a prime symbol (') such as R', R'', etc. For example, where a moiety is $R^{12}$-substituted or unsubstituted alkyl, and the moiety is substituted with a plurality of $R^{12}$ substituents, the plurality of $R^{12}$ substituents may be differentiated as $R^{12\prime}$, $R^{12\prime\prime}$, $R^{12\prime\prime\prime}$, etc. In embodiments, the plurality of R substituents is 3. In embodiments, the plurality of R substituents is 2.

In embodiments, a compound as described herein may include multiple instances of $R^1$, $R^2$, $R^3$, $R^4$, $R^5$, $R^6$, $R^7$, $R^9$, $R^{10}$, $R^{11}$, $R^{12}$, $R^{13}$, $R^{14}$ and/or other variables. In such embodiments, each variable may optional be different and be appropriately labeled to distinguish each group for greater clarity. For example, where each $R^1$, $R^2$, $R^3$, $R^4$, $R^5$, $R^6$, $R^7$, $R^9$, $R^{10}$, $R^{11}$, $R^{12}$ $R^{13}$, and/or $R^{14}$, is different, they may be referred to, for example, as $R^{1.1}$, $R^{1.2}$, $R^{1.3}$, $R^{1.4}$, $R^{2.1}$, $R^{2.2}$, $R^{2.3}$, $R^{2.4}$, $R^{3.1}$, $R^{3.2}$, $R^{3.3}$, $R^{3.4}$, $R^{4.1}$, $R^{4.2}$, $R^{4.3}$, $R^{4.4}$, $R^{5.1}$, $R^{5.2}$, $R^{5.3}$, $R^{5.4}$, $R^{6.1}$, $R^{6.2}$, $R^{6.3}$, $R^{6.4}$, $R^{7.1}$, $R^{7.2}$, $R^{7.3}$, $R^{7.4}$, $R^{9.1}$, $R^{9.2}$, $R^{9.3}$, $R^{9.4}$, $R^{10.1}$, $R^{10.2}$, $R^{10.3}$, $R^{10.4}$, $R^{11.1}$, $R^{11.2}$, $R^{11.3}$, $R^{11.4}$, $R^{12.1}$, $R^{12.2}$, $R^{12.3}$, $R^{12.4}$, $R^{13.1}$, $R^{13.2}$, $R^{13.3}$, $R^{13.4}$, $R^{14.1}$, $R^{14.2}$, $R^{14.3}$, and/or $R^{14.4}$, respectively, wherein the definition of $R^1$ is assumed by $R^{1.1}$, $R^{1.2}$, $R^{1.3}$, and/or $R^{1.4}$, the definition of $R^2$ is assumed by $R^{2.1}$, $R^{2.2}$, $R^{2.3}$, and/or $R^{2.4}$, the definition of $R^3$ is assumed by $R^{3.1}$, $R^{3.2}$, $R^{3.3}$, and/or $R^{3.4}$, the definition of $R^4$ is assumed by $R^{4.1}$, $R^{4.2}$, $R^{4.3}$, and/or $R^{4.4}$, the definition of $R^5$ is assumed by $R^{5.1}$, $R^{5.2}$, $R^{5.3}$, and/or $R^{5.4}$, the definition of $R^6$ is assumed by $R^{6.1}$, $R^{6.2}$, $R^{6.3}$, and/or, $R^{6.4}$, the definition of $R^7$ is assumed by $R^{7.1}$, $R^{7.2}$, $R^{7.3}$, and/or $R^{7.4}$, the definition of $R^9$ is assumed by $R^{9.1}$, $R^{9.2}$, $R^{9.3}$, and/or $R^{9.4}$, the definition of $R^{10}$ is assumed by $R^{10.1}$, $R^{10.2}$, $R^{10.3}$, and/or, $R^{10.4}$, the definition of $R^{11}$ is assumed by $R^{11.1}$, $R^{11.2}$, $R^{11.3}$, and/or $R^{11.4}$, the definition of $R^{12}$ is assumed by $R^{12.1}$, $R^{12.2}$, $R^{12.3}$, and/or $R^{12.4}$, the definition of $R^{13}$ is assumed by $R^{13.1}$, $R^{13.2}$, $R^{13.3}$, and/or, $R^{13.4}$, the definition of $R^{14}$ is assumed by $R^{14.1}$, $R^{14.2}$, $R^{14.3}$, and/or $R^{14.4}$. The variables used within a definition of $R^1$, $R^2$, $R^3$, $R^4$, $R^5$, $R^6$, $R^7$, $R^9$, $R^{10}$, $R^{11}$, $R^{12}$, $R^{13}$ and/or $R^{14}$, and/or other variables that appear at multiple instances and are different may similarly be appropriately labeled to distinguish each group for greater clarity.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

Antibodies are large, complex molecules (molecular weight of ~150,000 or about 1320 amino acids) with intricate internal structure. A natural antibody molecule contains two identical pairs of polypeptide chains, each pair having one light chain and one heavy chain. Each light chain and heavy chain in turn consists of two regions: a variable ("V") region involved in binding the target antigen, and a constant ("C") region that interacts with other components of the immune system. The light and heavy chain variable regions come together in 3-dimensional space to form a variable region that binds the antigen (for example, a receptor on the surface of a cell). Within each light or heavy chain variable region, there are three short segments (averaging 10 amino acids in length) called the complementarity determining regions ("CDRs"). The six CDRs in an antibody variable domain (three from the light chain and three from the heavy chain) fold up together in 3-dimensional space to form the actual antibody binding site which docks onto the target antigen. The position and length of the CDRs have been precisely defined by Kabat, E. et al., Sequences of Proteins of Immunological Interest, U.S. Department of Health and Human Services, 1983, 1987. The part of a variable region not contained in the CDRs is called the framework ("FR"), which forms the environment for the CDRs.

The term "antibody" is used according to its commonly known meaning in the art. Antibodies exist, e.g., as intact immunoglobulins or as a number of well-characterized fragments produced by digestion with various peptidases. Thus, for example, pepsin digests an antibody below the disulfide linkages in the hinge region to produce $F(ab)'_2$, a dimer of Fab which itself is a light chain joined to $V_H$-$C_{H1}$ by a disulfide bond. The $F(ab)'_2$ may be reduced under mild conditions to break the disulfide linkage in the hinge region, thereby converting the $F(ab)'_2$ dimer into an Fab' monomer. The Fab' monomer is essentially Fab with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., Nature 348:552-554 (1990)).

For preparation of monoclonal or polyclonal antibodies, any technique known in the art can be used (see, e.g., Kohler & Milstein, Nature 256:495-497 (1975); Kozbor et al., Immunology Today 4:72 (1983); Cole et al., pp. 77-96 in Monoclonal Antibodies and Cancer Therapy (1985)). "Monoclonal" antibodies (mAb) refer to antibodies derived from a single clone. Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., Nature 348: 552-554 (1990); Marks et al., Biotechnology 10:779-783 (1992)).

The epitope of a mAb is the region of its antigen to which the mAb binds. Two antibodies bind to the same or overlapping epitope if each competitively inhibits (blocks) binding of the other to the antigen. That is, a 1×, 5×, 10×, 20× or 100× excess of one antibody inhibits binding of the other by at least 30% but preferably 50%, 75%, 90% or even 99% as measured in a competitive binding assay (see, e.g., Junghans et al., Cancer Res. 50:1495, 1990). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Antibodies exist, for example, as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region, thereby converting the F(ab)'2 dimer into an Fab' monomer. The Fab' monomer is essentially the antigen dinging portion with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., Nature 348:552-554 (1990)).

A single-chain variable fragment (scFv) is typically a fusion protein of the variable regions of the heavy (VH) and light chains (VL) of immunoglobulins, connected with a short linker peptide of 10 to about 25 amino acids. The linker may usually be rich in glycine for flexibility, as well as serine or threonine for solubility. The linker can either connect the N-terminus of the VH with the C-terminus of the VL, or vice versa.

For preparation of suitable antibodies of the invention and for use according to the invention, e.g., recombinant, monoclonal, or polyclonal antibodies, many techniques known in the art can be used (see, e.g., Kohler & Milstein, Nature 256:495-497 (1975); Kozbor et al., Immunology Today 4: 72 (1983); Cole et al., pp. 77-96 in Monoclonal Antibodies and Cancer Therapy, Alan R. Liss, Inc. (1985); Coligan, Current Protocols in Immunology (1991); Harlow & Lane, Antibodies, A Laboratory Manual (1988); and Goding, Monoclonal Antibodies: Principles and Practice (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, Immunology (3rd ed. 1997)). Techniques for the production of single chain antibodies or recombinant antibodies (U.S. Pat. Nos. 4,946,778, 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., Bio/Technology 10:779-783 (1992); Lonberg et al., Nature 368:856-859 (1994); Morrison, Nature 368:812-13 (1994); Fishwild et al., Nature Biotechnology 14:845-51 (1996); Neuberger, Nature Biotechnology 14:826 (1996); and Lonberg & Huszar, Intern. Rev. Immunol. 13:65-93 (1995)). Alternatively, phage display technology can be used to identify antibodies and heteromeric Fab fragments that specifically bind to selected antigens (see, e.g., McCafferty et al., Nature 348:552-554 (1990); Marks et al., Biotechnology 10:779-783 (1992)). Antibodies can also be made bispecific, i.e., able to recognize two different antigens (see, e.g., WO 93/08829, Traunecker et al., EMBO J. 10:3655-3659 (1991); and Suresh et al., Methods in Enzymology 121:210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Methods for humanizing or primatizing non-human antibodies are well known in the art (e.g., U.S. Pat. Nos. 4,816,567; 5,530,101; 5,859,205; 5,585,089; 5,693,761; 5,693,762; 5,777,085; 6,180,370; 6,210,671; and 6,329,511; WO 87/02671; EP Patent Application 0173494; Jones et al. (1986) Nature 321:522; and Verhoyen et al. (1988) Science 239:1534). Humanized antibodies are further described in, e.g., Winter and Milstein (1991) Nature 349:293. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Morrison et al., PNAS USA, 81:6851-6855 (1984), Jones et al., Nature 321:522-525 (1986); Riechmann et al., Nature 332:323-327 (1988); Morrison and Oi, Adv. Immunol., 44:65-92 (1988), Verhoeyen et al., Science 239:1534-1536 (1988) and Presta, Curr. Op. Struct. Biol. 2:593-596 (1992), Padlan, Molec. Immun., 28:489-498 (1991); Padlan, Molec. Immun., 31(3):169-217 (1994)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies. For example, polynucleotides comprising a first sequence coding for humanized immunoglobulin framework regions and a second sequence set coding for the desired immunoglobulin complementarity determining regions can be produced synthetically or by combining appropriate cDNA and genomic DNA segments. Human constant region DNA sequences can be isolated in accordance with well known procedures from a variety of human cells.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. The preferred antibodies of, and for use according to the invention include humanized and/or chimeric monoclonal antibodies.

Techniques for conjugating therapeutic agents to antibodies are well known (see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery" in Controlled Drug Delivery ($2^{nd}$ Ed.), Robinson et al. (eds.), pp. 623-53 (Marcel Dekker, Inc. 1987); Thorpe, "Antibody Carriers Of Cytotoxic Agents In Cancer Therapy: A Review" in Monoclonal Antibodies '84: Biological And Clinical Applications, Pinchera et al. (eds.), pp. 475-506 (1985); and Thorpe et al., "The Preparation And Cytotoxic Properties Of Antibody-Toxin Conjugates", Immunol. Rev., 62:119-58 (1982)). As used herein, the term "antibody-drug conjugate" or "ADC" refers to a therapeutic agent conjugated or otherwise covalently bound to to an antibody. A "therapeutic agent" as referred to herein, is a composition useful in treating or preventing a disease such as cancer.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies can be selected to obtain only a subset of antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998) for a description of immunoassay formats and conditions that can be used to determine specific immunoreactivity).

A "ligand" refers to an agent, e.g., a polypeptide or other molecule, capable of binding to a receptor.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be, for example, a pharmaceutical composition as provided herein and a cell. In embodiments contacting includes, for example, allowing a pharmaceutical composition as described herein to interact with a cell or a patient.

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, N.Y. 1994); Sambrook et al., MOLECULAR CLONING, A LABORATORY MANUAL, Cold Springs Harbor Press (Cold Springs Harbor, N.Y. 1989). Any methods, devices and materials similar or equivalent to those described herein can be used in the practice of this invention. The following definitions are provided to facilitate understanding of certain terms used frequently herein and are not meant to limit the scope of the present disclosure.

"Nucleic acid" refers to deoxyribonucleotides or ribonucleotides and polymers thereof in either single- or double-stranded form, and complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA (including siRNA), and hybrid molecules having mixtures of single and double stranded DNA and RNA. Nucleic acid as used herein also refers to nucleic acids that have the same basic chemical structure as a naturally occurring nucleic acid. Such analogues have modified sugars and/or modified ring substituents, but retain the same basic chemical structure as the naturally occurring nucleic acid. A nucleic acid mimetic refers to chemical compounds that have a structure that is different from the general chemical structure of a nucleic acid, but that functions in a manner similar to a naturally occurring nucleic acid. Examples of such analogues include, without limitation, phosphorothiolates, phosphoramidates, methyl phosphonates, chiral-methyl phosphonates, 2-O-methyl ribonucleotides, and peptide-nucleic acids (PNAs).

The terms "polypeptide," "peptide" and "protein" are used interchangeably herein to refer to a polymer of amino acid residues, wherein the polymer may In embodiments be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. A "fusion protein" refers to a chimeric protein encoding two or more separate protein sequences that are recombinantly expressed as a single moiety.

The term "peptidyl" and "peptidyl moiety" means a monovalent peptide.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, "conservatively modified variants" refers to those nucleic acids that encode identical or essentially identical amino acid sequences. Because of the degeneracy of the genetic code, a number of nucleic acid sequences will encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, *Proteins* (1984)).

The terms "numbered with reference to" or "corresponding to," when used in the context of the numbering of a given amino acid or polynucleotide sequence, refer to the numbering of the residues of a specified reference sequence when the given amino acid or polynucleotide sequence is compared to the reference sequence. An amino acid residue in a protein "corresponds" to a given residue when it occupies the same essential structural position within the protein as the given residue. One skilled in the art will immediately recognize the identity and location of residues corresponding to a specific position in a protein (e.g., ROR-1) in other proteins with different numbering systems. For example, by performing a simple sequence alignment with a protein (e.g., ROR-1) the identity and location of residues corresponding to specific positions of said protein are identified in other protein sequences aligning to said protein. For example, a selected residue in a selected protein corresponds to glutamic acid at position 138 when the selected residue occupies the same essential spatial or other structural relationship as a glutamic acid at position 138. In some embodiments, where a selected protein is aligned for maximum homology with a protein, the position in the aligned selected protein aligning with glutamic acid 138 is said to correspond to glutamic acid 138. Instead of a primary sequence alignment, a three dimensional structural alignment can also be used, e.g., where the structure of the selected protein is aligned for maximum correspondence with the glutamic acid at position 138, and the overall structures compared. In this case, an amino acid that occupies the same essential position as glutamic acid 138 in the structural model is said to correspond to the glutamic acid 138 residue.

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, optionally 65%, 70%, 75%, 80%, 85%, 90%, 95%, 98%, or 99% identity over a specified region, e.g., of the entire polypeptide sequences of the invention or individual domains of the polypeptides of the invention), when compared and aligned for maximum correspondence over a comparison window, or designated region as measured using one of the following sequence comparison algorithms or by manual alignment and visual inspection. Such sequences are then said to be "substantially identical." This definition also refers to the complement of a test sequence. Optionally, the identity exists over a region that is at least about 50 nucleotides in length, or more preferably over a region that is 100 to 500 or 1000 or more nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of, e.g., a full length sequence or from 20 to 600, about 50 to about 200, or about 100 to about 150 amino acids or nucleotides in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

An example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information (website at ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) or 10, M=5, N=−4 and a comparison of both strands. For amino acid sequences, the BLASTP program uses as defaults a word length of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The term "isolated," when applied to a protein, denotes that the protein is essentially free of other cellular components with which it is associated in the natural state. It is preferably in a homogeneous state although it can be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified. The term "purified" denotes that a protein gives rise to essentially one band in an electrophoretic gel. Particularly, it means that the protein is at least 85% pure, more preferably at least 95% pure, and most preferably at least 99% pure.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Typically a specific or selective reaction will be at least twice background signal or noise and more typically more than 10 to 100 times background.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include but are not limited to yeast cells and cells derived from plants and animals, for example mammalian, insect (e.g., spodoptera) and human cells.

As defined herein, the term "inhibition", "inhibit", "inhibiting" and the like in reference to a protein-inhibitor (e.g., an receptor antagonist or a signaling pathway inhibitor) interaction means negatively affecting (e.g., decreasing) the activity or function of the protein (e.g., decreasing the activity of a receptor or a protein) relative to the activity or function of the protein in the absence of the inhibitor. In some embodiments, inhibition refers to reduction of a disease or symptoms of disease (e.g., cancer). Thus, inhibition includes, at least in part, partially or totally blocking stimulation, decreasing, preventing, or delaying activation, or inactivating, desensitizing, or down-regulating signal transduction or enzymatic activity or the amount of a protein (e.g., a receptor). Similarly an "inhibitor" is a compound or protein that inhibits a receptor or another protein, e.g., by binding, partially or totally blocking, decreasing, preventing, delaying, inactivating, desensitizing, or down-regulating activity (e.g., a receptor activity or a protein activity).

The term "BTK antagonist" as provided herein refers to a substance capable of inhibiting BTK activity compared to a control. The inhibited activity of BTK can be 10%, 20%, 30%, 40%, 50%, 60%, 70%, 80%, 90% or less than that in a control. In certain instances, the inhibition is 1.5-fold, 2-fold, 3-fold, 4-fold, 5-fold, 10-fold, or more in comparison to a control. A BTK antagonist inhibits BTK activity e.g., by at least in part, partially or totally blocking stimulation, decreasing, preventing, or delaying activation, or inactivating, desensitizing, or down-regulating signal transduction, activity or amount of BTK relative to the absence of the BTK antagonist.

The term "ROR-1 antagonist" as provided herein refers to a substance capable of inhibiting ROR-1 activity compared to a control. The inhibited activity of ROR-1 can be 10%, 20%, 30%, 40%, 50%, 60%, 70%, 80%, 90% or less than that in a control. In certain instances, the inhibition is 1.5-fold, 2-fold, 3-fold, 4-fold, 5-fold, 10-fold, or more in comparison to a control. A ROR-1 antagonist inhibits ROR-1 activity e.g., by at least in part, partially or totally blocking stimulation, decreasing, preventing, or delaying activation, or inactivating, desensitizing, or down-regulating signal transduction, activity or amount of ROR-1 relative to the absence of the ROR-1 antagonist. In embodiments, the ROR-1 antagonist is an antibody or small molecule.

The term "antagonist" may alternatively be used herein as inhibitor.

By "therapeutically effective dose or amount" as used herein is meant a dose that produces effects for which it is administered (e.g. treating or preventing a disease). The exact dose and formulation will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Remington: The Science and Practice of Pharmacy, 20th Edition, Gennaro, Editor (2003), and Pickar, Dosage Calculations (1999)). For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a standard control. A therapeutically effective dose or amount may ameliorate one or more symptoms of a disease. A therapeutically effective dose or amount may prevent or delay the onset of a disease or one or more symptoms of a disease when the effect for which it is being administered is to treat a person who is at risk of developing the disease.

"Anti-cancer agent" is used in accordance with its plain ordinary meaning and refers to a composition (e.g., compound, drug, antagonist, inhibitor, modulator) having antineoplastic properties or the ability to inhibit the growth or proliferation of cells. In some embodiments, an anti-cancer agent is a chemotherapeutic. In some embodiments, an anti-cancer agent is an agent identified herein having utility in methods of treating cancer. In some embodiments, an anti-cancer agent is an agent approved by the FDA or similar regulatory agency of a country other than the USA, for treating cancer. Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethlymelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds or platinum containing agents (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin I1 (including recombinant interleukin II, or rIL.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol™ (i.e. paclitaxel), Taxotere™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), Vincristine sulfate, Cryptophycin 52 (i.e. LY-355703), Vitilevuamide, Tubulysin A, Canadensol, Centaureidin (i.e. NSC-106969), Oncocidin Al (i.e. BTO-956 and DIME), Fijianolide B, Laulimalide, Narcosine (also known as NSC-5366), Nascapine, Hemiasterlin, Vanadocene acetylacetonate, Monsatrol, lnanocine (i.e. NSC-698666), Eleutherobins (such as Desmethyleleutherobin, Desaetyleleutherobin, Isoeleutherobin A, and Z-Eleutherobin), Caribaeoside, Caribaeolin, Halichondrin B, Diazonamide A, Taccalonolide A, Diozostatin, (−)-Phenylahistin (i.e. NSCL-96F037), Myoseverin B, Resverastatin phosphate sodium, steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., Bacillus Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), radioimmunotherapy (e.g., anti-CD20 monoclonal antibody conjugated to $^{111}$In $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™) afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, hormonal therapies, or the like.

The term "ibrutinib," also known as Imbruvica®, PCI 32765 or the like, refers in the usual and customary sense, to 1-[(3R)-3-[4-Amino-3-(4-phenoxyphenyl)-1H-pyrazolo[3,4-d]pyrimidin-1-yl]piperidin-1-yl]prop-2-en-1-one (CAS Registry number 936563-96-1). In embodiments, the BTK antagonist is any one of the compounds disclosed in U.S. Pat. Nos. 7,514,444, 8,008,309; 8,497,277; 8,476,284; 8,697,711, and 8,703,780 which are incorporated by reference herein in their entirety and for all purposes.

The term "idelalisib," also known as CAL101, GS-1101, Zydelig® or the like, refers in the usual and customary sense to 5-Fluoro-3-phenyl-2-[(15)-1-(7H-purin-6-ylamino)propyl]-4(3H)-quinazolinone (CAS Registry number 870281-82-6). In embodiments, the BTK antagonist is any one of the compounds disclosed in U.S. Pat. Nos. 9,469,643; 9,492,449; 8,139,195; 8,492,389; 8,865,730; and 9,149,477 which are incorporated by reference herein in their entirety and for all purposes.

The term "R406" or the like refers, in the usual and customary sense, to 6-((5-fluoro-2-((3,4,5-trimethoxyphenyl)amino)pyrimidin-4-yl)amino)-2,2-dimethyl-2H-pyrido[3,2-b][1,4]oxazin-3(4H)-one benzenesulfonate.

The term "fostamatinib" or the like refers in the usual and customary sense, to 6-((5-fluoro-2-((3,4,5-trimethoxyphenyl)amino)pyrimidin-4-yl)amino)-2,2-dimethyl-2H-pyrido[3,2-b][1,4]oxazin-3(4H)-one benzenesulfonate (CAS Registry number 901119-35-5 or 1025687-58-4 (disodium salt)). Fostamatinib is a prodrug of R406. In embodiments, the BTK antagonist is any one of the compounds disclosed in U.S. Pat. No. 7,449,458 which is incorporated by reference herein in its entirety and for all purposes.

The term "acalabrutinib," also known as ACP-196 or the like, refers in the usual and customary sense to 4-[8-amino-3-[(2S)-1-but-2-ynoylpyrrolidin-2-yl]imidazo[1,5-a]pyrazin-1-yl]-N-pyridin-2-ylbenzamide (CAS Registry number 1420477-60-6). In embodiments, the BTK antagonist is any one of the compounds disclosed in US Patent Application Nos. 20140155385, 20160151364, 20160159810 which are incorporated by reference herein in their entirety and for all purposes.

The term "ONO/GS-4059" or the like, refers in the usual and customary sense to 6-amino-7-(4-phenoxyphenyl)-9-[(3S)-1-prop-2-enoylpiperidin-3-yl]purin-8-one (CAS Registry number 1351636-18-4). In embodiments, the BTK antagonist is any one of the compounds disclosed in U.S. Pat. Nos. 8,940,725 and 8,557,803 and US Patent Application No. 20150094299 which are incorporated by reference herein in their entirety and for all purposes.

The term "BGB-3111" or the like, refers in the usual and customary sense to 2-(4-phenoxyphenyl)-7-(1-prop-2-enoylpiperidin-4-yl)-1,5,6,7-tetrahydropyrazolo[1,5-a]pyrimidine-3-carboxamide (CAS Registry number 1633350-06-7). In embodiments, the BTK antagonist is any one of the compounds disclosed in US Patent Application Nos. 20150259354 and 20160083392 which are incorporated by reference herein in their entirety and for all purposes.

The term "CC-292," also known as AVL-292, spebrutinib or the like, refers in the usual and customary sense to N-[3-[[5-fluoro-2-[4-(2-methoxyethoxy)anilino]pyrimidin-4-yl]amino]phenyl]prop-2-enamide (CAS Registry number 1202757-89-8). In embodiments, the BTK antagonist is any one of the compounds disclosed in U.S. Pat. No. 8,338,439 which is incorporated by reference herein in its entirety and for all purposes.

The terms "cirmtuzumab", "UC-961", and "99961.1" refer to a humanized monoclonal antibody capable of binding the extracellular domain of the human receptor tyrosine kinase-like orphan receptor 1 (ROR-1). In embodiments, cirmtuzumab is any one of the antibodies or fragments thereof disclosed in U.S. patent application Ser. No. 14/422,519, which is incorporated by reference herein in its entirety and for all purposes.

As used herein, the term "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about means the specified value.

The terms "disease" or "condition" refer to a state of being or health status of a patient or subject capable of being treated with a compound, pharmaceutical composition, or method provided herein. In embodiments, the disease is cancer (e.g. lung cancer, ovarian cancer, osteosarcoma, bladder cancer, cervical cancer, liver cancer, kidney cancer, skin cancer (e.g., Merkel cell carcinoma), testicular cancer, leukemia, lymphoma, head and neck cancer, colorectal cancer, prostate cancer, pancreatic cancer, melanoma, breast cancer, neuroblastoma). The disease may be an autoimmune, inflammatory, cancer, infectious, metabolic, developmental, cardiovascular, liver, intestinal, endocrine, neurological, or other disease.

As used herein, the term "cancer" refers to all types of cancer, neoplasm or malignant tumors found in mammals, including leukemias, lymphomas, melanomas, neuroendocrine tumors, carcinomas and sarcomas. Exemplary cancers that may be treated with a compound, pharmaceutical composition, or method provided herein include lymphoma, sarcoma, bladder cancer, bone cancer, brain tumor, cervical cancer, colon cancer, esophageal cancer, gastric cancer, head and neck cancer, kidney cancer, myeloma, thyroid cancer, leukemia, prostate cancer, breast cancer (e.g. triple negative, ER positive, ER negative, chemotherapy resistant, herceptin resistant, HER$^2$ positive, doxorubicin resistant, tamoxifen resistant, ductal carcinoma, lobular carcinoma, primary, metastatic), ovarian cancer, pancreatic cancer, liver cancer (e.g., hepatocellular carcinoma), lung cancer (e.g. non-small cell lung carcinoma, squamous cell lung carcinoma, adenocarcinoma, large cell lung carcinoma, small cell lung carcinoma, carcinoid, sarcoma), glioblastoma multiforme, glioma, melanoma, prostate cancer, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma. Additional examples include, cancer of the thyroid, endocrine system, brain, breast, cervix, colon, head & neck, esophagus, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound, pharmaceutical composition, or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, aleukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound, pharmaceutical composition, or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound, pharmaceutical composition, or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound, pharmaceutical composition, or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, ductal carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lobular carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossifi cans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tubular carcinoma, tuberous carcinoma, verrucous carcinoma, or carcinoma villosum.

As used herein, the terms "metastasis," "metastatic," and "metastatic cancer" can be used interchangeably and refer to the spread of a proliferative disease or disorder, e.g., cancer, from one organ or another non-adjacent organ or body part. Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

The term "associated" or "associated with" in the context of a substance or substance activity or function associated with a disease (e.g., diabetes, cancer (e.g. prostate cancer, renal cancer, metastatic cancer, melanoma, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma)) means that the disease (e.g. lung cancer, ovarian cancer, osteosarcoma, bladder cancer, cervical cancer, liver cancer, kidney cancer, skin cancer (e.g., Merkel cell carcinoma), testicular cancer, leukemia, lymphoma, head and neck cancer, colorectal cancer, prostate cancer, pancreatic cancer, melanoma, breast cancer, neuroblastoma) is caused by (in whole or in part), or a symptom of the disease is caused by (in whole or in part) the substance or substance activity or function.

"Patient" or "subject in need thereof" refers to a living organism suffering from or prone to a disease or condition that can be treated by administration of a composition or pharmaceutical composition as provided herein. Non-limiting examples include humans, other mammals, bovines, rats, mice, dogs, monkeys, goat, sheep, cows, deer, and other non-mammalian animals. In some embodiments, a patient is human.

Methods

The methods provided herein are, inter alia, useful for the treatment of cancer. In embodiments, the methods and compositions as described herein provide effective treatment for cancers expressing ROR-1. In an aspect is provided a method of treating cancer in a subject in need thereof, the method including administering to the subject a therapeutically effective amount of a Bruton's tyrosine kinase (BTK) antagonist and a tyrosine kinase-like orphan receptor 1 (ROR-1) antagonist.

In another aspect, there is provided a method of treating cancer in a subject in need thereof. The method includes administering to the subject a therapeutically effective amount of a Bruton's tyrosine kinase (BTK) antagonist and an anti-ROR-1 antibody.

The term "Bruton's tyrosine kinase," also known as tyrosine-protein kinase BTK, as used herein refers to the any of the recombinant or naturally-occurring forms of Bruton's tyrosine kinase (BTK) or variants or homologs thereof that maintain BTK activity (e.g., within at least 50%, 80%, 90%, 95%, 96%, 97%, 98%, 99% or 100% activity compared to BTK). In some aspects, the variants or homologs have at least 90%, 95%, 96%, 97%, 98%, 99% or 100% amino acid sequence identity across the whole sequence or a portion of the sequence (e.g., a 50, 100, 150 or 200 continuous amino acid portion) compared to a naturally occurring BTK protein. In embodiments, the BTK protein is substantially identical to the protein identified by the UniProt reference number Q01687 or a variant or homolog having substantial identity thereto.

In embodiments, the BTK antagonist is a small molecule. In embodiments, the BTK antagonist is ibrutinib, idelalisib, fostamatinib, acalabrutinib, ONO/GS-4059, BGB-3111 or CC-292 (AVL-292). In embodiments, the BTK antagonist is ibrutinib. In embodiments, the BTK antagonist is idelalisib. In embodiments, the BTK antagonist is fostamatinib. In embodiments, the BTK antagonist is acalabrutinib. In embodiments, the BTK antagonist is ONO/GS-4059. In embodiments, the BTK antagonist is BGB-3111. In embodiments, the BTK antagonist is CC-292 (AVL-292). In embodiments, the BTK antagonist is R406.

The term "ROR-1" as used herein refers to the any of the recombinant or naturally-occurring forms of tyrosine kinase-like orphan receptor 1 (ROR-1) or variants or homologs thereof that maintain ROR-1 activity (e.g., within at least 50%, 80%, 90%, 95%, 96%, 97%, 98%, 99% or 100% activity compared to ROR-1). In some aspects, the variants or homologs have at least 90%, 95%, 96%, 97%, 98%, 99% or 100% amino acid sequence identity across the whole sequence or a portion of the sequence (e.g., a 50, 100, 150 or 200 continuous amino acid portion) compared to a naturally occurring ROR-1 protein. In embodiments, the ROR-1 protein is substantially identical to the protein identified by Accession No. NP 005003.1 or a variant or homolog having substantial identity thereto. In embodiments, the ROR-1 protein includes the amino acid sequence of SEQ ID NO:13. In embodiments, the ROR-1 protein is the amino acid sequence of SEQ ID NO:13. In embodiments, the ROR-1 protein includes the amino acid sequence of SEQ ID NO:14. In embodiments, the ROR-1 protein includes the amino acid sequence of SEQ ID NO:15.

In the instance where the ROR-1 antagonist is an antibody, the antibody specifically binds to a ROR-1 polypeptide. Thus, in embodiments, the ROR-1 antagonist is an anti-ROR-1 antibody. In embodiments, the anti-ROR-1 antibody is a humanized antibody.

The anti-ROR-1 antibody may include amino acid sequences (e.g., CDRs) allowing it to bind portions of a ROR-1 polypeptide or a fragment thereof. Therefore, in embodiments, the antibody includes a humanized heavy chain variable region and a humanized light chain variable region, wherein the humanized heavy chain variable region includes the sequences set forth in SEQ ID NO:1, SEQ ID NO:2, and SEQ ID NO:3; and wherein the humanized light chain variable region includes the sequences set forth in SEQ ID NO:4, SEQ ID NO:5, and SEQ ID NO:6.

In embodiments, the antibody is cirmtuzumab. Cirmtuzumab as defined herein is also referred to herein as UC-961 or 99961.1. The development and structure of cirmtuzumab is disclosed in U.S. patent application Ser. No. 14/422,519 which is incorporated by reference herein in its entirety and for all purposes.

In embodiments, the antibody includes a humanized heavy chain variable region and a humanized light chain variable region, wherein the humanized heavy chain variable region includes the sequences set forth in SEQ ID NO:7, SEQ ID NO:8, and SEQ ID NO:9; and wherein the humanized light chain variable region includes the sequences set forth in SEQ ID NO:10, SEQ ID NO:11, and SEQ ID NO:12. An antibody including the amino acid sequences (i.e., CDRs) set forth by SEQ ID NOs:7, 8, 9, 10, 11, 12 may be referred to herein as antibody D10. The development and use of antibody D10 is disclosed in U.S. Pat. No. 9,217,040 which is incorporated by reference herein in its entirety and for all purposes.

In embodiments, the antibody binds to amino acids 130-160 of ROR-1 or a fragment thereof. In embodiments, the antibody binds a peptide including a glutamic acid at a position corresponding to position 138 of ROR-1. In embodiments, the antibody specifically binds either the 3' or middle Ig-like region of the extracellular domain of the ROR-1 protein. In embodiments, the antibody binds the 3' end of the Ig-like region of the extracellular domain of ROR-1 protein from position 1-147.

In embodiments, the antibody inhibits metastasis. In embodiments, the antibody is an antibody fragment. In embodiments, the antibody is human. In embodiments, the antibody is humanized. In embodiments, the antibody is a chimeric antibody. In embodiments, the antibody is a single chain antibody.

In embodiments, the antibody has a binding affinity of about 500 pM to about 6 nM. In embodiments, the antibody has a binding affinity of about 550 pM to about 6 nM. In embodiments, the antibody has a binding affinity of about 600 pM to about 6 nM. In embodiments, the antibody has a binding affinity of about 650 pM to about 6 nM. In embodiments, the antibody has a binding affinity of about 700 pM to about 6 nM. In embodiments, the antibody has a binding affinity of about 750 pM to about 6 nM. In embodiments, the antibody has a binding affinity of about 800 pM to about 6 nM. In embodiments, the antibody has a binding affinity of about 850 pM to about 6 nM. In embodiments, the antibody has a binding affinity of about 900 pM to about 6 nM. In embodiments, the antibody has a binding affinity of about 950 pM to about 6 nM. In embodiments, the antibody has a binding affinity of about 1 nM to about 6 nM. In embodiments, the antibody has a binding affinity of about 1 nM to about 6 nM. In embodiments, the antibody has a binding affinity of about 1.5 nM to about 6 nM. In embodiments, the antibody has a binding affinity of about 2 nM to about 6 nM. In embodiments, the antibody has a binding affinity of about 2.5 nM to about 6 nM. In embodiments, the antibody has a binding affinity of about 3 nM to about 6 nM. In embodiments, the antibody has a binding affinity of about 3.5 nM to about 6 nM. In embodiments, the antibody has a binding affinity of about 4 nM to about 6 nM. In embodiments, the antibody has a binding affinity of about 4.5 nM to about 6 nM. In embodiments, the antibody has a binding affinity of about 5 nM to about 6 nM. In embodiments, the antibody has a binding affinity of about 5.5 nM to about 6 nM.

In embodiments, the antibody has a binding affinity of 500 pM to 6 nM. In embodiments, the antibody has a binding affinity of 550 pM to 6 nM. In embodiments, the antibody has a binding affinity of 600 pM to 6 nM. In embodiments, the antibody has a binding affinity of 650 pM to 6 nM. In embodiments, the antibody has a binding affinity of 700 pM to 6 nM. In embodiments, the antibody has a binding affinity of 750 pM to 6 nM. In embodiments, the antibody has a binding affinity of 800 pM to 6 nM. In embodiments, the antibody has a binding affinity of 850 pM to 6 nM. In embodiments, the antibody has a binding affinity of 900 pM to 6 nM. In embodiments, the antibody has a binding affinity of 950 pM to 6 nM. In embodiments, the antibody has a binding affinity of 1 nM to 6 nM. In embodiments, the antibody has a binding affinity of 1 nM to 6 nM. In embodiments, the antibody has a binding affinity of 1.5 nM to 6 nM. In embodiments, the antibody has a binding affinity of 2 nM to 6 nM. In embodiments, the antibody has a binding affinity of 2.5 nM to 6 nM. In embodiments, the antibody has a binding affinity of 3 nM to 6 nM. In embodiments, the antibody has a binding affinity of 3.5 nM to 6 nM. In embodiments, the antibody has a binding affinity of 4 nM to 6 nM. In embodiments, the antibody has a binding affinity of 4.5 nM to 6 nM. In embodiments, the antibody has a binding affinity of 5 nM to 6 nM. In embodiments, the antibody has a binding affinity of 5.5 nM to 6 nM.

In embodiments, the antibody has a binding affinity of about 500 pM to about 5.5 nM. In embodiments, the antibody has a binding affinity of about 500 pM to about 5 nM. In embodiments, the antibody has a binding affinity of about 500 pM to about 4.5 nM. In embodiments, the antibody has a binding affinity of about 500 pM to about 4 nM. In embodiments, the antibody has a binding affinity of about 500 pM to about 3.5 nM. In embodiments, the antibody has a binding affinity of about 500 pM to about 3 nM. In embodiments, the antibody has a binding affinity of about 500 pM to about 3.5 nM. In embodiments, the antibody has a binding affinity of about 500 pM to about 3 nM. In embodiments, the antibody has a binding affinity of about 500 pM to about 2.5 nM. In embodiments, the antibody has a binding affinity of about 500 pM to about 2 nM. In embodiments, the antibody has a binding affinity of about 500 pM to about 1.5 nM. In embodiments, the antibody has a binding affinity of about 500 pM to about 1 nM. In embodiments, the antibody has a binding affinity of about 500 pM to about 950 pM. In embodiments, the antibody has a binding affinity of about 500 pM to about 900 pM. In embodiments, the antibody has a binding affinity of about 500 pM to about 850 pM. In embodiments, the antibody has a binding affinity of about 500 pM to about 800 pM. In embodiments, the antibody has a binding affinity of about 500 pM to about 750 pM. In embodiments, the antibody has a binding affinity of about 500 pM to about 700 pM. In embodiments, the antibody has a binding affinity of about 500 pM to about 650 pM. In embodiments, the antibody has a binding affinity of about 500 pM to about 600 pM. In embodiments, the antibody has a binding affinity of about 500 pM to about 550 pM.

In embodiments, the antibody has a binding affinity of 500 pM to 5.5 nM. In embodiments, the antibody has a binding affinity of 500 pM to 5 nM. In embodiments, the antibody has a binding affinity of 500 pM to 4.5 nM. In embodiments, the antibody has a binding affinity of 500 pM to 4 nM. In embodiments, the antibody has a binding affinity of 500 pM to 3.5 nM. In embodiments, the antibody has a binding affinity of 500 pM to 3 nM. In embodiments, the antibody has a binding affinity of 500 pM to 3.5 nM. In embodiments, the antibody has a binding affinity of 500 pM to 3 nM. In embodiments, the antibody has a binding affinity of 500 pM to 2.5 nM. In embodiments, the antibody has a binding affinity of 500 pM to 2 nM. In embodiments, the antibody has a binding affinity of 500 pM to 1.5 nM. In embodiments, the antibody has a binding affinity of 500 pM to 1 nM. In embodiments, the antibody has a binding affinity of 500 pM to 950 pM. In embodiments, the antibody has a binding affinity of 500 pM to 900 pM. In embodiments, the antibody has a binding affinity of 500 pM to 850 pM. In embodiments, the antibody has a binding affinity of 500 pM to 800 pM. In embodiments, the antibody has a binding affinity of 500 pM to 750 pM. In embodiments, the antibody has a binding affinity of 500 pM to 700 pM. In embodiments, the antibody has a binding affinity of 500 pM to 650 pM. In embodiments, the antibody has a binding affinity of 500 pM to 600 pM. In embodiments, the antibody has a binding affinity of 500 pM to 550 pM.

In embodiments, the antibody has a binding affinity of about 500 pM. In embodiments, the antibody has a binding affinity of 500 pM. In embodiments, the antibody has a binding affinity of about 550 pM. In embodiments, the antibody has a binding affinity of 550 pM. In embodiments, the antibody has a binding affinity of about 600 pM. In embodiments, the antibody has a binding affinity of 600 pM. In embodiments, the antibody has a binding affinity of about 650 pM. In embodiments, the antibody has a binding affinity of 650 pM. In embodiments, the antibody has a binding affinity of about 700 pM. In embodiments, the antibody has a binding affinity of 700 pM. In embodiments, the antibody has a binding affinity of about 750 pM. In embodiments, the antibody has a binding affinity of 750 pM. In embodiments, the antibody has a binding affinity of about 800 pM. In embodiments, the antibody has a binding affinity of 800 pM. In embodiments, the antibody has a binding affinity of about 850 pM. In embodiments, the antibody has a binding affinity of 850 pM. In embodiments, the antibody has a binding affinity of about 900 pM. In embodiments, the antibody has a binding affinity of 900 pM. In embodiments, the antibody has a binding affinity of about 950 pM. In embodiments, the antibody has a binding affinity of 950 pM. In embodiments, the antibody has a binding affinity of about 1 nM. In embodiments, the antibody has a binding affinity of about 1 nM. In embodiments, the antibody has a binding affinity of 1 nM. In embodiments, the antibody has a binding affinity of about 1.5 nM. In embodiments, the antibody has a binding affinity of 1.5 nM. In embodiments, the antibody has a binding affinity of about 2 nM. In embodiments, the antibody has a binding affinity of 2 nM. In embodiments, the antibody has a binding affinity of about 2.5 nM. In embodiments, the antibody has a binding affinity of 2.5 nM. In embodiments, the antibody has a binding affinity of about 3 nM. In embodiments, the antibody has a binding affinity of 3 nM. In embodiments, the antibody has a binding affinity of about 3.5 nM. In embodiments, the antibody has a binding affinity of 3.5 nM. In embodiments, the antibody has a binding affinity of about 4 nM. In embodiments, the antibody has a binding affinity of 4 nM. In embodiments, the antibody has a binding affinity of about 4.5 nM. In embodiments, the antibody has a binding affinity of 4.5 nM. In embodiments, the antibody has a binding affinity of about 5 nM. In embodiments, the antibody has a binding affinity of 5 nM. In embodiments, the antibody has a binding affinity of about 5.5 nM. In embodiments, the antibody has a binding affinity of 5.5 nM. In embodiments, the antibody has a binding affinity of about 6 nM. In embodiments, the antibody has a binding affinity of 6 nM.

In embodiments, the antibody binds to an ROR-1 protein with a $K_D$ of less than about 40 nM (e.g., 35, 30, 25, 20, 15, 10, 9, 8, 7, 6, 5, 4, 3, 2, 1, 0.5, 0.25, 0.1 nM). In embodiments, the antibody binds to an ROR-1 protein with a $K_D$ of less than 40 nM (e.g., 35, 30, 25, 20, 15, 10, 9, 8, 7, 6, 5, 4, 3, 2, 1, 0.5, 0.25, 0.1 nM). In embodiments, the antibody binds to an ROR-1 protein with a $K_D$ of less than about 35 nM. In embodiments, the antibody binds to an ROR-1 protein with a $K_D$ of less than 35 nM. In embodiments, the antibody binds to an ROR-1 protein with a $K_D$ of less than about 30 nM. In embodiments, the antibody binds to an ROR-1 protein with a $K_D$ of less than 30 nM. In embodiments, the antibody binds to an ROR-1 protein with a $K_D$ of less than about 25 nM. In embodiments, the antibody binds to an ROR-1 protein with a $K_D$ of less than 25 nM. In embodiments, the antibody binds to an ROR-1 protein with a $K_D$ of less than about 20 nM. In embodiments, the antibody binds to an ROR-1 protein with a $K_D$ of less than 20 nM. In embodiments, the antibody binds to an ROR-1 protein with a $K_D$ of less than about 15 nM. In embodiments, the antibody binds to an ROR-1 protein with a $K_D$ of less than 15 nM. In embodiments, the antibody binds to an ROR-1 protein with a $K_D$ of less than about 10 nM. In embodiments, the antibody binds to an ROR-1 protein with a $K_D$ of less than 10 nM. In embodiments, the antibody binds to an ROR-1 protein with a $K_D$ of less than about 9 nM. In embodiments, the antibody binds to an ROR-1 protein with a $K_D$ of less than 9 nM. In embodiments, the antibody binds to an ROR-1 protein with a $K_D$ of less than about 8 nM. In embodiments, the antibody binds to an ROR-1 protein with a $K_D$ of less than 8 nM. In embodiments, the antibody binds to an ROR-1 protein with a $K_D$ of less than about 7 nM. In embodiments, the antibody binds to an ROR-1 protein with a $K_D$ of less than 7 nM. In embodiments, the antibody binds to an ROR-1 protein with a $K_D$ of less than about 6 nM. In embodiments, the antibody binds to an ROR-1 protein with a $K_D$ of less than 6 nM. In embodiments, the antibody binds to an ROR-1 protein with a $K_D$ of less than about 5 nM. In embodiments, the antibody binds to an ROR-1 protein with a $K_D$ of less than 5 nM. In embodiments, the antibody binds to an ROR-1 protein with a $K_D$ of less than about 4 nM. In embodiments, the antibody binds to an ROR-1 protein with a $K_D$ of less than 4 nM. In embodiments, the antibody binds to an ROR-1 protein with a $K_D$ of less than about 3 nM. In embodiments, the antibody binds to an ROR-1 protein with a $K_D$ of less than 3 nM. In embodiments, the antibody binds to an ROR-1 protein with a $K_D$ of less than about 2 nM. In embodiments, the antibody binds to an ROR-1 protein with a $K_D$ of less than 2 nM. In embodiments, the antibody binds to an ROR-1 protein with a $K_D$ of less than about 1 nM. In embodiments, the antibody binds to an ROR-1 protein with a $K_D$ of less than 1 nM. In embodiments, the antibody binds to an ROR-1 protein with a $K_D$ of less than about 0.5 nM. In embodiments, the antibody binds to an ROR-1 protein with a $K_D$ of less than 0.5 nM. In embodiments, the antibody binds to an ROR-1 protein with a $K_D$ of less than about 0.25 nM. In embodiments, the antibody binds to an ROR-1 protein with a $K_D$ of less than 0.25 nM. In embodiments, the antibody binds to an ROR-1 protein with a $K_D$ of less than about 0.1 nM. In embodiments, the antibody binds to an ROR-1 protein with a $K_D$ of less than 0.1 nM.

In embodiments, the antibody is cirmtuzumab, also referred to herein as 99961.1 or UC-961. In embodiments, the antibody is D10.

In embodiments, the BTK antagonist and the ROR-1 antagonist are administered in a combined synergistic amount. In embodiments, the BTK antagonist and anti-ROR-1 antibody are administered in a combined synergistic amount. A "combined synergistic amount" as used herein refers to the sum of a first amount (e.g., an amount of a BTK antagonist) and a second amount (e.g., an amount of a ROR-1 antagonist) that results in a synergistic effect (i.e. an effect greater than an additive effect). Therefore, the terms "synergy", "synergism", "synergistic", "combined synergistic amount", and "synergistic therapeutic effect" which are used herein interchangeably, refer to a measured effect of compounds administered in combination where the measured effect is greater than the sum of the individual effects of each of the compounds administered alone as a single agent.

In embodiments, a synergistic amount may be about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of the amount of the BTK antagonist when used separately from the ROR-1 antagonist. In embodiments, a synergistic amount may be about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of the amount of the ROR-1 antagonist when used separately from the BTK antagonist.

The synergistic effect may be a BTK activity decreasing effect and/or a ROR-1 activity decreasing effect. In embodiments, synergy between the BTK antagonist and the ROR-1 antagonist may result in about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% greater decrease (e.g., decrease of BTK activity or decrease of ROR-1 activity) than the sum of the decrease of the BTK antagonist or the ROR-1 antagonist when used individually and separately. In embodiments, synergy between the BTK antagonist and the ROR-1 antagonist may result in 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% greater inhibition of the BTK protein and/or the ROR-1 protein than the sum of the inhibition of the BTK antagonist or the ROR-1 antagonist when used individually and separately.

The synergistic effect may be a cancer-treating effect such as a lymphoma (i.e. a lymphoma-treating synergistic effect), leukemia (i.e. a leukemia-treating synergistic effect), myeloma (i.e. a myeloma-treating synergistic effect), AML (i.e. a AML-treating synergistic effect), B-ALL (i.e. a B-ALL-treating synergistic effect), T-ALL (i.e. a T-ALL-treating synergistic effect), renal cell carcinoma (i.e. a renal cell carcinoma-treating synergistic effect), colon cancer (i.e. a colon cancer-treating synergistic effect), colorectal cancer (i.e. a colorectal cancer-treating synergistic effect), breast cancer (i.e. a breast cancer-treating synergistic effect), epithelial squamous cell cancer (i.e., epithelial squamous cell cancer-treating synergistic effect), melanoma (i.e., melanoma-treating synergistic effect), stomach cancer (i.e. a stomach cancer-treating synergistic effect), brain cancer (i.e. a brain cancer-treating synergistic effect), lung cancer (i.e. a lung cancer-treating synergistic effect), pancreatic cancer (i.e. a pancreatic cancer-treating synergistic effect), cervical cancer (i.e. a cervical cancer-treating synergistic effect), ovarian cancer (i.e. an ovarian cancer-treating synergistic effect), liver cancer (i.e. a liver cancer-treating synergistic effect), bladder cancer (i.e. a bladder cancer-treating synergistic effect), prostate cancer (i.e. a prostate cancer-treating synergistic effect), testicular cancer (i.e. a testicular cancer-treating synergistic effect), thyroid cancer (i.e. a thyroid cancer-treating synergistic effect), head and neck cancer (i.e. a head and neck cancer-treating synergistic effect), uterine cancer (i.e. an uterine cancer-treating synergistic effect), adenocarcinoma (i.e. an adenocarcinoma-treating synergistic effect), adrenal cancer (i.e. a adrenal cancer-treating synergistic effect), chronic lymphocytic leukemia (i.e. a chronic lymphocytic leukemia-treating synergistic effect), small lymphocytic lymphoma (i.e. a small lymphocytic lymphoma-treating synergistic effect), marginal cell B-Cell lymphoma (i.e. a marginal cell B-Cell lymphoma-treating synergistic effect), Burkitt's Lymphoma (i.e. a Burkitt's Lymphoma-treating synergistic effect), and B cell leukemia (i.e. a B cell leukemia-treating synergistic effect) treating effect.

The BTK antagonist and the ROR-1 antagonist may be administered in combination either simultaneously (e.g., as a mixture), separately but simultaneously (e.g., via separate intravenous lines) or sequentially (e.g., one agent is administered first followed by administration of the second agent). Thus, the term combination is used to refer to concomitant, simultaneous or sequential administration of the BTK antagonist and the ROR-1 antagonist.

In embodiments, the BTK antagonist and the ROR-1 antagonist are administered simultaneously or sequentially. In embodiments, the BTK antagonist and the ROR-1 antagonist are administered simultaneously. In embodiments, the BTK antagonist and the ROR-1 antagonist are administered sequentially. During the course of treatment the BTK antagonist and ROR-1 antagonist may at times be administered sequentially and at other times be administered simultaneously.

In embodiments, where the BTK antagonist and the ROR-1 antagonist are administered sequentially, the ROR-1 antagonist is administered at a first time point and the BTK antagonist is administered at a second time point, wherein the first time point precedes the second time point. Alternatively, in embodiments, where the BTK antagonist and the ROR-1 antagonist are administered sequentially, the BTK antagonist is administered at a first time point and the ROR-1 antagonist is administered at a second time point, wherein the first time point precedes the second time point.

In embodiments, the BTK antagonist and the anti-ROR-1 antibody are administered simultaneously or sequentially. In embodiments, the BTK antagonist and the anti-ROR-1 antibody are administered simultaneously. In embodiments, the BTK antagonist and the anti-ROR-1 antibody are administered sequentially. During the course of treatment the BTK antagonist and anti-ROR-1 antibody may at times be administered sequentially and at other times be administered simultaneously.

In embodiments, where the BTK antagonist and the anti-ROR-1 antibody are administered sequentially, the anti-ROR-1 antibody is administered at a first time point and the BTK antagonist is administered at a second time point, wherein the first time point precedes the second time point. Alternatively, in embodiments, where the BTK antagonist and the anti-ROR-1 antibody are administered sequentially, the BTK antagonist is administered at a first time point and the anti-ROR-1 antibody is administered at a second time point, wherein the first time point precedes the second time point.

The course of treatment is best determined on an individual basis depending on the particular characteristics of the subject and the type of treatment selected. The treatment, such as those disclosed herein, can be administered to the subject on a daily, twice daily, bi-weekly, monthly or any applicable basis that is therapeutically effective. The treatment can be administered alone or in combination with any other treatment disclosed herein or known in the art. The additional treatment can be administered simultaneously with the first treatment, at a different time, or on an entirely different therapeutic schedule (e.g., the first treatment can be daily, while the additional treatment is weekly).

In instances where the BTK antagonist and ROR-1 antagonist are administered simultaneously, the BTK antagonist and ROR-1 antagonist may be administered as a mixture. Thus, in embodiments, the BTK antagonist and the ROR-1 antagonist are admixed prior to administration.

In embodiments, the BTK antagonist is administered at an amount of about 1 mg/kg, 2 mg/kg, 5 mg/kg, 10 mg/kg or 15 mg/kg. In embodiments, the BTK antagonist is administered at an amount of about 1 mg/kg. In embodiments, the BTK antagonist is administered at an amount of 1 mg/kg. In embodiments, the BTK antagonist is administered at an amount of about 2 mg/kg. In embodiments, the BTK antagonist is administered at an amount of 2 mg/kg. In embodiments, the BTK antagonist is administered at an amount of about 5 mg/kg. In embodiments, the BTK antagonist is administered at an amount of 5 mg/kg. In embodiments, the BTK antagonist is administered at an amount of about 10 mg/kg. In embodiments, the BTK antagonist is administered at an amount of 10 mg/kg. In embodiments, the BTK antagonist is administered at an amount of about 15 mg/kg. In embodiments, the BTK antagonist is administered at an amount of 15 mg/kg. In embodiments, the BTK antagonist is administered at an amount of about 420 mg. In embodiments, the BTK antagonist is administered at an amount of 420 mg.

In embodiments, the ROR-1 antagonist is administered at an amount of about 1 mg/kg, 2 mg/kg, 3 mg/kg, 5 mg/kg or 10 mg/kg. In embodiments, the ROR-1 antagonist is administered at an amount of about 1 mg/kg. In embodiments, the ROR-1 antagonist is administered at an amount of 1 mg/kg. In embodiments, the ROR-1 antagonist is administered at an amount of about 2 mg/kg. In embodiments, the ROR-1 antagonist is administered at an amount of 2 mg/kg. In embodiments, the ROR-1 antagonist is administered at an amount of about 3 mg/kg. In embodiments, the ROR-1 antagonist is administered at an amount of 3 mg/kg. In embodiments, the ROR-1 antagonist is administered at an amount of about 5 mg/kg. In embodiments, the ROR-1 antagonist is administered at an amount of 5 mg/kg. In embodiments, the ROR-1 antagonist is administered at an amount of about 10 mg/kg. In embodiments, the ROR-1 antagonist is administered at an amount of 10 mg/kg.

In embodiments, the BTK antagonist is administered at an amount of about 5 mg/kg and the ROR-1 antagonist is administered at about 2 mg/kg. In embodiments, the BTK antagonist is administered at an amount of 5 mg/kg and the ROR-1 antagonist is administered at 2 mg/kg. In embodiments, the BTK antagonist is administered at an amount of about 5 mg/kg and the ROR-1 antagonist is administered at about 1 mg/kg. In embodiments, the BTK antagonist is administered at an amount of 5 mg/kg and the ROR-1 antagonist is administered at 1 mg/kg.

In embodiments, the BTK antagonist is administered daily over the course of at least 14 days (e.g., 15, 16, 17, 18, 19, 20, 21, 22, 23, 24, 25, 26, 27, 28, 29, 30, 31, 32, 33, 34, 35, 40, 45, or 50 days). In embodiments, the BTK antagonist is administered daily over the course of at least 15 days. In embodiments, the BTK antagonist is administered daily over the course of at least 16 days. In embodiments, the BTK antagonist is administered daily over the course of at least 17 days. In embodiments, the BTK antagonist is administered daily over the course of at least 18 days. In embodiments, the BTK antagonist is administered daily over the course of at least 19 days. In embodiments, the BTK antagonist is administered daily over the course of at least 20 days. In embodiments, the BTK antagonist is administered daily over the course of at least 21 days. In embodiments, the BTK antagonist is administered daily over the course of at least 22 days. In embodiments, the BTK antagonist is administered daily over the course of at least 23 days. In embodiments, the BTK antagonist is administered daily over the course of at least 24 days. In embodiments, the BTK antagonist is administered daily over the course of at least 25 days. In embodiments, the BTK antagonist is administered daily over the course of at least 26 days. In embodiments, the BTK antagonist is administered daily over the course of at least 27 days. In embodiments, the BTK antagonist is administered daily over the course of at least 28 days. In embodiments, the BTK antagonist is administered daily over the course of at least 29 days. In embodiments, the BTK antagonist is administered daily over the course of at least 30 days. In embodiments, the BTK antagonist is administered daily over the course of at least 31 days. In embodiments, the BTK antagonist is administered daily over the course of at least 32 days. In embodiments, the BTK antagonist is administered daily over the course of at least 33 days. In embodiments, the BTK antagonist is administered daily over the course of at least 34 days. In embodiments, the BTK antagonist is administered daily over the course of at least 35 days. In embodiments, the BTK antagonist is administered daily over the course of at least 40 days. In embodiments, the BTK antagonist is administered daily over the course of at least 45 days. In embodiments, the BTK antagonist is administered daily over the course of at least 50 days.

In embodiments, the BTK antagonist is administered daily over the course of about 28 days. In embodiments, the BTK antagonist is administered daily over the course of 28 days.

In embodiments, the ROR-1 antagonist is administered once over the course of about 28 days. In embodiments, the ROR-1 antagonist is administered once over the course of 28 days.

In embodiments, the BTK antagonist is administered intravenously. In embodiments, the ROR-1 antagonist is administered intravenously.

In embodiments, the subject is a mammal. In embodiments, the subject is a human.

As mentioned above, the methods and compositions provided herein including embodiments thereof are useful for the treatment of cancer, and specifically cancers expressing ROR-1. In embodiments, the cancer is lymphoma, leukemia, myeloma, AML, B-ALL, T-ALL, renal cell carcinoma, colon cancer, colorectal cancer, breast cancer, epithelial squamous cell cancer, melanoma, stomach cancer, brain cancer, lung cancer, pancreatic cancer, cervical cancer, ovarian cancer, liver cancer, bladder cancer, prostate cancer, testicular cancer, thyroid cancer, head and neck cancer, uterine cancer, adenocarcinoma, or adrenal cancer. In embodiments, the cancer is chronic lymphocytic leukemia (CLL), small lymphocytic lymphoma, marginal cell B-Cell lymphoma, Burkitt's Lymphoma, or B cell leukemia.

The administered combination of BTK antagonist and ROR-1 antagonist as provided herein, including embodiments thereof, may be varied. For example, a specific BTK antagonist (e.g., ibrutinib) may be administered in combination with a specific ROR-1 antagonist (e.g., cirmtuzumab). Thus, in embodiments, the BTK antagonist ibrutinib is administered in combination with the ROR-1 antagonist cirmtuzumab. In embodiments, the BTK antagonist idelalisib is administered in combination with the ROR-1 antagonist cirmtuzumab. In embodiments, the BTK antagonist fostamatinib is administered in combination with the ROR-1 antagonist cirmtuzumab. In embodiments, the BTK antagonist acalabrutinib is administered in combination with the ROR-1 antagonist cirmtuzumab. In embodiments, the BTK antagonist ONO/GS-4059 is administered in combination with the ROR-1 antagonist cirmtuzumab. In embodiments, the BTK antagonist BGB-3111 is administered in combination with the ROR-1 antagonist cirmtuzumab. In embodiments, the BTK antagonist CC-292 (AVL-292) is administered in combination with the ROR-1 antagonist cirmtuzumab. In embodiments, the BTK antagonist R406 is administered in combination with the ROR-1 antagonist cirmtuzumab.

In embodiments, the BTK antagonist ibrutinib is administered in combination with the ROR-1 antagonist cirmtuzumab, and ibrutinib is administered intravenously at an amount of 1 mg/kg and cirmtuzumab is administered intravenously at an amount of 1 mg/kg. In one further embodiment, ibrutinib is administered daily over the course of 28 days and cirmtuzumab is administered once over the course of 28 days.

In embodiments, the BTK antagonist ibrutinib is administered in combination with the ROR-1 antagonist cirmtuzumab, and ibrutinib is administered intravenously at an amount of 1 mg/kg and cirmtuzumab is administered intravenously at an amount of 2 mg/kg. In one further embodiment, ibrutinib is administered daily over the course of 28 days and cirmtuzumab is administered once over the course of 28 days.

In embodiments, the BTK antagonist ibrutinib is administered in combination with the ROR-1 antagonist cirmtuzumab, and ibrutinib is administered intravenously at an amount of 1 mg/kg and cirmtuzumab is administered intravenously at an amount of 3 mg/kg. In one further embodiment, ibrutinib is administered daily over the course of 28 days and cirmtuzumab is administered once over the course of 28 days.

In embodiments, the BTK antagonist ibrutinib is administered in combination with the ROR-1 antagonist cirmtuzumab, and ibrutinib is administered intravenously at an amount of 1 mg/kg and cirmtuzumab is administered intravenously at an amount of 5 mg/kg. In one further embodiment, ibrutinib is administered daily over the course of 28 days and cirmtuzumab is administered once over the course of 28 days.

In embodiments, the BTK antagonist ibrutinib is administered in combination with the ROR-1 antagonist cirmtuzumab, and ibrutinib is administered intravenously at an amount of 1 mg/kg and cirmtuzumab is administered intravenously at an amount of 10 mg/kg. In one further embodiment, ibrutinib is administered daily over the course of 28 days and cirmtuzumab is administered once over the course of 28 days.

In embodiments, the BTK antagonist ibrutinib is administered in combination with the ROR-1 antagonist cirmtuzumab, and ibrutinib is administered intravenously at an amount of 2 mg/kg and cirmtuzumab is administered intravenously at an amount of 1 mg/kg. In one further embodiment, ibrutinib is administered daily over the course of 28 days and cirmtuzumab is administered once over the course of 28 days.

In embodiments, the BTK antagonist ibrutinib is administered in combination with the ROR-1 antagonist cirmtuzumab, and ibrutinib is administered intravenously at an amount of 2 mg/kg and cirmtuzumab is administered intravenously at an amount of 2 mg/kg. In one further embodiment, ibrutinib is administered daily over the course of 28 days and cirmtuzumab is administered once over the course of 28 days.

In embodiments, the BTK antagonist ibrutinib is administered in combination with the ROR-1 antagonist cirmtuzumab, and ibrutinib is administered intravenously at an amount of 2 mg/kg and cirmtuzumab is administered intravenously at an amount of 3 mg/kg. In one further embodiment, ibrutinib is administered daily over the course of 28 days and cirmtuzumab is administered once over the course of 28 days.

In embodiments, the BTK antagonist ibrutinib is administered in combination with the ROR-1 antagonist cirmtuzumab, and ibrutinib is administered intravenously at an amount of 2 mg/kg and cirmtuzumab is administered intravenously at an amount of 5 mg/kg. In one further embodiment, ibrutinib is administered daily over the course of 28 days and cirmtuzumab is administered once over the course of 28 days.

In embodiments, the BTK antagonist ibrutinib is administered in combination with the ROR-1 antagonist cirmtuzumab, and ibrutinib is administered intravenously at an amount of 2 mg/kg and cirmtuzumab is administered intravenously at an amount of 10 mg/kg. In one further embodiment, ibrutinib is administered daily over the course of 28 days and cirmtuzumab is administered once over the course of 28 days.

In embodiments, the BTK antagonist ibrutinib is administered in combination with the ROR-1 antagonist cirmtuzumab, and ibrutinib is administered intravenously at an amount of 5 mg/kg and cirmtuzumab is administered intravenously at an amount of 1 mg/kg. In one further embodiment, ibrutinib is administered daily over the course of 28 days and cirmtuzumab is administered once over the course of 28 days.

In embodiments, the BTK antagonist ibrutinib is administered in combination with the ROR-1 antagonist cirmtuzumab, and ibrutinib is administered intravenously at an amount of 5 mg/kg and cirmtuzumab is administered intravenously at an amount of 2 mg/kg. In one further embodiment, ibrutinib is administered daily over the course of 28 days and cirmtuzumab is administered once over the course of 28 days.

In embodiments, the BTK antagonist ibrutinib is administered in combination with the ROR-1 antagonist cirmtuzumab, and ibrutinib is administered intravenously at an amount of 5 mg/kg and cirmtuzumab is administered intravenously at an amount of 3 mg/kg. In one further embodiment, ibrutinib is administered daily over the course of 28 days and cirmtuzumab is administered once over the course of 28 days.

In embodiments, the BTK antagonist ibrutinib is administered in combination with the ROR-1 antagonist cirmtuzumab, and ibrutinib is administered intravenously at an amount of 5 mg/kg and cirmtuzumab is administered intravenously at an amount of 5 mg/kg. In one further embodiment, ibrutinib is administered daily over the course of 28 days and cirmtuzumab is administered once over the course of 28 days.

In embodiments, the BTK antagonist ibrutinib is administered in combination with the ROR-1 antagonist cirmtuzumab, and ibrutinib is administered intravenously at an amount of 5 mg/kg and cirmtuzumab is administered intravenously at an amount of 10 mg/kg. In one further embodiment, ibrutinib is administered daily over the course of 28 days and cirmtuzumab is administered once over the course of 28 days.

In embodiments, the BTK antagonist ibrutinib is administered in combination with the ROR-1 antagonist cirmtuzumab, and ibrutinib is administered intravenously at an amount of 10 mg/kg and cirmtuzumab is administered intravenously at an amount of 1 mg/kg. In one further embodiment, ibrutinib is administered daily over the course of 28 days and cirmtuzumab is administered once over the course of 28 days.

In embodiments, the BTK antagonist ibrutinib is administered in combination with the ROR-1 antagonist cirmtuzumab, and ibrutinib is administered intravenously at an amount of 10 mg/kg and cirmtuzumab is administered intravenously at an amount of 2 mg/kg. In one further embodiment, ibrutinib is administered daily over the course of 28 days and cirmtuzumab is administered once over the course of 28 days.

In embodiments, the BTK antagonist ibrutinib is administered in combination with the ROR-1 antagonist cirmtuzumab, and ibrutinib is administered intravenously at an amount of 10 mg/kg and cirmtuzumab is administered intravenously at an amount of 3 mg/kg. In one further embodiment, ibrutinib is administered daily over the course of 28 days and cirmtuzumab is administered once over the course of 28 days.

In embodiments, the BTK antagonist ibrutinib is administered in combination with the ROR-1 antagonist cirmtuzumab, and ibrutinib is administered intravenously at an amount of 10 mg/kg and cirmtuzumab is administered intravenously at an amount of 5 mg/kg. In one further embodiment, ibrutinib is administered daily over the course of 28 days and cirmtuzumab is administered once over the course of 28 days.

In embodiments, the BTK antagonist ibrutinib is administered in combination with the ROR-1 antagonist cirmtuzumab, and ibrutinib is administered intravenously at an amount of 10 mg/kg and cirmtuzumab is administered intravenously at an amount of 10 mg/kg. In one further embodiment, ibrutinib is administered daily over the course of 28 days and cirmtuzumab is administered once over the course of 28 days.

In embodiments, the BTK antagonist ibrutinib is administered in combination with the ROR-1 antagonist cirmtuzumab, and ibrutinib is administered intravenously at an amount of 15 mg/kg and cirmtuzumab is administered intravenously at an amount of 1 mg/kg. In one further embodiment, ibrutinib is administered daily over the course of 28 days and cirmtuzumab is administered once over the course of 28 days.

In embodiments, the BTK antagonist ibrutinib is administered in combination with the ROR-1 antagonist cirmtuzumab, and ibrutinib is administered intravenously at an amount of 15 mg/kg and cirmtuzumab is administered intravenously at an amount of 2 mg/kg. In one further embodiment, ibrutinib is administered daily over the course of 28 days and cirmtuzumab is administered once over the course of 28 days.

In embodiments, the BTK antagonist ibrutinib is administered in combination with the ROR-1 antagonist cirmtuzumab, and ibrutinib is administered intravenously at an amount of 15 mg/kg and cirmtuzumab is administered intravenously at an amount of 3 mg/kg. In one further embodiment, ibrutinib is administered daily over the course of 28 days and cirmtuzumab is administered once over the course of 28 days.

In embodiments, the BTK antagonist ibrutinib is administered in combination with the ROR-1 antagonist cirmtuzumab, and ibrutinib is administered intravenously at an amount of 15 mg/kg and cirmtuzumab is administered intravenously at an amount of 5 mg/kg. In one further embodiment, ibrutinib is administered daily over the course of 28 days and cirmtuzumab is administered once over the course of 28 days.

In embodiments, the BTK antagonist ibrutinib is administered in combination with the ROR-1 antagonist cirmtuzumab, and ibrutinib is administered intravenously at an amount of 15 mg/kg and cirmtuzumab is administered intravenously at an amount of 10 mg/kg. In one further embodiment, ibrutinib is administered daily over the course of 28 days and cirmtuzumab is administered once over the course of 28 days.

In embodiments, the BTK antagonist ibrutinib is administered in combination with the ROR-1 antagonist cirmtuzumab, and ibrutinib is administered intravenously at an amount of 420 mg and cirmtuzumab is administered intravenously at an amount of 1 mg/kg. In one further embodiment, ibrutinib is administered daily over the course of 28 days and cirmtuzumab is administered once over the course of 28 days.

In embodiments, the BTK antagonist ibrutinib is administered in combination with the ROR-1 antagonist cirmtuzumab, and ibrutinib is administered intravenously at an amount of 420 mg and cirmtuzumab is administered intravenously at an amount of 2 mg/kg. In one further embodiment, ibrutinib is administered daily over the course of 28 days and cirmtuzumab is administered once over the course of 28 days.

In embodiments, the BTK antagonist ibrutinib is administered in combination with the ROR-1 antagonist cirmtuzumab, and ibrutinib is administered intravenously at an amount of 420 mg and cirmtuzumab is administered intravenously at an amount of 3 mg/kg. In one further embodiment, ibrutinib is administered daily over the course of 28 days and cirmtuzumab is administered once over the course of 28 days.

In embodiments, the BTK antagonist ibrutinib is administered in combination with the ROR-1 antagonist cirmtuzumab, and ibrutinib is administered intravenously at an amount of 420 mg and cirmtuzumab is administered intravenously at an amount of 5 mg/kg. In one further embodiment, ibrutinib is administered daily over the course of 28 days and cirmtuzumab is administered once over the course of 28 days.

In embodiments, the BTK antagonist ibrutinib is administered in combination with the ROR-1 antagonist cirmtuzumab, and ibrutinib is administered intravenously at an amount of 420 mg and cirmtuzumab is administered intravenously at an amount of 10 mg/kg. In one further embodiment, ibrutinib is administered daily over the course of 28 days and cirmtuzumab is administered once over the course of 28 days.

Pharmaceutical Compositions

The compositions including a BTK antagonist and a ROR-1 antagonist as provided herein, including embodiments thereof, are further contemplated as pharmaceutical compositions. Thus, in an aspect is provided a pharmaceutical composition including a BTK antagonist, a ROR-1 antagonist and a pharmaceutically acceptable excipient.

In another aspect, there is provided a pharmaceutical composition including a Bruton's tyrosine kinase (BTK) antagonist, an anti-ROR-1 antibody and a pharmaceutically acceptable excipient. In embodiments, the BTK antagonist and the anti-ROR-1 antibody are present in a combined synergistic amount, wherein the combined synergistic amount is effective to treat cancer in a subject in need thereof.

The BTK antagonist and ROR-1 antagonist included in the pharmaceutical compositions provided herein may be any one of the BTK antagonists and/or ROR-1 antagonists described herein including embodiments thereof. For example, the BTK antagonist may be ibrutinib and the ROR-1 antagonist may be cirmtuzumab. Likewise, pharmaceutical compositions provided herein may be formulated such that the administered amount of BTK antagonist and ROR-1 antagonist is any one of the amounts as described herein. For example, the ibrutinib may be present in an amount such that administration of the composition results in a dosage of about 5 mg/kg or 420 mg and cirmtuzumab may be present in an amount that results in a dosage of about 2 mg/kg.

The provided compositions are, inter alia, suitable for formulation and administration in vitro or in vivo. Suitable carriers and excipients and their formulations are described in Remington: The Science and Practice of Pharmacy, 21st Edition, David B. Troy, ed., Lippicott Williams & Wilkins (2005). By pharmaceutically acceptable carrier is meant a material that is not biologically or otherwise undesirable, i.e., the material is administered to a subject without causing undesirable biological effects or interacting in a deleterious manner with the other components of the pharmaceutical composition in which it is contained. If administered to a subject, the carrier is optionally selected to minimize degradation of the active ingredient and to minimize adverse side effects in the subject.

Pharmaceutical compositions provided herein include compositions wherein the active ingredient (e.g. compositions described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, the recombinant proteins described herein will contain an amount of active ingredient effective to achieve the desired result, e.g., modulating the activity of a target molecule, and/or reducing, eliminating, or slowing the progression of disease symptoms. Determination of a therapeutically effective amount of a compound of the invention is well within the capabilities of those skilled in the art, especially in light of the detailed disclosure herein.

Provided compositions can include a single agent or more than one agent. The compositions for administration will commonly include an agent as described herein dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the subject's needs.

Solutions of the active compounds as free base or pharmacologically acceptable salt can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations can contain a preservative to prevent the growth of microorganisms.

Pharmaceutical compositions can be delivered via intranasal or inhalable solutions or sprays, aerosols or inhalants. Nasal solutions can be aqueous solutions designed to be administered to the nasal passages in drops or sprays. Nasal solutions can be prepared so that they are similar in many respects to nasal secretions. Thus, the aqueous nasal solutions usually are isotonic and slightly buffered to maintain a pH of 5.5 to 6.5. In addition, antimicrobial preservatives, similar to those used in ophthalmic preparations and appropriate drug stabilizers, if required, may be included in the formulation. Various commercial nasal preparations are known and can include, for example, antibiotics and antihistamines.

Oral formulations can include excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders. In some embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25-60%. The amount of active compounds in such compositions is such that a suitable dosage can be obtained.

For parenteral administration in an aqueous solution, for example, the solution should be suitably buffered and the liquid diluent first rendered isotonic with sufficient saline or glucose. Aqueous solutions, in particular, sterile aqueous media, are especially suitable for intravenous, intramuscular, subcutaneous and intraperitoneal administration. For example, one dosage could be dissolved in 1 ml of isotonic NaCl solution and either added to 1000 ml of hypodermoclysis fluid or injected at the proposed site of infusion.

Sterile injectable solutions can be prepared by incorporating the active compounds or constructs in the required amount in the appropriate solvent followed by filtered sterilization. Generally, dispersions are prepared by incorporating the various sterilized active ingredients into a sterile vehicle which contains the basic dispersion medium. Vacuum-drying and freeze-drying techniques, which yield a powder of the active ingredient plus any additional desired ingredients, can be used to prepare sterile powders for reconstitution of sterile injectable solutions. The preparation of more, or highly, concentrated solutions for direct injection is also contemplated. DMSO can be used as solvent for extremely rapid penetration, delivering high concentrations of the active agents to a small area.

The formulations of compounds can be presented in unit-dose or multi-dose sealed containers, such as ampules and vials. Thus, the composition can be in unit dosage form. In such form the preparation is subdivided into unit doses containing appropriate quantities of the active component. Thus, the compositions can be administered in a variety of unit dosage forms depending upon the method of administration. For example, unit dosage forms suitable for oral administration include, but are not limited to, powder, tablets, pills, capsules and lozenges.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated (e.g. symptoms of cancer and severity of such symptoms), kind of concurrent treatment, complications from the disease being treated or other health-related problems. Other therapeutic regimens or agents can be used in conjunction with the methods and compounds of the invention. Adjustment and manipulation of established dosages (e.g., frequency and duration) are well within the ability of those skilled in the art.

For any composition (e.g., the cell-penetrating conjugate provided) described herein, the therapeutically effective amount can be initially determined from cell culture assays. Target concentrations will be those concentrations of active compound(s) that are capable of achieving the methods described herein, as measured using the methods described herein or known in the art. As is well known in the art, effective amounts for use in humans can also be determined from animal models. For example, a dose for humans can be formulated to achieve a concentration that has been found to be effective in animals. The dosage in humans can be adjusted by monitoring effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to affect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred "Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "pharmaceutically acceptable salt" refers to salts derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

In embodiments, the pharmaceutical composition consists of ibrutinib, cirmtuzumab, and a pharmaceutically acceptable excipient. In embodiments, the pharmaceutical composition consists of idelalisib, cirmtuzumab, and a pharmaceutically acceptable excipient. In embodiments, the pharmaceutical composition consists of fostamatinib, cirmtuzumab, and a pharmaceutically acceptable excipient. In embodiments, the pharmaceutical composition consists of acalabrutinib, cirmtuzumab, and a pharmaceutically acceptable excipient. In embodiments, the pharmaceutical composition consists of ONO/GS-4059, cirmtuzumab, and a pharmaceutically acceptable excipient. In embodiments, the pharmaceutical composition consists of BGB-3111, cirmtuzumab, and a pharmaceutically acceptable excipient. In embodiments, the pharmaceutical composition consists of CC-292 (AVL-292), cirmtuzumab, and a pharmaceutically acceptable excipient. In embodiments, the pharmaceutical composition consists of R406, cirmtuzumab, and a pharmaceutically acceptable excipient.

In embodiments, the pharmaceutical composition includes an amount of ibrutinib equivalent to a dose of 1 mg/kg and an amount of cirmtuzumab equivalent to a dose of 1 mg/kg. In embodiments, the pharmaceutical composition includes an amount of ibrutinib equivalent to a dose of 1 mg/kg and an amount of cirmtuzumab equivalent to a dose of 2 mg/kg. In embodiments, the pharmaceutical composition includes an amount of ibrutinib equivalent to a dose of 1 mg/kg and an amount of cirmtuzumab equivalent to a dose of 3 mg/kg. In embodiments, the pharmaceutical composition includes an amount of ibrutinib equivalent to a dose of 1 mg/kg and an amount of cirmtuzumab equivalent to a dose of 5 mg/kg. In embodiments, the pharmaceutical composition includes an amount of ibrutinib equivalent to a dose of 1 mg/kg and an amount of cirmtuzumab equivalent to a dose of 10 mg/kg.

In embodiments, the pharmaceutical composition includes an amount of ibrutinib equivalent to a dose of 2 mg/kg and an amount of cirmtuzumab equivalent to a dose of 1 mg/kg. In embodiments, the pharmaceutical composition includes an amount of ibrutinib equivalent to a dose of 2 mg/kg and an amount of cirmtuzumab equivalent to a dose of 2 mg/kg. In embodiments, the pharmaceutical composition includes an amount of ibrutinib equivalent to a dose of 2 mg/kg and an amount of cirmtuzumab equivalent to a dose of 3 mg/kg. In embodiments, the pharmaceutical composition includes an amount of ibrutinib equivalent to a dose of 2 mg/kg and an amount of cirmtuzumab equivalent to a dose of 5 mg/kg. In embodiments, the pharmaceutical composition includes an amount of ibrutinib equivalent to a dose of 2 mg/kg and an amount of cirmtuzumab equivalent to a dose of 10 mg/kg.

In embodiments, the pharmaceutical composition includes an amount of ibrutinib equivalent to a dose of 5 mg/kg and an amount of cirmtuzumab equivalent to a dose of 1 mg/kg. In embodiments, the pharmaceutical composition includes an amount of ibrutinib equivalent to a dose of 5 mg/kg and an amount of cirmtuzumab equivalent to a dose of 2 mg/kg. In embodiments, the pharmaceutical composition includes an amount of ibrutinib equivalent to a dose of 5 mg/kg and an amount of cirmtuzumab equivalent to a dose of 3 mg/kg. In embodiments, the pharmaceutical composition includes an amount of ibrutinib equivalent to a dose of 5 mg/kg and an amount of cirmtuzumab equivalent to a dose of 5 mg/kg. In embodiments, the pharmaceutical composition includes an amount of ibrutinib equivalent to a dose of 5 mg/kg and an amount of cirmtuzumab equivalent to a dose of 10 mg/kg.

In embodiments, the pharmaceutical composition includes an amount of ibrutinib equivalent to a dose of 10 mg/kg and an amount of cirmtuzumab equivalent to a dose of 1 mg/kg. In embodiments, the pharmaceutical composition includes an amount of ibrutinib equivalent to a dose of 10 mg/kg and an amount of cirmtuzumab equivalent to a dose of 2 mg/kg. In embodiments, the pharmaceutical composition includes an amount of ibrutinib equivalent to a dose of 10 mg/kg and an amount of cirmtuzumab equivalent to a dose of 3 mg/kg. In embodiments, the pharmaceutical composition includes an amount of ibrutinib equivalent to a dose of 10 mg/kg and an amount of cirmtuzumab equivalent to a dose of 5 mg/kg. In embodiments, the pharmaceutical composition includes an amount of ibrutinib equivalent to a dose of 10 mg/kg and an amount of cirmtuzumab equivalent to a dose of 10 mg/kg.

In embodiments, the pharmaceutical composition includes an amount of ibrutinib equivalent to a dose of 15 mg/kg and an amount of cirmtuzumab equivalent to a dose of 1 mg/kg. In embodiments, the pharmaceutical composition includes an amount of ibrutinib equivalent to a dose of 15 mg/kg and an amount of cirmtuzumab equivalent to a dose of 2 mg/kg. In embodiments, the pharmaceutical composition includes an amount of ibrutinib equivalent to a dose of 15 mg/kg and an amount of cirmtuzumab equivalent to a dose of 3 mg/kg. In embodiments, the pharmaceutical composition includes an amount of ibrutinib equivalent to a dose of 15 mg/kg and an amount of cirmtuzumab equivalent to a dose of 5 mg/kg. In embodiments, the pharmaceutical composition includes an amount of ibrutinib equivalent to a dose of 15 mg/kg and an amount of cirmtuzumab equivalent to a dose of 10 mg/kg.

In embodiments, the pharmaceutical composition includes an amount of ibrutinib equivalent to a dose of 420 mg and an amount of cirmtuzumab equivalent to a dose of 1 mg/kg. In embodiments, the pharmaceutical composition includes an amount of ibrutinib equivalent to a dose of 420 mg and an amount of cirmtuzumab equivalent to a dose of 2 mg/kg. In embodiments, the pharmaceutical composition includes an amount of ibrutinib equivalent to a dose of 420 mg and an amount of cirmtuzumab equivalent to a dose of 3 mg/kg. In embodiments, the pharmaceutical composition includes an amount of ibrutinib equivalent to a dose of 420 mg and an amount of cirmtuzumab equivalent to a dose of 5 mg/kg. In embodiments, the pharmaceutical composition includes an amount of ibrutinib equivalent to a dose of 420 mg and an amount of cirmtuzumab equivalent to a dose of 10 mg/kg.

EXAMPLES

Signaling via BCR (B-Cell Receptor) signaling is thought to play a role in the pathogenesis and/or progression of disease, e.g., chronic lymphocytic leukemia (CLL). The importance of this cascade in CLL biology appears underscored by clinical trials demonstrating clinical activity with small-molecule kinase inhibitors intended to block BCR-signaling. However, almost all the inhibitors intended to block BCR-signaling could not have complete response (CR), suggesting that other mechanisms that counterbalance BCR signaling may be involved in the CR of CLL following treatment with BCR signaling. Applicants found, inter alia, that ROR-1, a survival signal for CLL, was induced by the inhibitors and can account for this effect.

Receptor tyrosine kinase-like orphan receptor 1 (ROR-1) is an oncoembryonic antigen that is expression on the cell surface of lymphoma and leukemia cells from patients with chronic lymphocytic leukemia (CLL) and mantle cell lymphoma (MCL), but not on normal B-cells or other postpartum tissues. The binding of the ligand Wnt5a to ROR-1 results in the recruitment of guanine exchange factors (GEFs), which activate Rac1 and RhoA and promote disease related chemotaxis and proliferation. Targeting the BCR and ROR-1 signaling pathways with simultaneous inhibition of BTKBTK and ROR-1 has not yet been reported. The work presented here evaluated the activity of ibrutinib combined with the novel and selective anti-ROR-1 antibody cirmtuzumab in primary CLL samples. Treatment with both BTK inhibitor and anti-ROR-1 antibodies further reduced CLL cell survival when compared to treatment with the single agents alone, and in combination induced synergistic growth inhibition as the result of further disrupted ligand induced signaling. Hence, simultaneous targeting of these kinases may significantly increase clinical activity.

Moreover, the enhanced efficacy observed with the combination treatment of anti-ROR-1 and Ibrutinib was an unexpected benefit. Specifically, combining Ibrutinib with anti-CD20 antibodies that display cell-mediated anti-tumor reactivities did not display enhanced efficacy. In fact, it was shown that Ibrutinib interfered with the activity of the CD20 antibodies.

Example 1. Combination of Cirmtuzumab (UC-961) with Ibrutinib for Treatment of Chronic Lymphocytic Leukemia Abstract. Ibrutinib, a small molecule that irreversibly inhibits Bruton's tyrosine kinase (BTK), has shown efficacy in the treatment of patients with chronic lymphocytic leukemia (CLL) by blocking B-cell receptor (BCR) signaling, but does not induce complete responses (CR) or durable remissions. RTK-like orphan receptor-1 (ROR-1) is a receptor for Wnt5a and plays an important role in non-canonical Wnt signaling in CLL progression. In this study, Applicants tested the effects of ibrutinib on Wnt5a/ROR-1 signaling-mediated activities in CLL cells. Applicants found that Wnt5a can induce Rac1 activation in CLL cells treated with ibrutinib and that although ibrutinib treatment can inhibit CLL proliferation in the absence of Wnt5a; this was reversed by Wnt5a stimulation. Such effects were blocked by a humanized anti-ROR-1 monoclonal antibody (mAb), cirmtuzumab (UC-961). Moreover, combinatory treatment with UC-961 and ibrutinib significantly inhibited CLL proliferation in vitro and engraftment of ROR-1+ leukemia cells in vivo, which was more effective than each agent alone. The outcomes of this study provide rationale to combine UC-961 and ibrutinib as therapy for patients with CLL and other ROR-1-expressing B cell tumors.

Introduction. Signaling via B cell receptor (BCR) plays an important role in the pathogenesis and progression of CLL. Crosslinking of the BCR leads to phosphorylation of CD79a/b and Src family kinase LYN, resulting in the recruitment and activation of the tyrosine kinase Syk, which induces a cascade of downstream signaling events, leading to enhanced B-cell survival. The importance of this cascade in CLL biology appears underscored by the therapeutic effects of small-molecule inhibitors of kinases such as Syk, Akt and BTK, which are important in BCR-signaling. Ibrutinib is an inhibitor of BTK and can induce durable clinical responses in most patients, provided that they continue therapy indefinitely. However, most patients generally achieve only partial responses (PR). Moreover, patients virtually never achieve complete responses (CR) lacking detectable minimal residual disease (MRD), even after prolonged single-agent therapy.

The failure of ibrutinib to achieve deep CRs could be due to the presence of alternative survival signaling pathways that are not blocked by inhibitors of BTK. One such pathway is that induced by signaling via ROR-1, an oncoembryonic antigen expressed on CLL cells, but not on normal postpartum tissues. Applicants found that ROR-1 could serve as a receptor for Wnt5a, which could induce non-canonical Wnt-signaling leading to activation of Rho GTPases, such as Rac1, and enhanced leukemia-cell proliferation and survival. Activation of Rac1 by Wnt5a could be inhibited by an anti-ROR-1 mAb, UC-961, which is a first-in-class humanized monoclonal antibody currently undergoing evaluation in clinical trials for patients with CLL.

In this study, Applicants investigated Wnt5a/ROR-1 signaling in the presence of the BCR signaling inhibitor ibrutinib, and examined the combinatory effect of ibrutinib and a humanized anti-ROR-1 monoclonal antibody (mAb), cirmtuzumab (UC-961), for CLL treatment in vitro and in vivo.

Results.

Figure 6A:
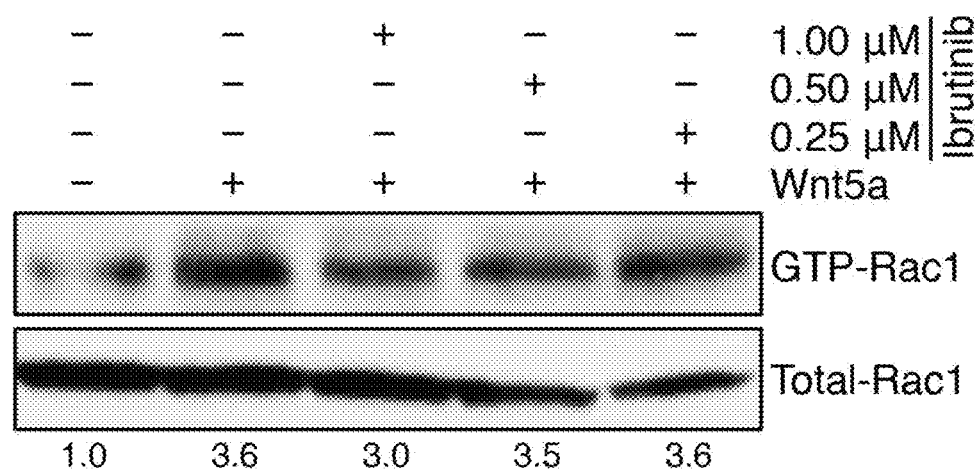
FIGS. 6A-6D. Ibrutinib inhibits BCR signaling, but not WntSa/ROR-1 signaling.
Figure 6B:
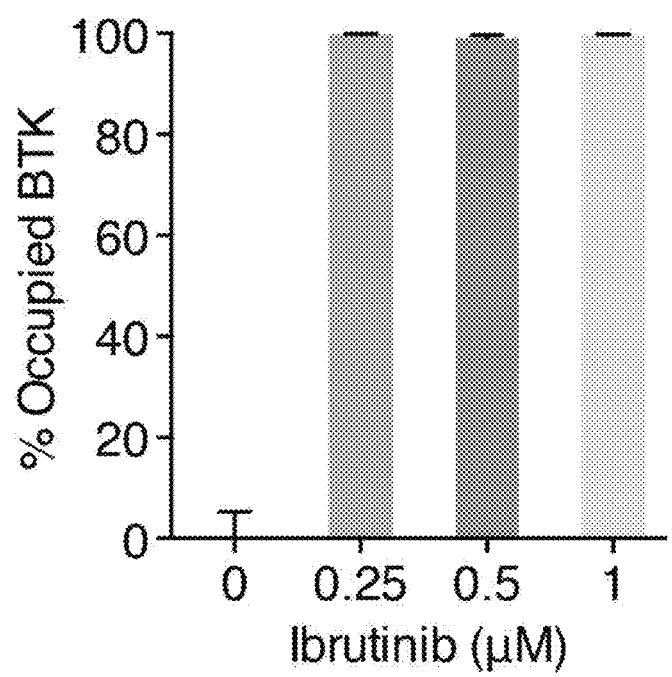
Figure 6C:
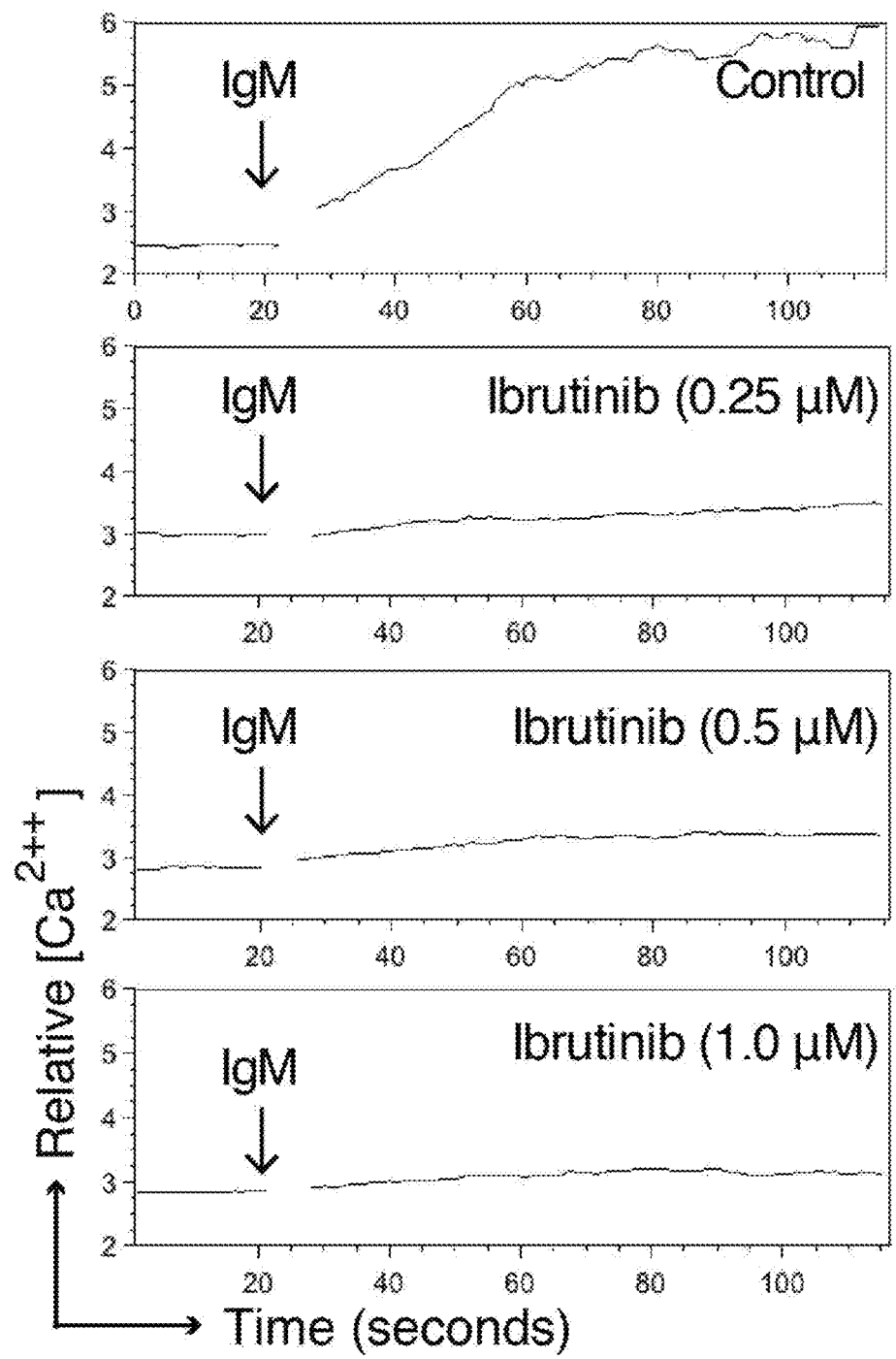
Figure 6D:
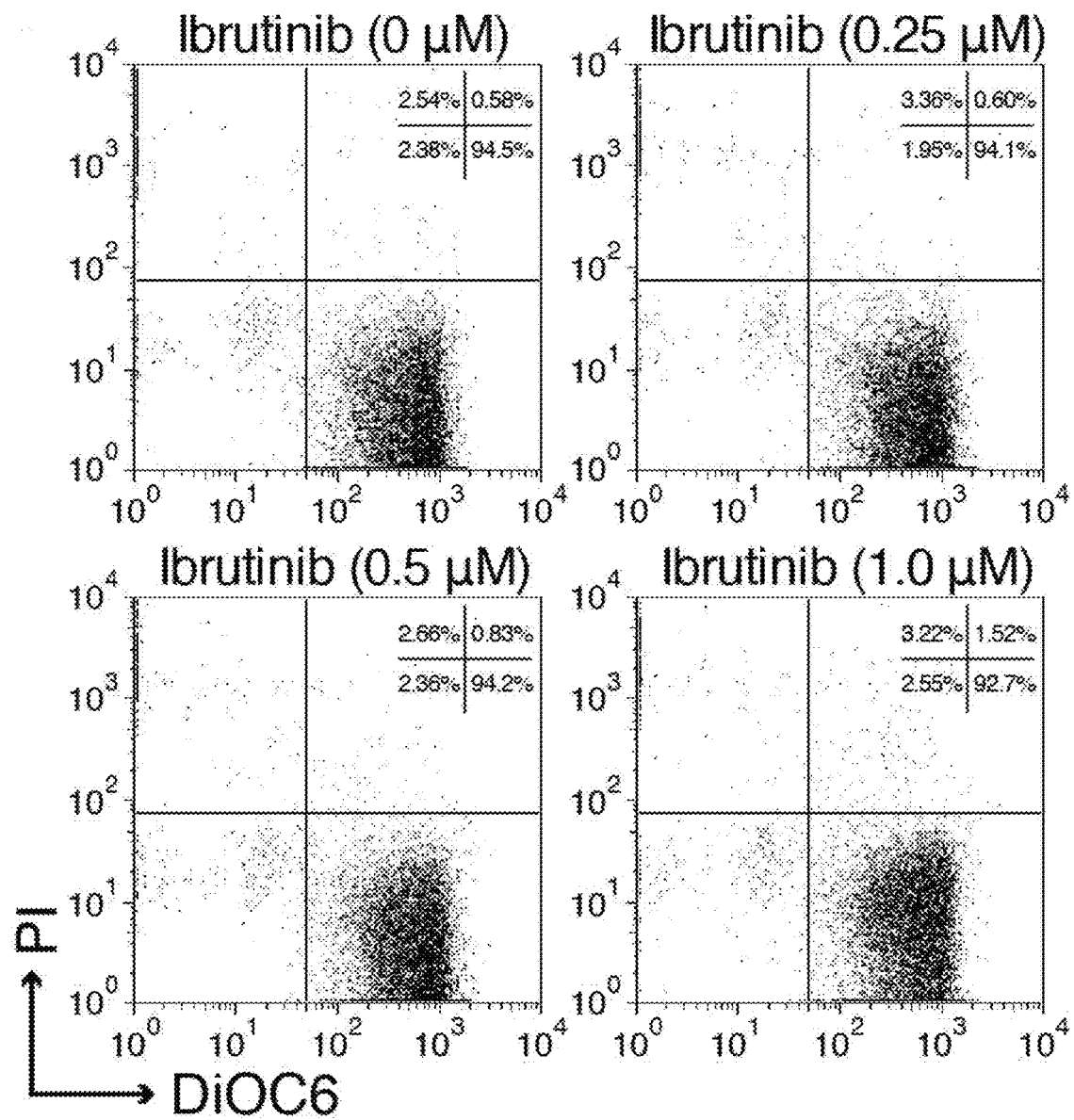

UC-961 inhibits Wnt5a-induced Rac1 activation in CLL cells in the presence of ibrutinib. Wnt5a can induce activation of Rac1 in a variety of cell types, including CLL cells. Applicants evaluated whether Wnt5a could induce Rac1 activation in CLL cells treated with ibrutinib. For this, Applicants treated CLL cells with ibrutinib at concentrations of 0, 0.25, 0.5 or 1.0 µM for 2 hours and then treated the cells with exogenous Wnt5a for 30 minutes. Immunoblot analysis showed that treatment with Wnt5a induced Rac1 activation and that such activation could not be blocked by ibrutinib, even at concentrations of 1 µM (FIG. 6A), a concentration considered super-physiologic, and one that caused 100% of BTK occupancy (FIG. 6B), consistent with previous reports. Moreover, concentrations of ibrutinib as low as 0.25 µM caused complete inhibition of calcium flux induced by BCR-ligation with anti-µ (FIG. S11C), without acutely affecting CLL-cell viability (FIG. 6D).

Figure 1B:
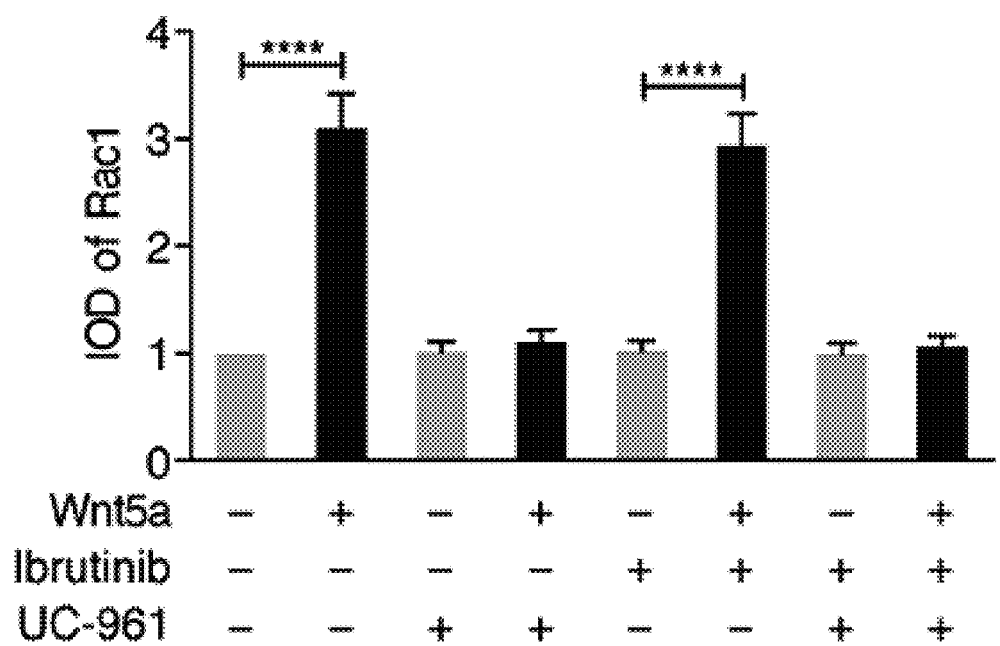

The maximal concentration of ibrutinib in CLL patient plasma is approximately 0.5 µM. As such, Applicants treated CLL cells with 0.5 µM ibrutinib in subsequent studies. Applicants examined for Wnt5a-induced Rac1 activation with or without UC-961. Applicants pretreated CLL cells with ibrutinib, UC-961 or combination of ibrutinib and UC-961 for 2 hours, and then treated them with or without Wnt5a recombinant protein for 30 minutes. Ibrutinib did not inhibit Wnt5a-induced Rac1 activation, however, treatment of UC-961 reduced Wnt5a-induced Rac1 activation to levels comparable to those observed in CLL cells that did not get treated with exogenous Wnt5a (FIGS. 1A-1B). Furthermore, the combination of UC-961 with ibrutinib also inhibited Wnt5a-induced Rac1 to the basal levels (FIGS. 1A-1B).

Figure 1C:
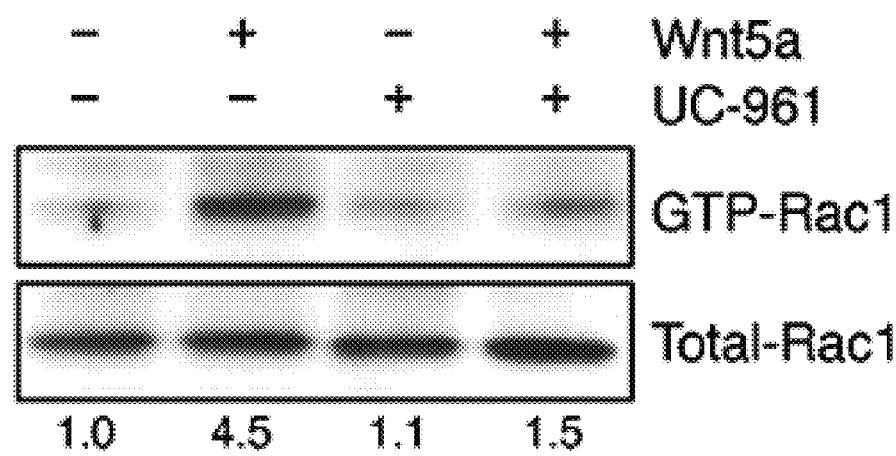
Figure 1D:
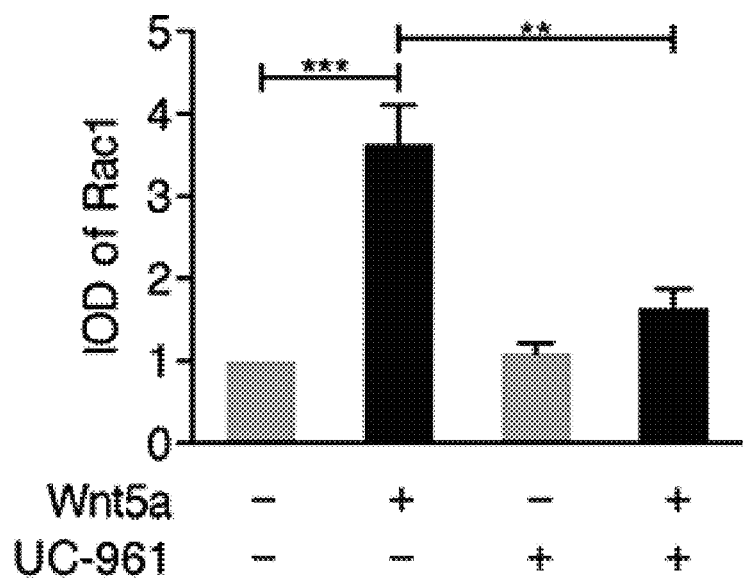

Applicants examined whether CLL cells of patients undergoing therapy with ibrutinib could be stimulated with Wnt5a. For this, blood mononuclear cells were collected from patients undergoing treatment with ibrutinib at the standard therapeutic dose of 420 mg QD. The isolated CLL cells were incubated with or without Wnt5a and/or UC-961. Western blot analysis showed that Wnt5a induced Rac1 activation in CLL cells from these patients, whereas incubation of UC-961 inhibited the Wnt5a-induced Rac1 activation; the level of active Rac1 was similar to that in samples without treatment (FIGS. 1C-1D). These results demonstrate that ibrutinib does not inhibit Wnt5a-induced Rac1 activation.

Figure 2A:
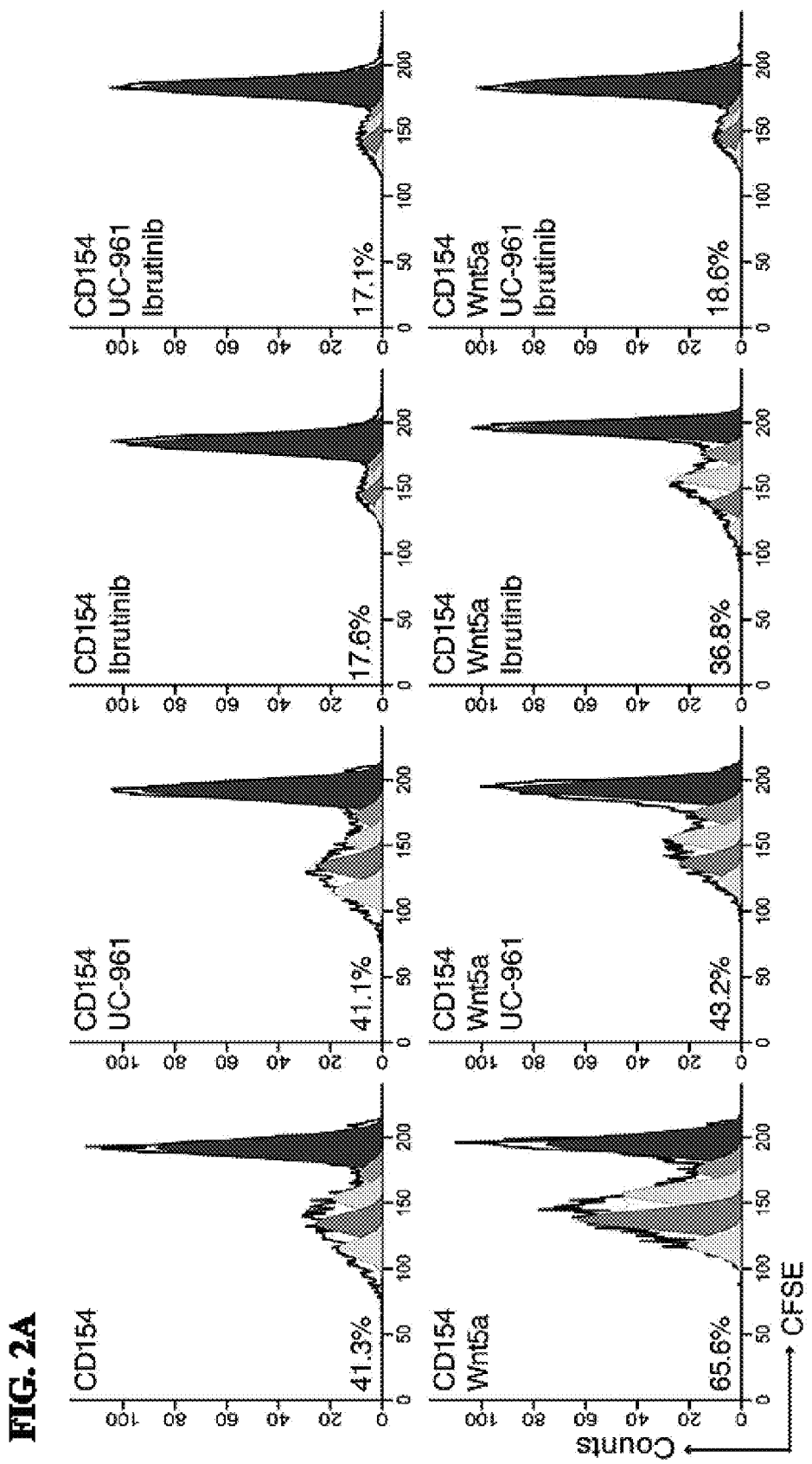
FIGS. 2A-2B. UC-961 inhibits Wnt5a-enhanced proliferation in ibrutinib-treated CLL cells.
Figure 2B:
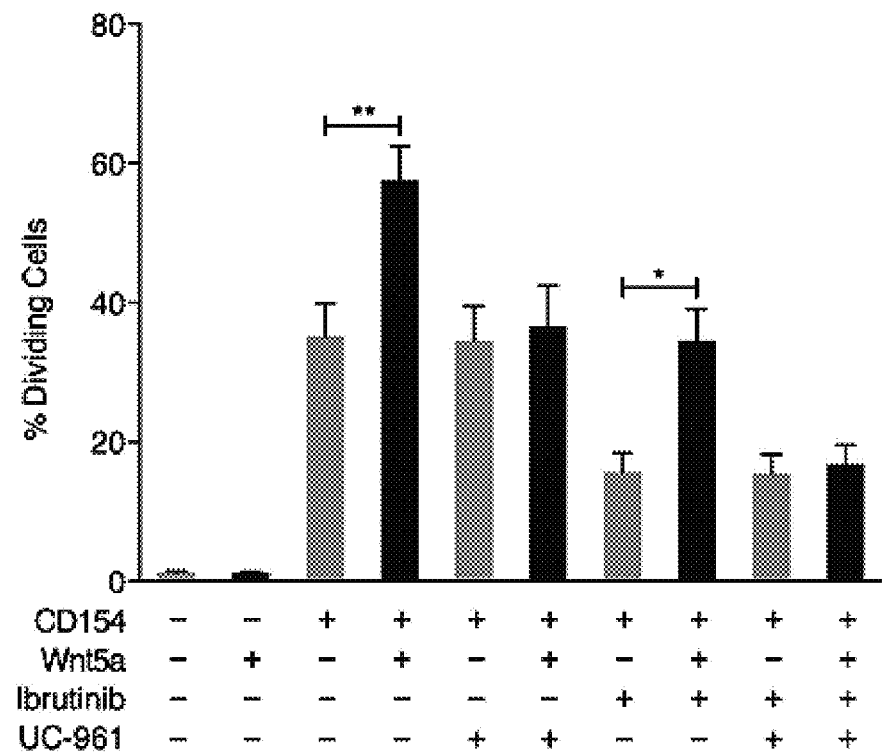
Figure 7A:
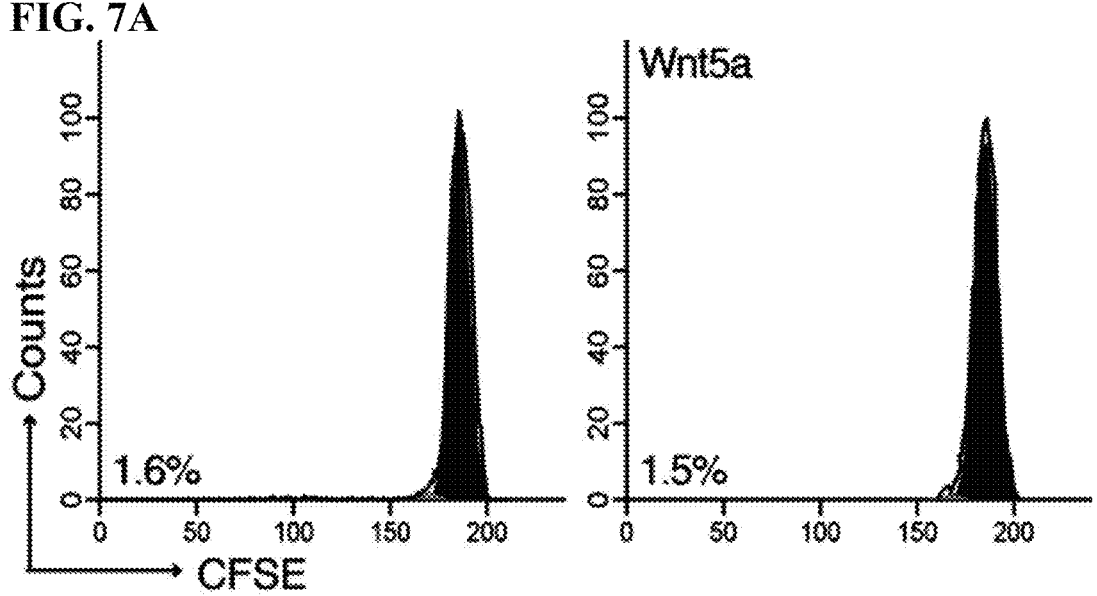
Figure 7B:
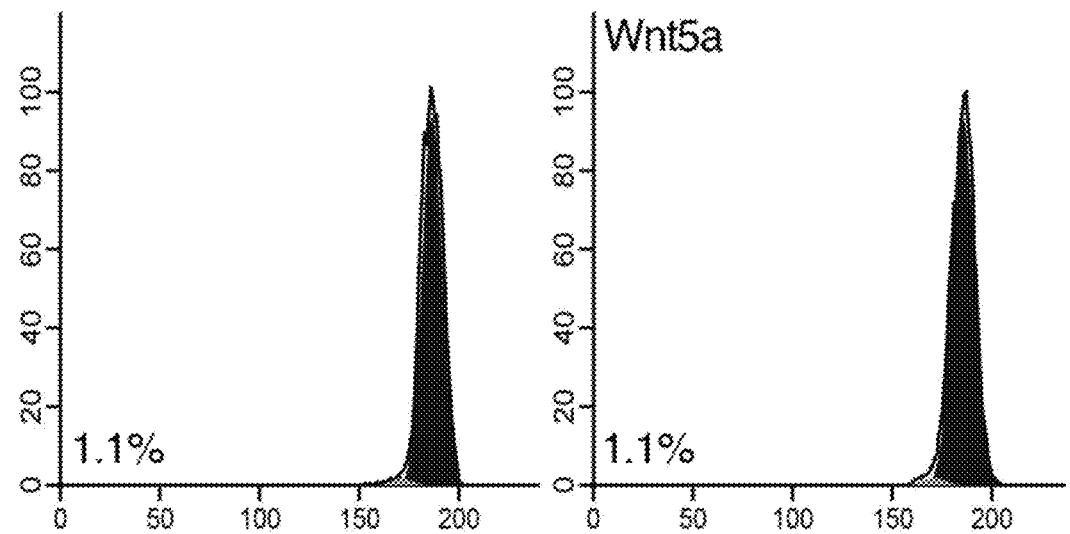

UC-961 inhibits Wnt5a-enhanced proliferation of CLL cells in the presence of ibrutinib. Activation of Rac1-GTPase can enhance proliferation. Applicants induced proliferation of CLL cells by co-culturing with cells expressing CD154 (HeLacD154) in the presence of exogenous interleukin (IL)-4 and IL-10. Addition of exogenous Wnt5a to such cultures significantly enhanced the proportion of dividing cells deduced from the fluorescence intensity of cells labeled with carboxyfluorescein succinimidyl ester (CFSE); this effect could be inhibited by UC-961 (FIG. 2A). In contrast, CLL cells co-cultured with wild-type HeLa cells were not induced proliferate, even in the presence of IL-4/10 and/or Wnt5a (FIGS. 7A-7B). Applicants' results demonstrated that the proliferation induced by Wnt5a could be inhibited by UC-961 to levels comparable to those observed in cultures without Wnt5a. Treatment with ibrutinib could inhibit CD154-induced CLL-cell proliferation; however, exogenous Wnt5a still could enhance the proportion of dividing cells in the presence of ibrutinib (FIG. 2A); this could be inhibited by UC-961 (FIG. 2A). The same effects were observed using CLL cells of different patients (N=6) (FIG. 2B). Collectively, these data demonstrate that UC-961 could block Wnt5a-signaling that was not affected by treatment with ibrutinib.

Figure 3:
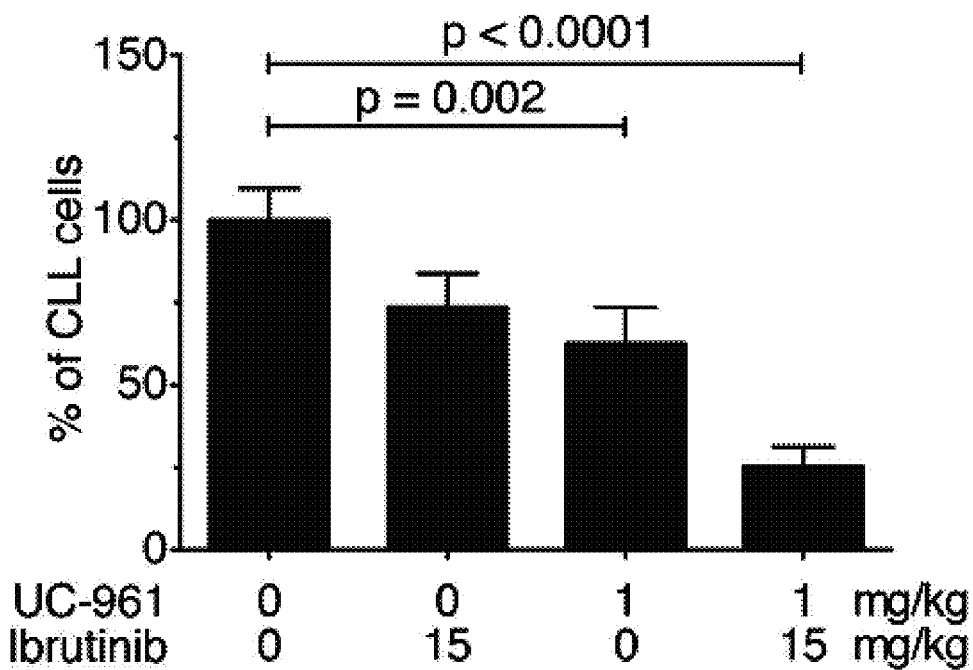
FIG. 3. Additive inhibitory effect of UC-961 and ibrutinib in CLL patient derived xenograft mice. CLL cells were injected to the peritoneal cavity of $Rag2^{-/-}\gamma_c^{-/-}$ mice 1 d before treatment as indicated. Peritoneal lavage was collected 7 d after cell injection and subjected to residual CLL determination by cell counting and flow cytometry analysis following staining with mAb specific for CD5, CD19, and CD45. Each bar in the graph represents percentage of residual CLL cells harvested form mice after treatment, normalized with respect to cells harvested from mice without treatment. Data shown are mean±SEM from 3 different patients with 5 mice in each group. P-values were determined by one-way ANOVA with Tukey's multiple comparisons test.

Combination of UC-961 and ibrutinib in CLL patient derived xenograft. Applicants transferred CLL into the peritoneal cavity of immune-deficient $Rag2^{-/-}\gamma_c^{-/-}$ mice to generate xenografts. Applicants examined the capacity of the combination of UC-961 with ibrutinib to deplete CLL cells in such xenografts. For this, Applicants injected $1\times10^7$ viable primary CLL cells in AIM-V medium into the peritoneal cavity of each mouse. One day later, the mice were provided no treatment or daily doses of 15 mg/kg ibrutinib via gavage, and/or a single dose of UC-961 at 1 mg/kg. After 7 days, the CLL cells were harvested via peritoneal lavage (PL) and were examined by flow cytometry. The calculated CLL cell numbers per PL were significantly less in the group of mice treated with UC-961 or ibrutinib than the numbers collected from control non-treated mice. However, animals treated with both UC-961 and ibrutinib had significantly fewer CLL cells per PL than each other group, including those treated with single agent ibrutinib or UC-961 (FIG. 3). These data demonstrate an additive effect of UC-961 on ibrutinib in clearing leukemia cells in this xenografts model.

Figure 4A:
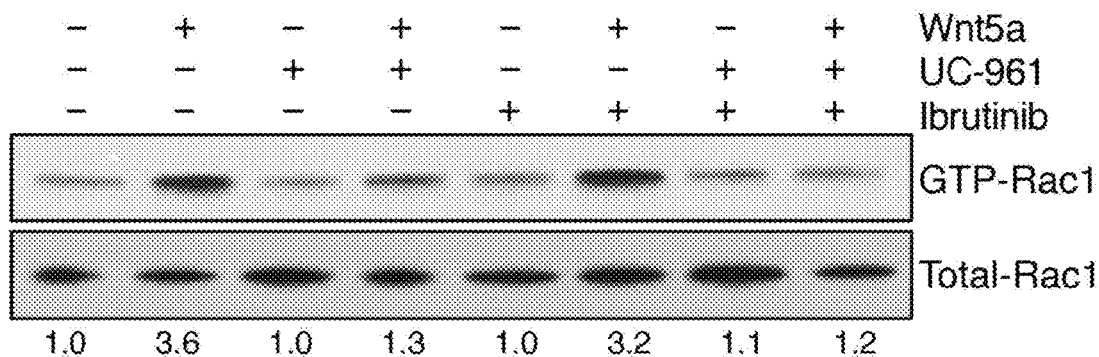
Figure 4B:
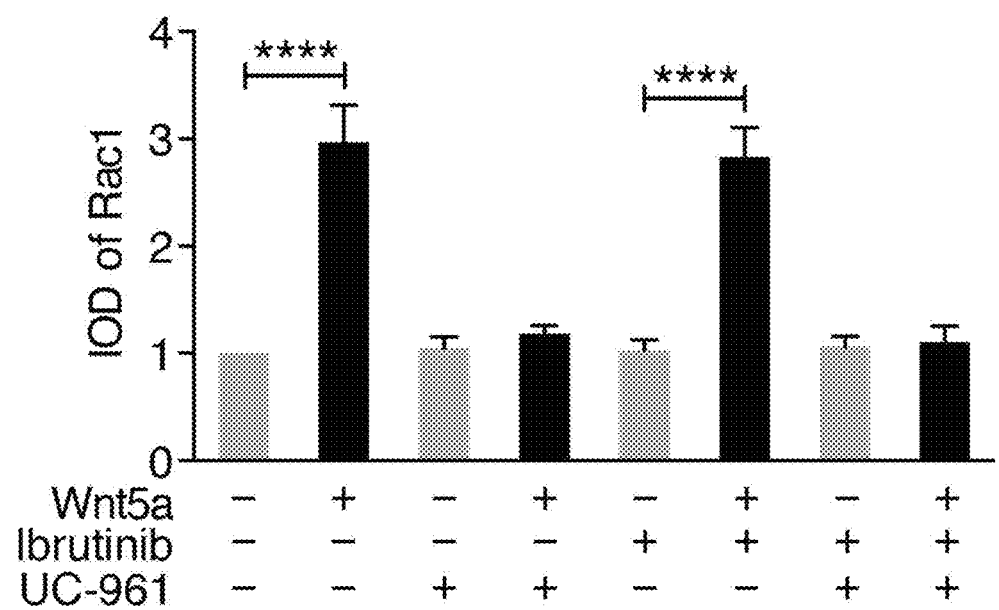
Figure 4D:
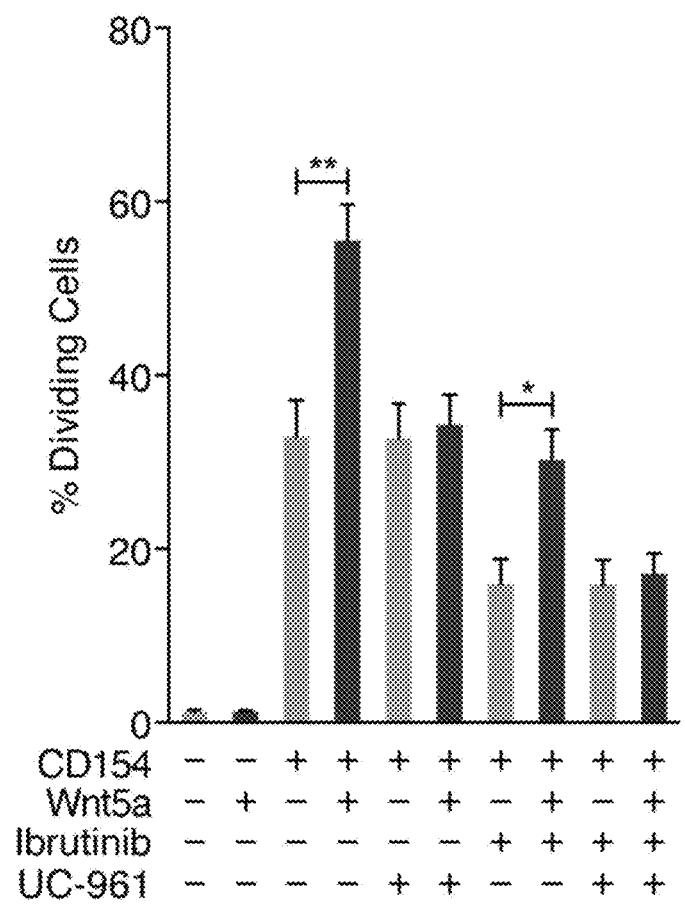
Figure 8A:
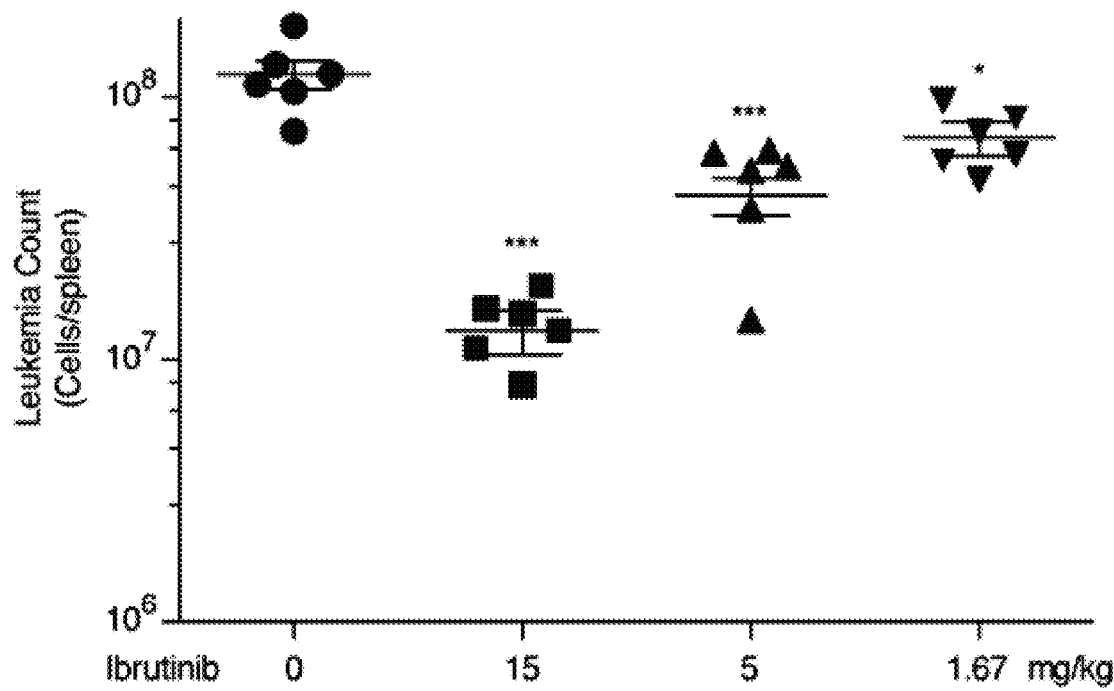
FIGS. 8A-8B. Dose-dependent inhibitory effect of UC-961 or ibrutinib in ROR-1×TCL1 leukemia xenograft mice.
Figure 8B:
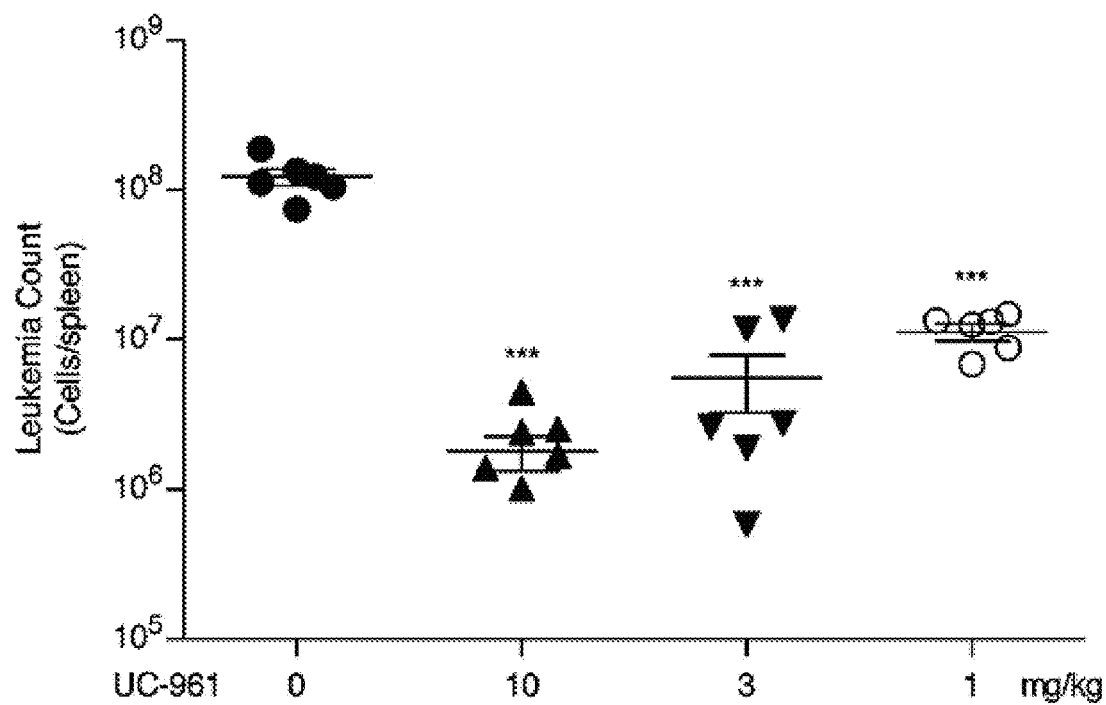

UC-961 inhibits Wnt5a-enhenced Rac1 activation and proliferation of ROR-1×TCL1 leukemia cells in the presence of ibrutinib. ROR-1×TCL1 leukemia cells were isolated from ROR-1×TCL1 double-transgenic mice that developed leukemia. Applicants pretreated ROR-1×TCL1 leukemia cells with ibrutinib or UC-961 for 2 hours and then treated the cells with or without Wnt5a recombinant protein for 30 minutes. Similar to Applicants' findings with human CLL cells, Wnt5a-induced Rac1 activation could be inhibited by UC-961 but not by ibrutinib (FIGS. 4A-4B). The combination of UC-961 with ibrutinib also inhibited Wnt5a-induced activation of Rac1 to basal levels (FIGS. 4A-4B). However, Wnt5a treatment could not induce Rac1 activation in leukemia cells derived from single-transgenic TCL1 mice that lack expression of ROR-1 (FIG. 8A). Again, ROR-1×TCL1 leukemia cells could be induced to proliferate upon culture with HeLacD154 in the presence of exogenous IL-4 and IL-10. Addition of exogenous Wnt5a treatment significantly enhanced the proportion of dividing cells and the numbers of cell divisions that could be deduced from the fluorescence of cells labeled with CFSE (FIGS. 4C-4D). Similar to human CLL cells, ROR-1×TCL1 leukemia cells co-cultured with wild-type HeLa cells were not induced to proliferate, even in the presence of IL-4/10 and/or Wnt5a (FIG. 8B). Treatment with ibrutinib partially could inhibit CD154-induced ROR-1×TCL1 leukemia-cell proliferation. UC-961, but not ibrutinib, could not inhibit the capacity of Wnt5a to enhance ROR-1×TCL1 leukemia cells proliferation in response to CD154 and IL-4/10 (FIGS. 4C-4D). On the other hand, Wnt5a did not enhance the proliferation of ROR-1-negative TCL1-leukemia cells co-cultured with HeLacD154 cells and IL-4/10.

Figure 5A:
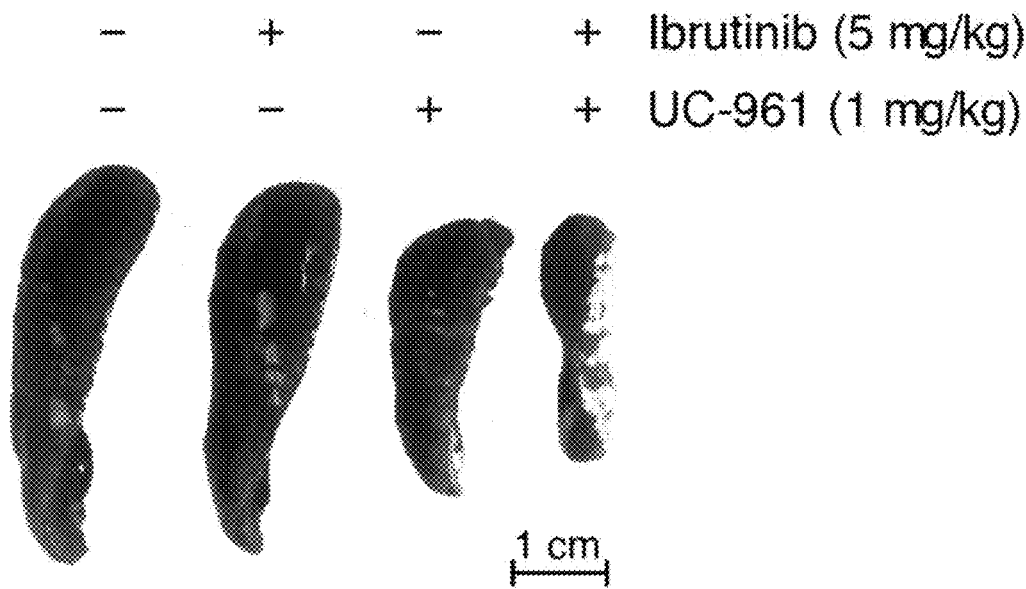
Figure 5C:
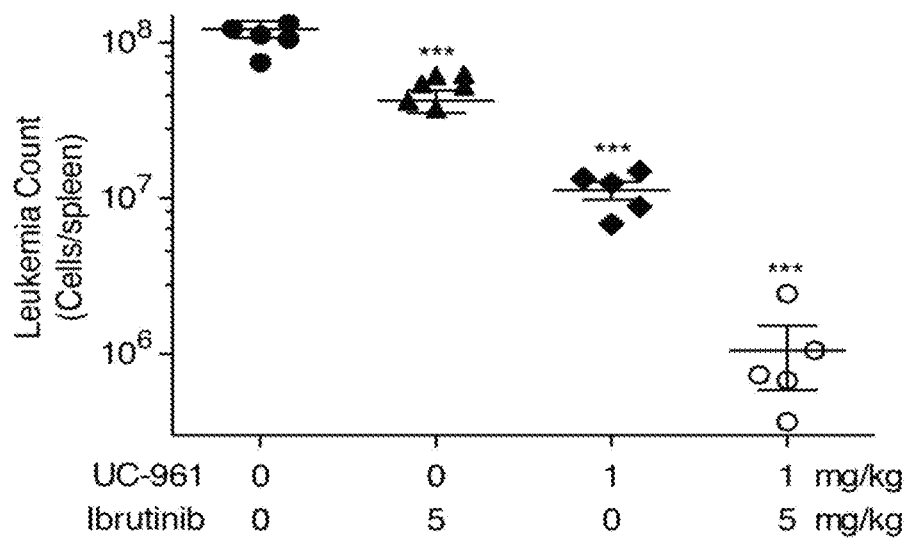

Combination of UC-961 and ibrutinib in ROR-1×TCL1 leukemia engrafted mice. Applicants examined the capacity of the combination of UC-961 with ibrutinib to inhibit engraftment of ROR-1×TCL1 leukemia cells ($CD5B220^{low}ROR-1^+$) in $Rag2^{-/-}\gamma_c^{-/-}$ mice. Applicants engrafted $Rag2^{-/-}\gamma_c^{-/-}$ mice each $2\times10^4$ROR-1×TCL1 leukemia cells and then treated the animals daily with 15, 5, 1.67 mg/kg ibrutinib, or with a single dose of 10, 3, 1 mg/kg of UC-961. After 25 days, the animals were sacrificed and the spleens were examined. Ibrutinib and UC-961 inhibited the expansion of ROR-1×TCL1 leukemia cells in a dose-dependent manner. Applicants selected the 1-mg/kg single dose of UC-961 and the 5-mg/kg daily dose of ibrutinib for combination studies. While mice treated with UC-961 or ibrutinib alone had significantly smaller spleens than did littermates without treatment, the combination treatment of UC-961 and ibrutinib caused the greatest reduction in spleen size (FIG. 5A). Applicants examined the proportions of ROR-1×TCL1 leukemia cells in the spleens via flow cytometry (FIG. 5B). The percentage and total cell numbers of ROR-1×TCL1 leukemia cells per spleen were significantly lower in mice treated with UC-961 or ibrutinib compared to mice that did not receive treatment. However, the animals treated with both UC-961 and ibrutinib had significantly fewer ROR-1×TCL1 leukemia cells per spleen than all other groups, including those treated with single agent ibrutinib or UC-961 (FIG. 5C).

Discussion.

CLL is characterized by the expansion of monoclonal, mature $CD5^+$ B cells that proliferate in tissue compartments such as the lymph node (LN) and bone marrow (BM). The differences in tumor proliferation likely account for the heterogeneous clinical course of CLL and reflect genetic differences among the malignant lymphocytes as well as the activity of external signals that drive tumor proliferation. CLL cells depend on interactions with cells and soluble factors present in the tumor microenvironment for proliferation and survival. Among the pathways that may support CLL proliferation and survival in vivo, BCR signaling appears to be one of the important. BTK is involved in the BCR signaling and is vital for many aspects of the CLL development. In the present study Applicants demonstrated that treatment of ibrutinib caused 100% inhibition of BTK, inhibited IgM-induced BCR signaling such as, calcium influx, and reduced CD154-mediated CLL proliferation.

Cellular pathways operate more like networks than superhighways. Cancers use a diversity of pathological signaling and gene regulatory mechanisms to promote their survival, proliferation, and malignant phenotypes. Applicants have reported that ROR-1 was expressed in CLL and contribute to CLL progression. The functional study revealed that Wnt5a, a ligand of ROR-1, stimulated ROR-1 to activate Rac1 in CLL cells and Wnt5a/ROR-1 signaling is important for CLL progression. Applicants examined the effects of ibrutinib on the function of Wnt5a/ROR-1 signaling, which has been shown to be important for Rac1 activation and CLL proliferation. Applicants found that even though ibrutinib can inhibit CD154-induced CLL proliferation, which is consistent with previously reported data, it was not able to inhibit Wnt5a-induced Rac1 activation and Wnt5a-enhanced CLL proliferation upon co-culture with HeLacD154 cells in the presence of exogenous IL-4/10. Moreover, Wnt-5a induced significantly Rac1 activation in patients on the treatment of ibrutinib. CLL patients show primary resistance against ibrutinib because of the resistant clones of CLL cells, this might be explained by the fact that ibrutinib did not block the Wnt5a induced signaling, which is important for CLL cell biology, especially in LN and BM microenvironment. It has been reported that Ibrutinib blocks FcγR-mediated calcium signaling and cytokine production, but it has no effect on Rac activation, which is responsible for actin polymerization and phagocytosis.

Combination therapies are often needed to effectively treat many tumors since there are multiple redundancies, or alternate routes, that may be activated in response to the inhibition of a pathway and result in drug resistance and clinical relapse. Researchers have engaged in the combination therapy using ibrutinib with other drugs for leukemia treatment. Increased Bcl-2 protein with a decline in Mcl-1 and Bcl-XL has also been observed and suggested as a survival mechanism for ibrutinib-treated CLL cells. Combination of ibrutinib with Bcl-2 inhibitor (ABT-199) showed synergistic effects on proliferation inhibition and apoptosis in mantle cell lymphoma cells through perturbation of BTK and Bcl-2 pathways. Since BTK and PI3K differentially regulate BCR signaling, the combination therapy with ibrutinib and PI3K inhibitor (idelalisib) results in a more prominent mobilization of MCL and CLL cells from their proliferation and survival promoting niches. Moreover, ibrutinib and anti-CD20 mAbs combination study showed that ibrutinib substantially reduced CD20 expression on CLL cells and subsequently diminished complement-mediated cell killing. This negative interaction between ibrutinib and anti-CD20 mAbs might reduce the efficacy of the combination therapy. All these studies indicated that it is critical to identify the possible interaction or crosstalk between the BCR signaling with alternative signaling when pursuing combination therapy with ibrutinib.

Applicants demonstrated here that UC-961 showed significantly inhibitory activity in Wnt5a-induced Rac1 activation and thereby inhibited Wnt5a-enhanced CLL proliferation. Moreover, administering a combination of UC-961 and ibrutinib eliminated leukemia cells in the recipient $Rag2^{-/-}$ $\gamma_c^{-/-}$ mice due to an additive effect, which was greater than caused by each agent alone.

UC-961 and ibrutinib enforce each other's effect. Consequently, combination therapy is expected to result in not only a reduced proliferation rate in their growth promoting niches, but also a more prominent mobilization of CLL cells from there. From the perspective of drug clearance and protein turnover, the effect may also be stronger and prolonged because BTK and ROR-1 do not have to be fully occupied when the combination is used. Furthermore, lower doses can be given, which might be beneficial for the efficacy/toxicity ratio. Of major importance, however, targeting more than one key component of a pathway may overcome innate and overcome or prevent acquired (mono) therapy resistance. For example, UC-961 may still be beneficial in the ibrutinib-treated patients with mutation at the ibrutinib-binding site on BTK, mutation in additional molecules in the BTK axis such as PLCγ2, and SF3B1 mutation, which is associated with poor prognosis was identified.

Taken together, Applicants' use of UC-961 in in vitro and in vivo systems using CLL or ROR-1×TCL1 leukemia cells support the potential of UC-961 as a therapeutic drug and deserves further investigation of its combination therapy with ibrutinib for CLL and possibly other ROR-1 expressing B cell malignancies that depend upon active BCR signaling and/or the tumor microenvironment.

Methods.

Cells and Sample Preparation

CLL specimens. Blood samples were collected from CLL patients at the University of California San Diego Moores Cancer Center. PBMCs were isolated by density centrifugation with Ficoll-Paque PLUS (GE Healthcare Life Sciences), and suspended in 90% fetal bovine serum (FBS) (Omega Scientific) and 10% DMSO (Sigma-Aldrich) for viable storage in liquid nitrogen. Samples with >95% $CD19^+$ $CD5^+$ CLL cells were used without further purification throughout this study.

Ibrutinib occupancy assay. CLL cells were treated with increasing concentrations of ibrutinib (0, 0.25, 0.5 or 1 μM) for 1 hour. Cells were then washed in phosphate buffered saline and stored at −80° C. until a BTK occupancy assay was performed as described. BTK occupancy was compared using GraphPad Prism version 6.0 (GraphPad, San Diego, Calif.).

Calcium Flux assay. CLL cells were incubated with 0, 0.25, 0.5 or 1.0 μM ibrutinib for 30 min, and then were loaded with 2 mM Fluo-4AM (Molecular Probes) in Hanks Balanced Salt Solution (HBSS), lacking $Ca^{2+}$ and $Mg^{2+}$. Cells were kept at 37° C. for stimulation with anti-human IgM $F(ab)_2$. Calcium release was monitored by flow cytometry analysis, as described.

Cell proliferation assay. Primary CLL or ROR-1×TCL1 leukemia cell proliferation assay was performed as described. Leukemia cells were labeled by carboxyfluorescein succinimidyl ester (CFSE, Life Technologies) and plated at $1.5 \times 10^6$/well/ml in a 24-well tray on a layer of irradiated HeLacD154 cells (8000, Rad; 80 Gray) at a CLL/HeLacD154 cell ratio of 15:1 in complete RPMI-1640 medium supplemented 5 ng/mL of recombinant human interleukin (IL)-4 (R&D Systems) and 15 ng/mL recombinant human IL-10 (R&D Systems). Wnt5a (200 ng/ml, R&D Systems) or UC-961 (10 μg/ml) as indicated in the text. CFSE-labeled CLL cells were analyzed by flow cytometry; Modfit LT software (version 3.0, Verity Software House) was used for analysis of cell proliferation as previously described.

Rac1 activation assay. Rac1 activation assay reagents were purchased from Cytoskeleton and used as per manufacturer's instruction. Briefly, GTP-bound active Rac1 were pulled down with PAK-PBD beads, and then subjected to immunoblot analysis. Immunoblots of whole-cell lysates were used to assess for total Rac1. The integrated optical density (IOD) of bands was evaluated by densitometry and analyzed using Gel-Pro Analyzer 4.0 software (Media Cybernetics, MD).

Immunoblot analysis. Western blot analysis was performed as described. Equal amounts of total protein from each sample were fractionated by SDS-PAGE and blotted onto polyvinylidene difluoride membrane. Western blot analysis was performed using primary mAb specific for Rac1, which were detected using secondary antibodies conjugated with horseradish peroxidase (Cell Signaling Technology).

Human CLL patient derived xenograft study. Six- to eight-week-old $Rag2^{-/-}\gamma_c^{-/-}$ mice (initially obtained from Catriona Jamieson, University of California San Diego) were housed in laminar-flow cabinets under specific pathogen-free conditions and fed ad libitum. Applicants injected $2\times10^7$ viable primary CLL cells in AIM-V medium into the peritoneal cavity of each mouse. On the following day, one mg/kg UC-961 was injected once by i.p. and ibrutinib was administrated daily at 15 mg/kg by oral gavage. Seven days later, peritoneal lavage (PL) was extracted by injecting the cavity with a total volume of 12 mL of Dulbecco's PBS. Total recovery of the PL cells was determined by using Guava counting. Subsequently, cells were blocked with both mouse and human Fc blocker for 30 min at 4° C., stained with various human cell-surface markers (e.g., CD19, CD5, CD45), and then processed for flow cytometric analysis. Applicants calculated the number of CLL cells in each PL by multiplying the percentage of CLL cells in the PL by the total PL cell counts. Residual leukemia cells from human IgG-treated mice were set as baseline at 100%. Each treatment group included at least 6 mice, and the data were presented as mean±SEM.

ROR-1×TCL1 leukemia adoptive transfer study. Applicants evaluated the anti-leukemia activity of the combination of UC-961 with ibrutinib in immune-deficient $Rag2^{-/-}\gamma_c^{-/-}$ mice. ROR-1×TCL1 leukemia B cells ($CD5B220^{low}ROR-1^+$) were isolated from the spleen, enriched via density gradient centrifugation, suspended in sterile PBS, injected i.v. into $Rag2^{-/-}\gamma_c^{-/-}$ recipient mice at $2\times10^4$ cells per animal. Samples used for transplantation were verified by flow cytometry to be >95% leukemia B cells. For dose dependent therapy of UC-961, recipient mice received either no treatment, or one dose i.v. injections of 10 mg/kg, 3 mg/kg and 1 mg/kg of UC-961 on day 1. For dose dependent therapy of ibrutinib, recipient mice received either no treatment, or daily p.o. injections of 15 mg/kg, 5 mg/kg and 1.67 mg/kg of ibrutinib, beginning on day 1. For combination therapy, recipient mice received either no treatment, or one dose i.v. injections of 1 mg/kg of UC-961 and/or daily p.o. 5 mg/kg of ibrutinib, beginning on day 1. All mice were sacrificed on day 25 and single-cell suspensions of splenocytes were purged of red blood cells by hypotonic lysis in ammonium-chloride-potassium (ACK) lysis solution, washed, suspended in 2% (wt/vol) BSA (Sigma) in PBS (pH=7.4) and stained for surface expression of CD3 (17A2), CD5 (53-7.3), B220 (RA3-6B2), and ROR-1 (4A5) using optimized concentrations of fluorochrome-conjugated mAbs. Cells were examined by four-color, multiparameter flow cytometry using a dual-laser FACSCalibur (BD) and the data were analyzed using FlowJo software (TreeStar). The total number of leukemia cells per spleen was calculated by determining the percent of $CD5B220^{low}ROR-1^+$ cells of total lymphocytes by flow cytometry and multiplying this number by the total spleen cell count.

Statistics. Data are presented as mean±SEM as indicated, for data sets that satisfied conditions for a normal distribution, as determined by the Kolmogorov-Smirnov test. The statistical significance of the difference between means was assessed by one-way ANOVA with Tukey's multiple comparisons test. P values less than 0.05 were considered significant. Analysis for significance was performed with GraphPad Prism 6.0 (GraphPad Software Inc.).

Example 2. Combination Studies

CLL cells were treated with different BCR inhibitors and examined for ROR-1 expression, ROR-1 expression was significantly induced following BCR inhibitors treatments. Applicants cultured CLL cells that had increased ROR-1 expression induced by BCR signaling inhibitors in the peritoneal cavity of immunodeficient Rag2/common-gamma-chain knockout mice ($Rag2^{-/-}\gamma\gamma_c^{-/-}$), which subsequently were treated with control Ig, anti-ROR-1 antibody, Ibrutinib, or combination of anti-ROR-1 antibody and Ibrutinib. CLL cells were more sensitive to treatment with combination of anti-ROR-1 antibody and Ibrutinib than with treatment with anti-ROR-1 antibody or Ibrutinib only. The capacity of combination of anti-ROR-1 antibody and Ibrutinib to inhibit the adoptive transfer of human-ROR-1 expressing murine leukemia cells was tested in immunodeficient recipient mice. Six $RAG2^{-/-}\gamma_c^{-/-}$ mice were injected intravenously with 1 mg/kg of humanized anti-human ROR-1 mAb UC-961. Two hours later, all mice were given an intravenous injection of $1\times10^4$ $CD5B220^{lo}$ human ROR-$1^+$ murine leukemia cells derived from a ROR-1×TCL1 transgenic mouse. Ibrutinib daily treatment was started on the next day after leukemia xenograft. When compared to control animals, animals treated by single agent, the combination treatment of anti-ROR-1 antibody and Ibrutinib resulted in a over 90% reduction of leukemic cells in the spleen, the major organ of accumulation for these malignant cells.

Figure 9:
FIG. 9. ROR-1 was induced by BCR signaling inhibitors.

As depicted in FIG. 9, CLL cells were treated with different BCR inhibitors and examined for ROR-1 expression, ROR-1 expression was significantly induced following BCR inhibitor treatment.

Figure 10:
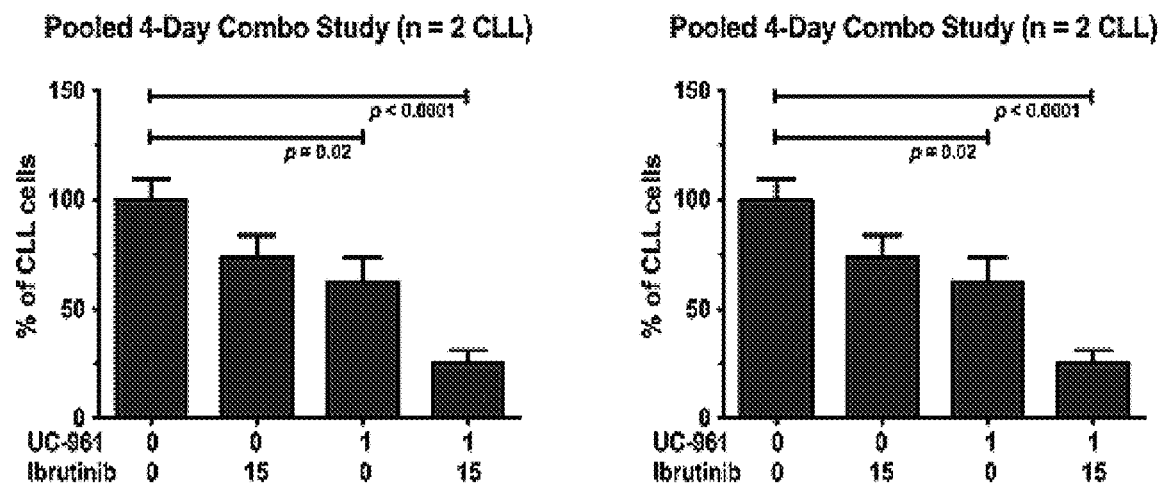
FIG. 10. Additive effect of anti-ROR-1 antibody combined with Ibrutinib on clearing CLL cells in Niche dependent animal model.

As depicted in FIG. 10, Applicants cultured CLL cells that had increased ROR-1 expression induced by BCR signaling inhibitors in the peritoneal cavity of immunodeficient Rag2/common-gamma-chain knockout mice ($Rag2^{-/-}\gamma_c^{-/-}$), which subsequently were treated with control Ig, anti-ROR-1 antibody, Ibrutinib, or combination of anti-ROR-1 antibody an Ibrutinib. CLL cells were more sensitive to treatment with combination of anti-ROR-1 antibody and Ibrutinib than with treatment with anti-ROR-1 antibody or Ibrutinib only.

Figure 11:
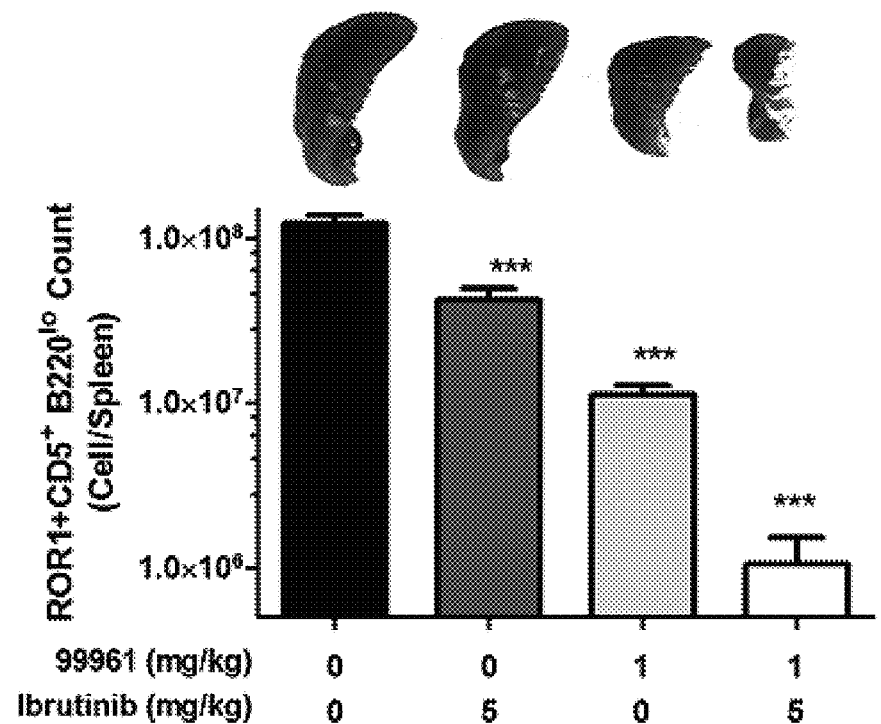
FIG. 11. Additive effect of anti-ROR-1 antibody combined with Ibrutinib on ROR-1×TCL1 mice leukemia.

As depicted in FIG. 11, $Rag2^{-/-}\gamma_c^{-/-}$ mice were given an intravenous injection of $1\times10^4$ $CD5B220^{lo}$ human ROR-$1^+$ murine leukemia cells derived from a ROR-1×TCL1 transgenic mouse, which subsequently were treated with control Ig, anti-ROR-1 antibody, Ibrutinib, or combination of anti-ROR-1 antibody and Ibrutinib next day. The combination treatment of anti-ROR-1 antibody and Ibrutinib resulted in a significant reduction of leukemic cells in the spleen, the major organ of accumulation for these malignant cells, compared with treatment of anti-ROR-1 antibody or Ibrutinib only.

Example 3. Cirmtuzumab Inhibits WNT5A-Induced RAC1 Activation in Chronic Lymphocytic Leukemia Treated with Ibrutinib Abstract. Signaling via the B cell receptor (BCR) plays an important role in the pathogenesis and progression of chronic lymphocytic leukemia (CLL). This is underscored by the clinical effectiveness of ibrutinib, an inhibitor of Bruton's tyrosine kinase (BTK) that can block BCR-signaling. However, ibrutinib cannot induce complete responses (CR) or durable remissions without continued therapy, suggesting alternative pathways also contribute to CLL growth/survival that are independent of BCR-signaling. ROR-1 is a receptor for Wnt5a, which can promote activation of Rac1 to enhance CLL-cell proliferation and survival. In this study, Applicants found that CLL cells of patients treated with ibrutinib had activated Rac1. Moreover, Wnt5a could induce Rac1 activation and enhance proliferation of CLL cells treated with ibrutinib at concentrations that were effective in completely inhibiting BTK and BCR-signaling. Wnt5a-induced Rac1 activation could be blocked by cirmtuzumab (UC-961), an anti-ROR-1 mAb. Applicants found that treatment with cirmtuzumab and ibrutinib was significantly more effective than treatment with either agent alone in clearing leukemia cells in vivo. This study indicates that cirmtuzumab may enhance the activity of ibrutinib in the treatment of patients with CLL or other ROR-1$^+$ B-cell malignancies.

Introduction. CLL cells depend on interactions with cells and soluble factors present in the tumor microenvironment for proliferation and survival. Among the pathways that may support CLL proliferation and survival in vivo, BCR-signaling plays a prominent role. Crosslinking of the BCR leads to phosphorylation of CD79α/β and Src family kinase LYN, resulting in the recruitment and activation of the tyrosine kinase Syk, which induces a cascade of downstream signaling events, leading to enhanced B-cell survival. The importance of this cascade in CLL biology appears underscored by the clinical activity of small-molecule inhibitors of intracellular kinases, which play critical roles in BCR-signaling, such as SYK, phosphoinositide 3-kinase (PI3K), or Bruton's tyrosine kinase (BTK). Ibrutinib is a small molecule inhibitor of BTK that has proven highly effective in the treatment of patients with CLL. However, despite having excellent clinical activity, ibrutinib generally cannot eradicate the disease or induce durable responses in the absence of continuous therapy.

The failure of ibrutinib to induce complete responses could be due to alternative survival-signaling pathways, which are not blocked by inhibitors of BTK. One such pathway is that induced by signaling through ROR-1, an oncoembryonic antigen expressed on CLL cells, but not on normal postpartum tissues. Applicants found that ROR-1 could serve as a receptor for Wnt5a, which could induce non-canonical Wnt-signaling that activates Rho GTPases, such as Rac1, and enhance leukemia-cell proliferation and survival. Activation of Rac1 by Wnt5a could be inhibited by an anti-ROR-1 mAb, cirmtuzumab (UC-961), which is a first-in-class humanized monoclonal antibody currently undergoing evaluation in clinical trials for patients with CLL.

In this study, Applicants investigated whether Wnt5a/ROR-1 signaling was affected by treatment with ibrutinib and examined the activity of ibrutinib and cirmtuzumab on CLL cells in vitro and in vivo.

Materials and Methods

Blood Samples and Animal. Blood samples were collected from CLL patients at the University of California San Diego Moores Cancer Center who satisfied diagnostic and immunophenotypic criteria for common B-cell CLL, and who provided written, informed consent, in compliance with the Declaration of Helsinki and the Institutional Review Board (IRB) of the University of California San Diego (IRB approval number 080918). PBMCs were isolated as described. All experiments with mice were conducted in accordance with the guidelines of the National Institutes of Health for the care and use of laboratory animals, and University of California San Diego approved study protocol. All mice were age and sex matched.

BTK-occupancy Assay. CLL cells were treated with increasing concentrations of ibrutinib (0, 0.25, 0.5 or 1 µM) for 1 hour. Cells were then washed in phosphate buffered saline and stored at −80° C. until a BTK occupancy assay was performed as described. BTK occupancy was compared using GraphPad Prism version 6.0 (GraphPad, San Diego, Calif.).

Calcium Flux Assay. CLL cells were incubated with 0, 0.25, 0.5, or 1.0 µM ibrutinib for 30 min, and then were loaded with 2 mM Fluo-4AM (Molecular Probes) in Hanks Balanced Salt Solution (HBSS), lacking $Ca^{2+}$ and $Mg^{2+}$. Cells were kept at 37° C. for stimulation with anti-human IgM F(ab)$_2$. Calcium release was monitored by flow cytometry analysis, as described.

Rac1 Activation Assay. Reagents for Rac1 activation assay were made in Applicants' lab, as described previously. The Rac1 pull-down and immunoblot analyses were performed as described.

Figure 18A:
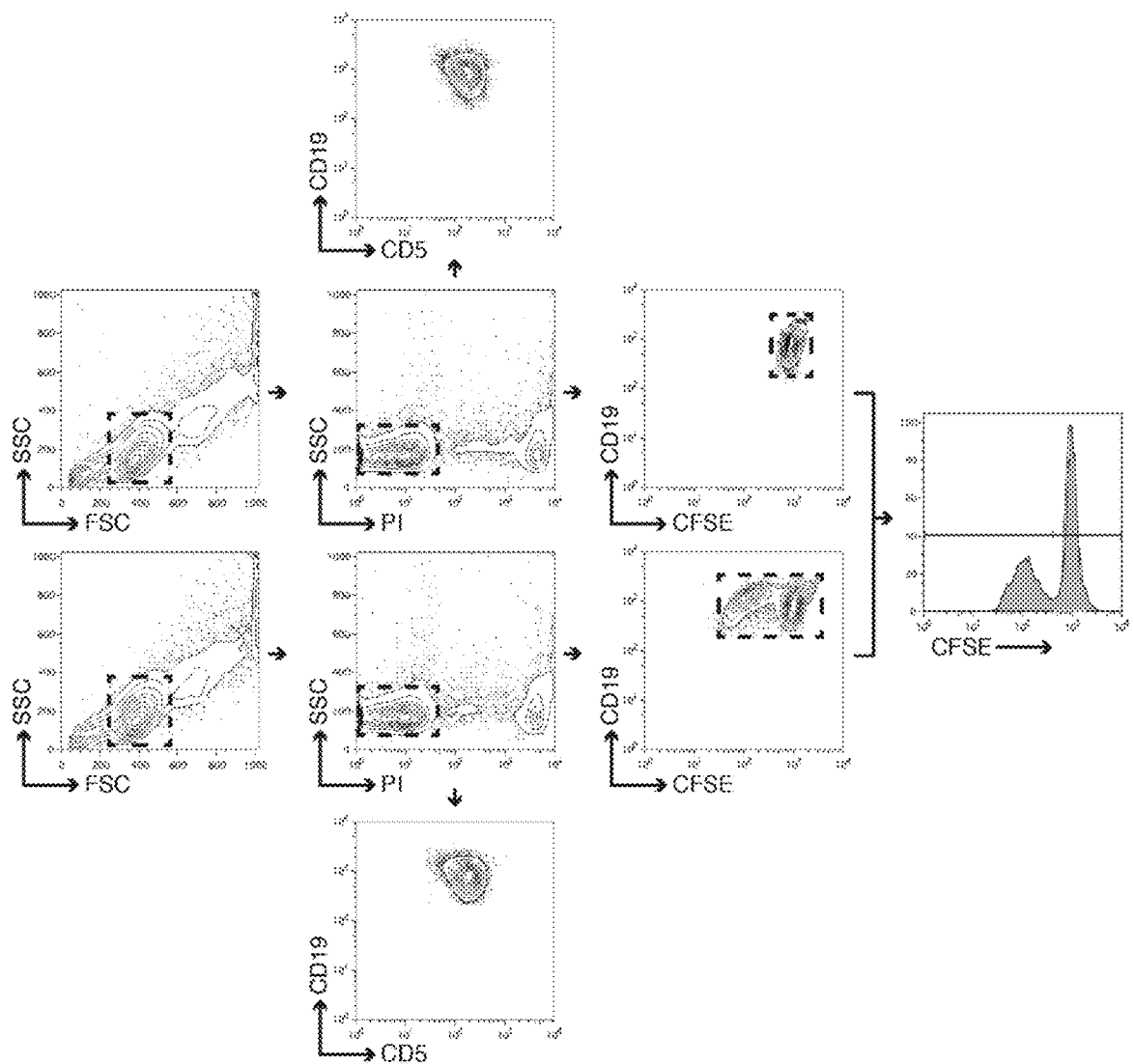
FIGS. 18A-18B. CFSE Assay For CLL Proliferation Induced By Wnt5a Without CD154.
Figure 18B:
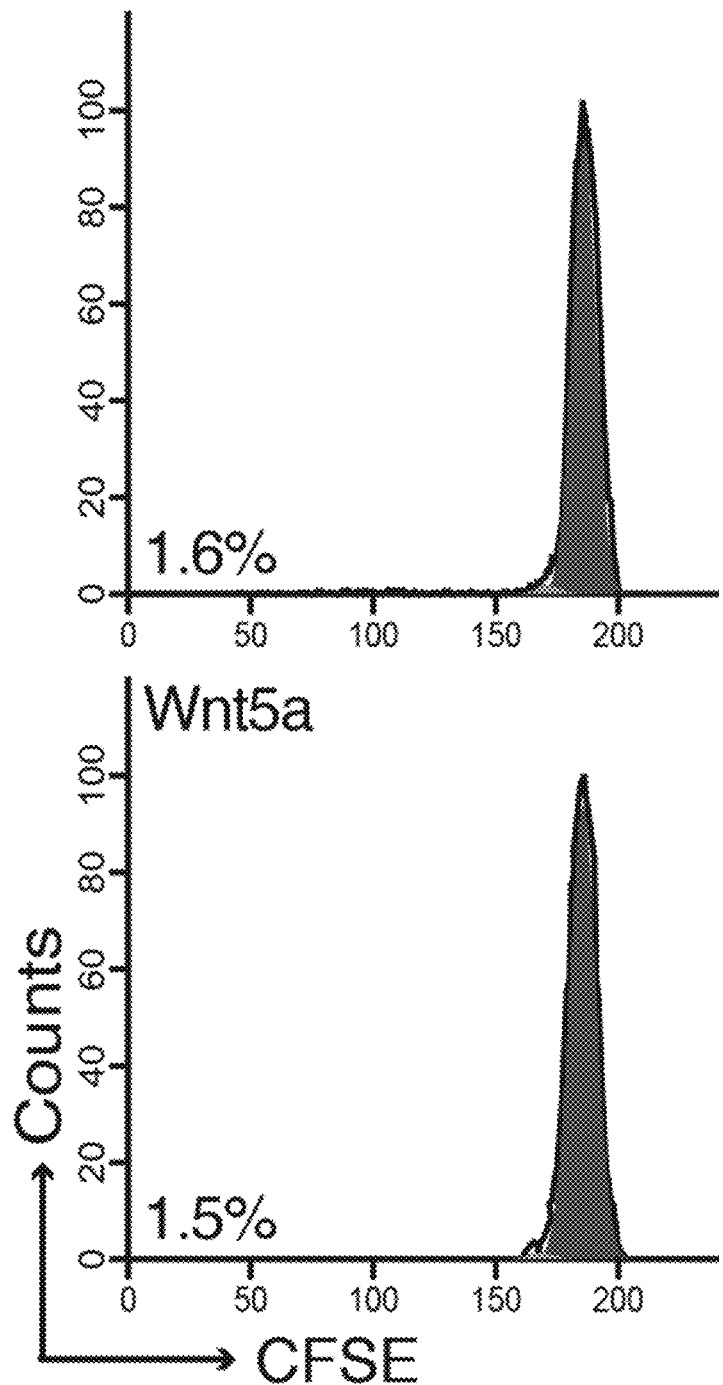

Cell Proliferation Assay. Applicants performed leukemia cell proliferation assay according to previous described. For these analyses Applicants gated on viable CD5$^+$CD19$^+$ cells using their characteristic light scatter and capacity to exclude PI (FIGS. 18A-18B).

Cell Cycle Analyses. Leukemia cells (1×10$^7$) were suspended in 100 µl of PBS and fixed overnight at 4° C. by adding 1 ml cold ethanol. Cells were spin at 700×g for 2 min and washed twice with PBS containing 1% BSA. The pelleted cells were then suspended in 500 µl of PBS containing 1% BSA and 1 µl of RNase (100 mg/ml); RNase was added to digest RNA. PI solution (0.5 mg/ml in 38 mM sodium citrate, pH 7.0), 1 µl boiled RNase A (100 mg/ml), and PI-staining solution (0.5 mg/ml in 38 mM sodium citrate, pH 7.0; 60 µl) were added to cells and incubated in the dark for 1 hour at room temperature. Immediately thereafter, the cells were analyzed via flow cytometry using a FACSArray (Becton Dickinson), and data were analyzed using FlowJo software (Tree Star Inc.).

CLL Patient Derived Xenografts. Six- to eight-week-old Rag2$^{-/-}$γ$_c$$^{-/-}$ mice (initially obtained from Catriona Jamieson, University of California San Diego) were housed in laminar-flow cabinets under specific pathogen-free conditions and fed ad libitum. Applicants injected 2×10$^7$ viable primary CLL cells in AIM-V medium into the peritoneal cavity of each mouse. On the following day, one mg/kg cirmtuzumab was injected once by i.p. and ibrutinib was administrated daily at 15 mg/kg by oral gavage. Seven days later, peritoneal lavage (PL) was extracted by injecting the cavity with a total volume of 12 mL of Dulbecco's PBS. Total recovery of the PL cells was determined by using Guava counting. Subsequently, cells were blocked with both mouse and human Fc blocker for 30 min at 4° C., stained with various human cell-surface markers (e.g., CD19, CD5, CD45), and then processed for flow cytometric analysis. Applicants calculated the number of CLL cells in each PL by multiplying the percentage of CLL cells in the PL by the total PL cell counts. Residual leukemia cells from human IgG-treated mice were set as baseline at 100%. Each treatment group included at least 5 mice, and the data were presented as mean±SEM.

ROR-1×TCL1 Leukemia Adoptive Transfer Study. Applicants evaluated the anti-leukemia activity of the combination of cirmtuzumab with ibrutinib in immunodeficient Rag2$^{-/-}\gamma_c^{-/-}$ or immunocompetent ROR-1-transgenic mice, as previous described.

Statistical Analyses. Data are shown as mean±SEM. Normal distribution of data sets was determined by the Kolmogorov-Smirnov test. The statistical significance of the difference between means was assessed by one-way ANOVA with Tukey's multiple comparisons test. Applicants used GraphPad Prism 6.0 (GraphPad Software Inc.) to calculate the level of significance using the statistical method described in the text. A p≤0.05 was considered significant.

Results

Figure 12A:
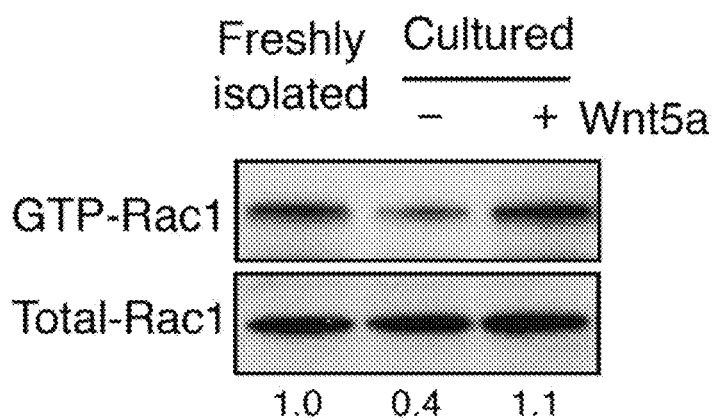
FIGS. 12A-12F. Cirmtuzumab inhibits Wnt5a-Induced Rac1 activation in ibrutinib-treated CLL cells.
Figure 12B:
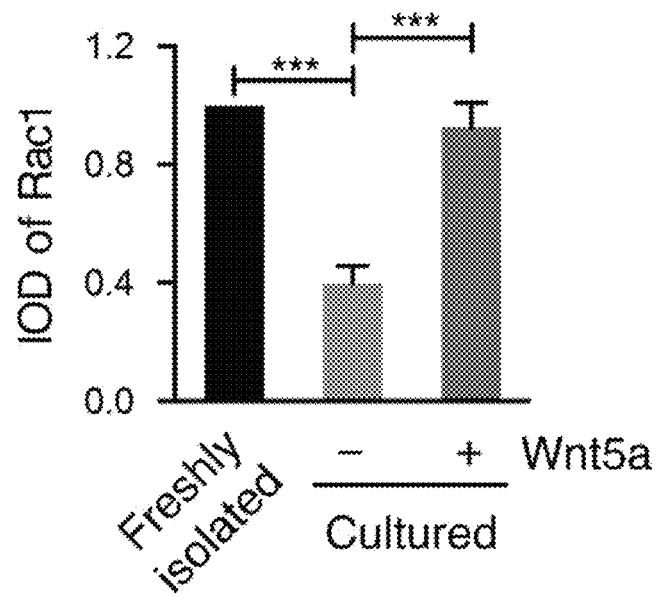
Figure 12C:
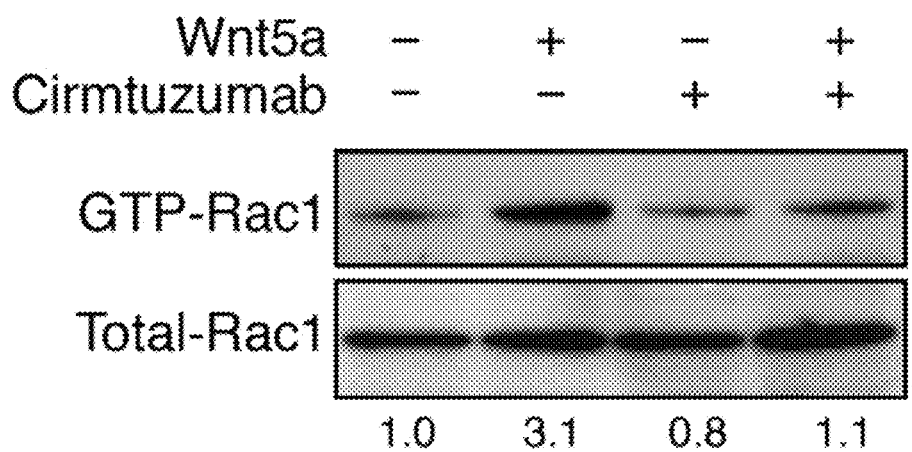
Figure 12D:
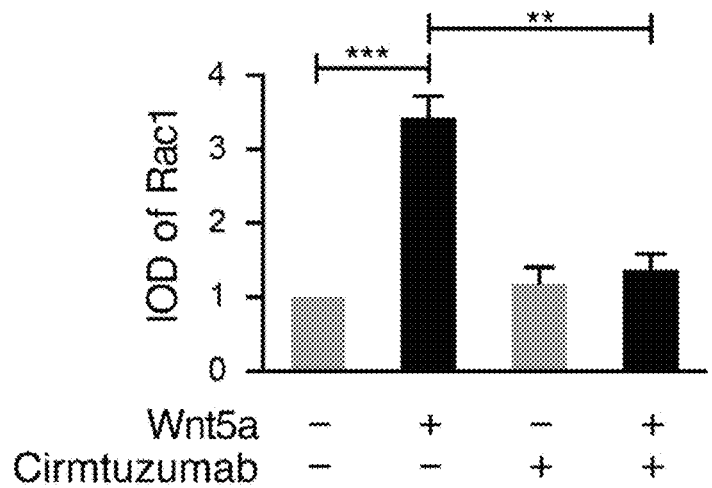

Ibrutinib fails to inhibit Wnt5a-induced Rac1 activation in CLL. Applicants examined the blood mononuclear cells of patients who were taking ibrutinib at the standard dose of 420 mg per day. Freshly isolated CLL cells had activated Rac1, which diminished over time in culture in serum-free media unless provided with exogenous Wnt5a (FIGS. 12A-12B), as noted for the CLL cells of patients not taking ibrutinib. Moreover, the CLL cells from ibrutinib-treated patients were incubated with or without Wnt5a and/or cirmtuzumab. Immunoblot analysis showed that Wnt5a induced Rac1 activation in CLL cells from all patients examined, whereas treatment with cirmtuzumab inhibited Wnt5a-induced Rac1 activation (FIGS. 12C-12D). These results indicate that therapy with ibrutinib does not inhibit ROR-1-dependent, Wnt5a-induced Rac1 activation.

Applicants examined whether treatment of CLL cells with ibrutinib in vitro could inhibit Wnt5a-induced Rac1 activation in CLL. For this, Applicants incubated CLL cells collected from untreated patients with ibrutinib at concentrations of 0, 0.25, 0.5, or 1.0 μM for 2 hours and then treated the cells with exogenous Wnt5a for 30 minutes. Immunoblot analysis demonstrated that ibrutinib could not block Wnt5a-induced Rac1 activation, even at ibrutinib concentrations of 1 (FIG. 6A), which is in large excess of what is required to achieve 100% occupancy of BTK and inhibition of BTK activity (FIG. 6B). On the other hand, Applicants noted that ibrutinib at concentrations as low as 0.25 μM inhibited the calcium flux induced by anti-IgM (FIG. 6C), without acutely affecting CLL-cell viability (FIG. 6D).

Figure 12E:
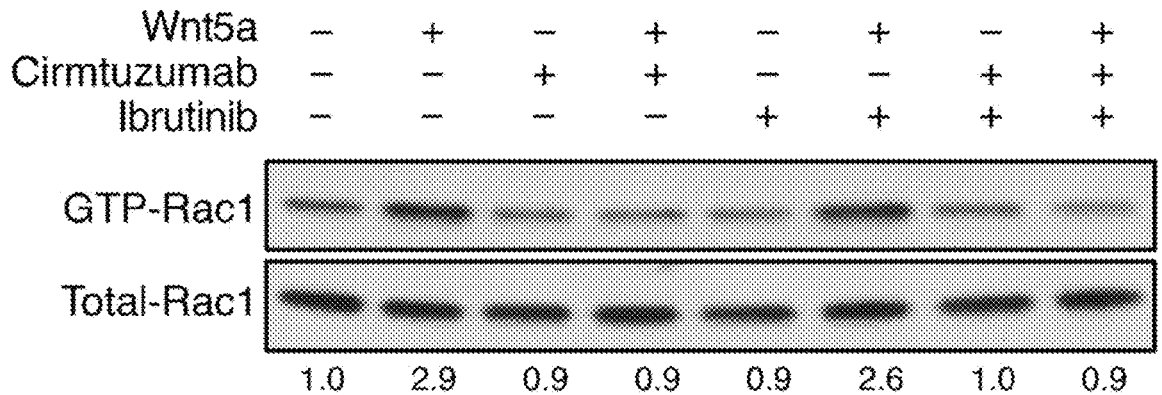
Figure 12F:
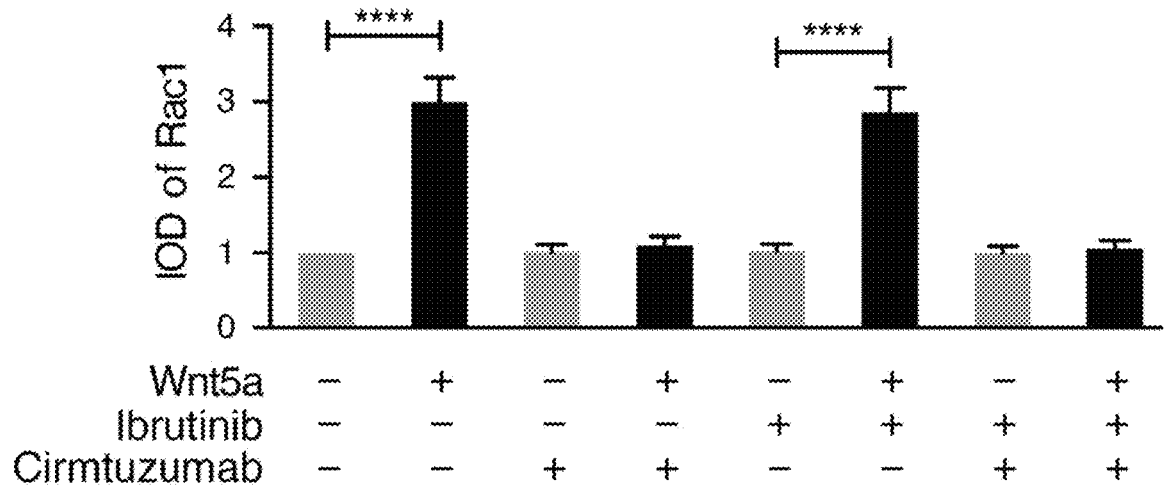

The peak plasma concentration of ibrutinib in patients treated with this drug is approximately 0.5 μM, a concentration that can affect 100% occupancy and inhibition of BTK. Therefore, ibrutinib was used at 0.5 μM for subsequent studies. Applicants examined for Wnt5a-induced Rac1 activation with or without ibrutinib and/or cirmtuzumab. CLL cells were cultured with ibrutinib, cirmtuzumab, or both ibrutinib and cirmtuzumab for 2 hours, and then stimulated with exogenous Wnt5a for 30 minutes. For comparison, cells from the same CLL sample were cultured without Wnt5a in parallel. Treatment of CLL cells with Wnt5a induced activation of Rac1 to levels that were significantly higher than that of CLL cells that were not treated with Wnt5a (FIGS. 12E-12F). Treatment with cirmtuzumab, but not ibrutinib, could inhibit Wnt5a-induced Rac1 activation in CLL cells (FIGS. 12E-12F). As expected, ibrutinib did not block the capacity of cirmtuzumab to inhibit Wnt5a-induced Rac1 activation (FIGS. 12E-12F).

Figure 13A:
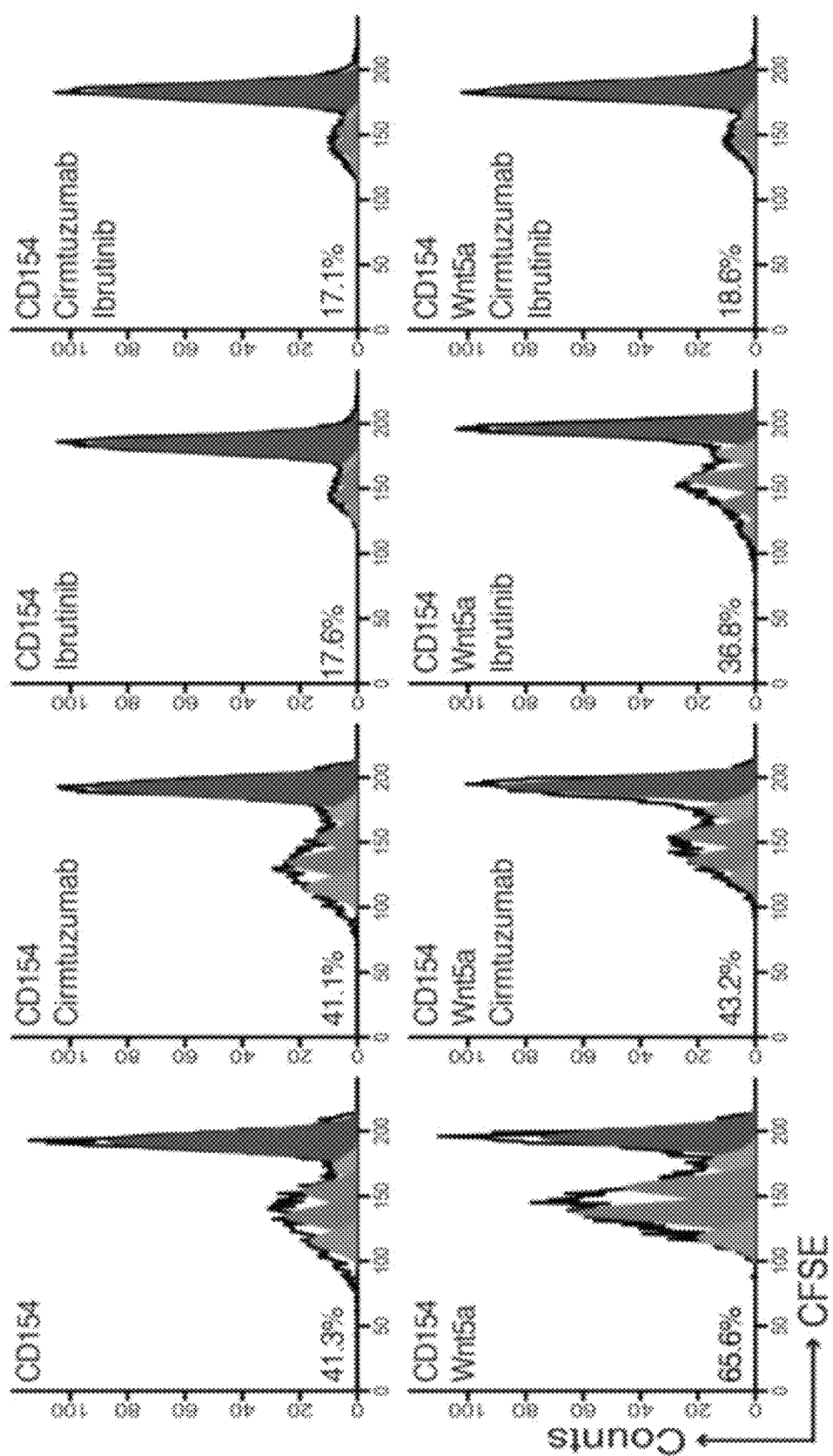
FIGS. 13A-13D. Cirmtuzumab inhibits Wnt5a-enhanced proliferation in ibrutinib-treated CLL Cells.
Figure 13B:
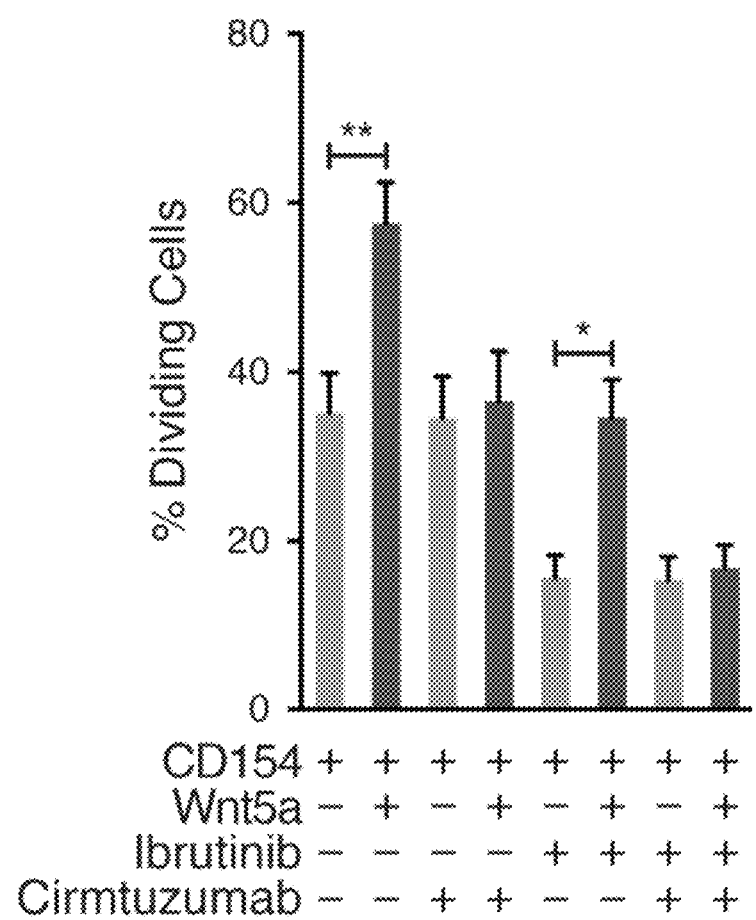
Figure 13C:
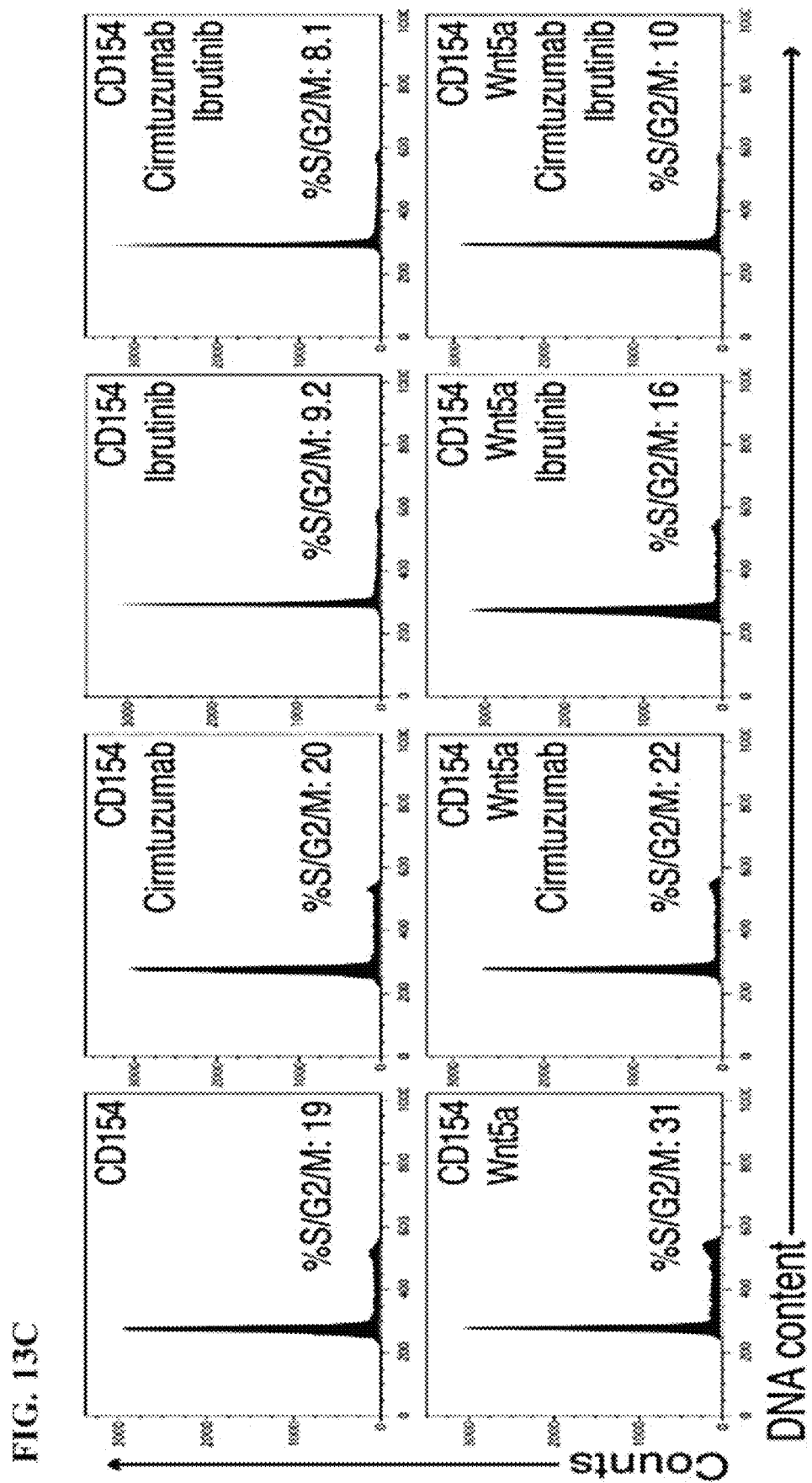
Figure 13D:
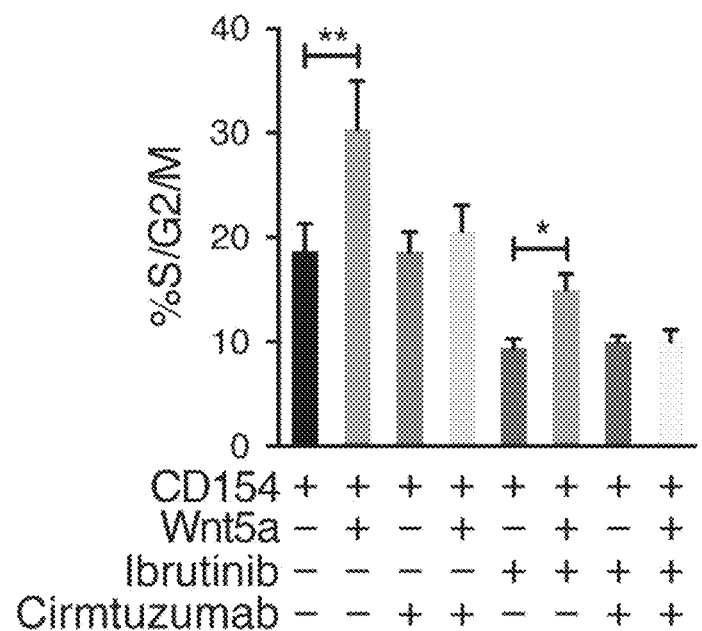

Cirmtuzumab inhibits Wnt5a-enhanced proliferation of CLL cells treated with ibrutinib. Activation of Rac1-GTPase can enhance proliferation, whereas loss of Rac1 results in impaired hematopoietic-cell growth. Applicants induced proliferation of CLL cells by co-culturing leukemia cells with HeLa cells expressing CD154 (HeLacD154) and recombinant interleukin (IL)-4 and IL-10. Addition of exogenous Wnt5a to co-cultures of CLL cells with HeLacD154 cells and IL-4/10 significantly enhanced the proportion of dividing CLL cells. Treatment of the CLL cells with cirmtuzumab, but not ibrutinib, could block Wnt5a-enhanced proliferation of CLL cells (FIG. 13A). The same effects were observed for CLL cells of different patients (n=6) (FIG. 13B). IL4/10 and/or Wnt5a alone could not induce CLL-cell proliferation (FIGS. 18A-18B). Furthermore, cell-cycle analysis on permeabilized leukemia cells with propidium iodide (PI) demonstrated that Wnt5a enhanced the fraction of CD154-stimulated leukemia cells in S/G2/M (FIGS. 13C-13D). The capacity of Wnt5a to enhance the proportion of cells in S/G2/M could be inhibited by treatment with cirmtuzumab, but not ibrutinib (FIGS. 13C-13D).

Figure 14A:
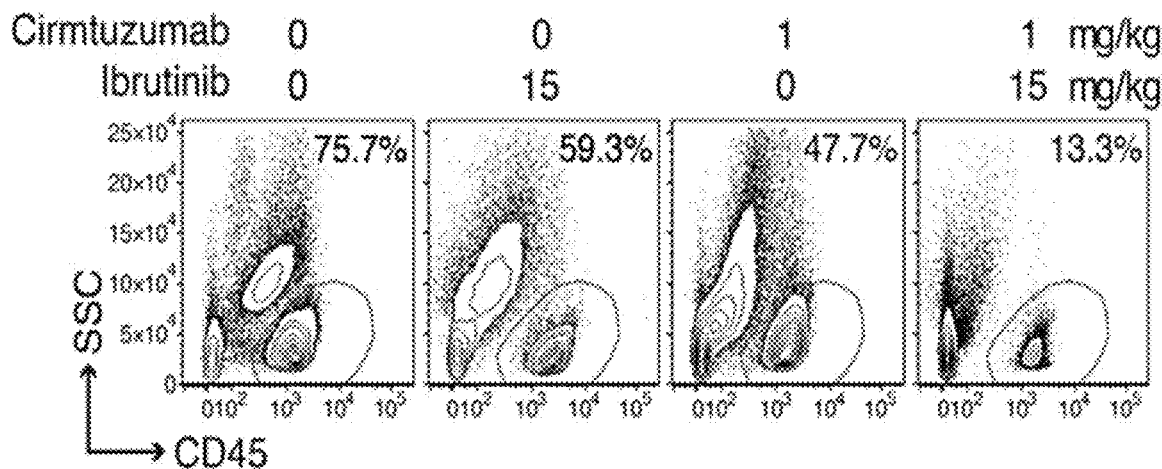
FIGS. 14A-14B. Effect of treatment with cirmtuzumab and/or ibrutinib on CLL patient derived xenografts.
Figure 14B:
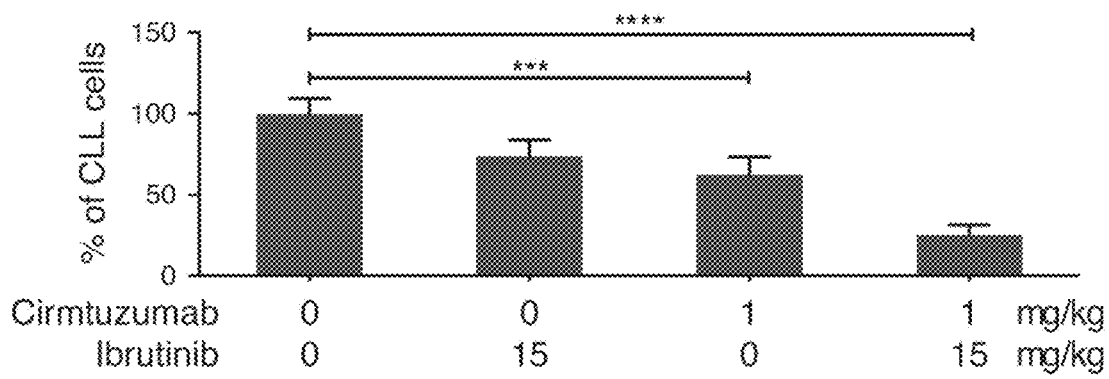

Activity of cirmtuzumab and/or ibrutinib in CLL patient-derived xenografts. Applicants transferred CLL cells into the peritoneal cavity of immunodeficient Rag2$^{-/-}\gamma_c^{-/-}$ mice, and examined whether treatment with ibrutinib and/or cirmtuzumab could deplete CLL cells in vivo. For this, Applicants injected 1×10$^7$ viable primary CLL cells in AIM-V medium into the peritoneal cavity of each mouse. One day later, the mice were provided no treatment or daily doses of ibrutinib at 15 mg/kg via oral gavage, and/or a single dose of cirmtuzumab at 1 mg/kg via i.p. injection. After 7 days, the CLL cells were harvested via peritoneal lavage (PL) and the proportions of CLL cells in the harvested peritoneal cells were examined by flow cytometry (FIG. 14A). The percentages and total numbers of CLL cells in PL were significantly lower in mice treated with cirmtuzumab or ibrutinib than in mice that did not receive any treatment. However, significantly fewer CLL cells were found in the PL of mice treated with cirmtuzumab and ibrutinib than in the PL of mice treated with either agent alone (FIG. 14B).

Figure 7C:
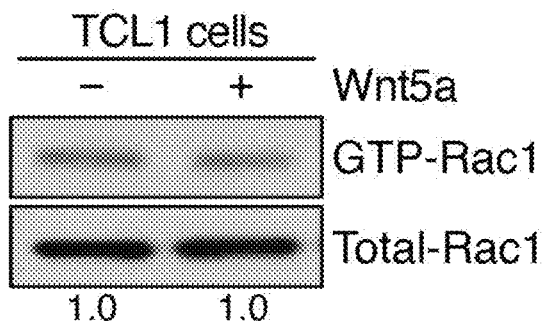
Figure 7E:
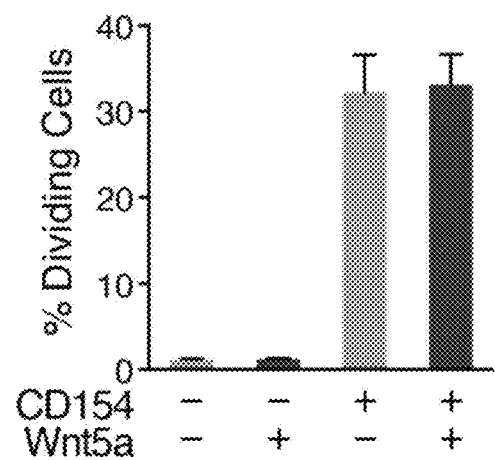
Figure 15A:
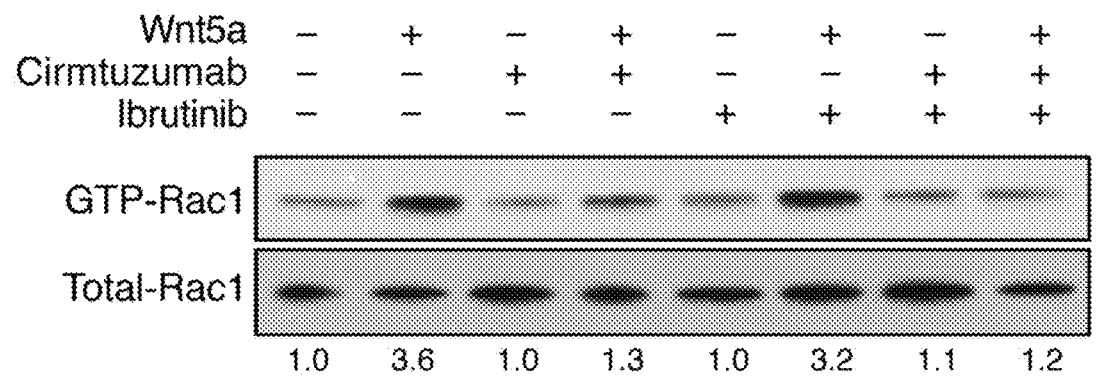
FIGS. 15A-15C. Cirmtuzumab inhibits Wnt5a-enhanced proliferation in ibrutinib-treated ROR-1×TCL1 leukemia cells.
Figure 15B:
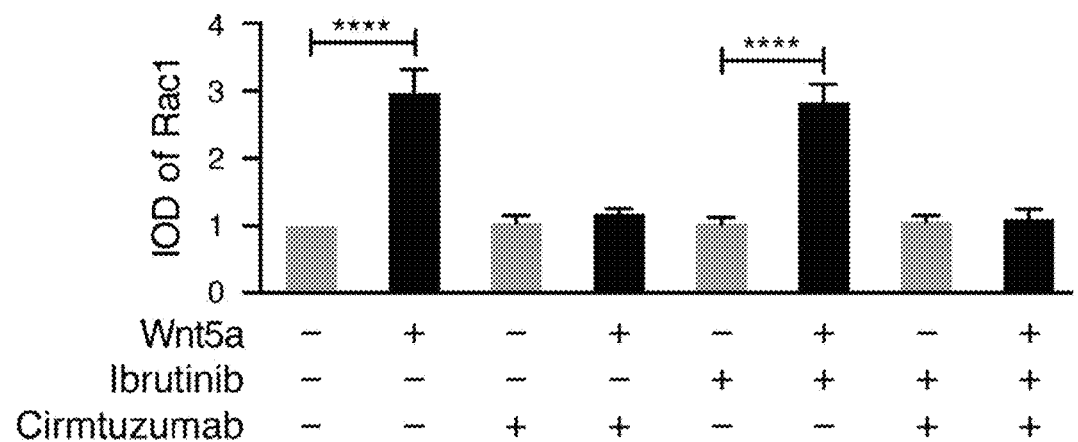

Cirmtuzumab, but not ibrutinib, inhibits Wnt5a-enhanced Rac1 activation and proliferation of ROR-1×TCL1 leukemia cells. ROR-1×TCL1 leukemia cells were isolated from ROR-1×TCL1 double-transgenic mice that developed ROR-1$^+$ leukemia. Applicants pretreated ROR-1×TCL1 leukemia cells with ibrutinib or cirmtuzumab for 2 hours and then cultured the cells with or without Wnt5a for 30 minutes. Similar to findings with human CLL cells, Wnt5a-induced Rac1 activation could be inhibited by cirmtuzumab, but not by ibrutinib (FIGS. 15A-15B). The combination of cirmtuzumab with ibrutinib also inhibited Wnt5a-induced activation of Rac1 to levels observed in untreated cells (FIGS. 15A-15B). However, Wnt5a treatment could not induce activation of Rac1 in the leukemia cells of single-transgenic TCL1 mice, which develop a leukemia that lacks expression of ROR-1 (FIG. 7C).

Figure 15C:
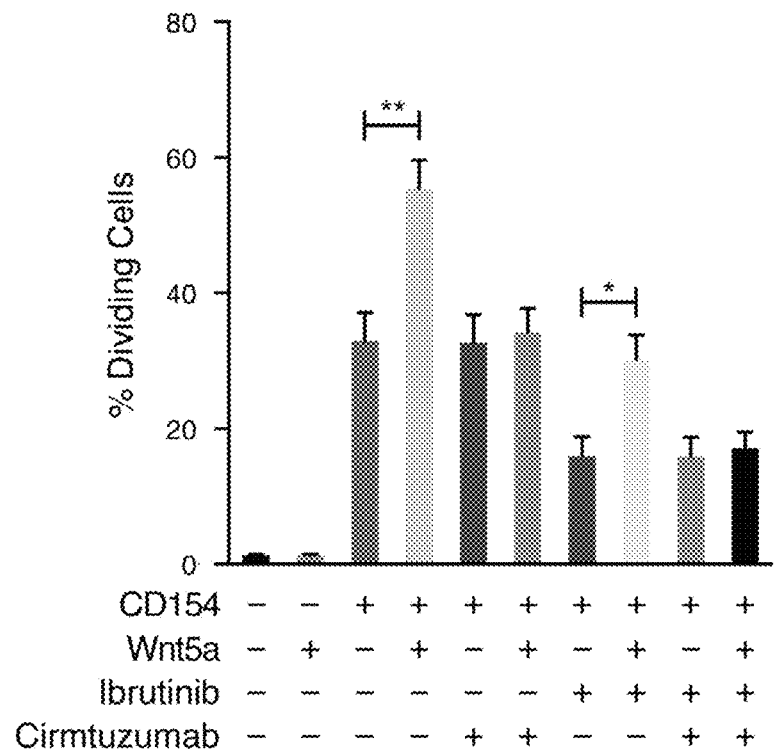
Figure 21:
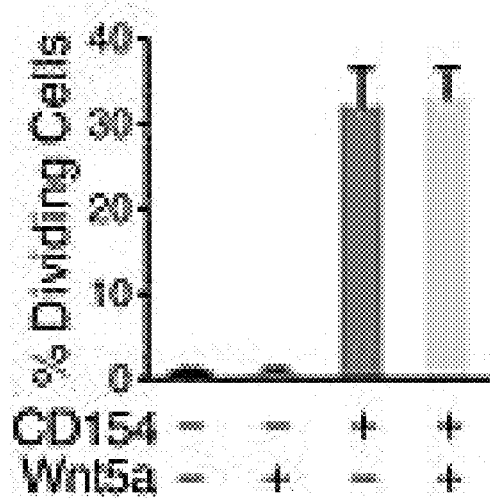
FIG. 21. CFSE assay for TCL1 leukemia cell proliferation induced by Wnt5a and/or CD154. Fluorescence of CFSE-labeled TCL1 leukemia cells (n=3) co-cultured for 5 days with wild-type HeLa or HeLacD154 cells without or with exogenous Wnt5a in the presence of IL-4/10. Data are shown as mean±SEM for each group; p-values were calculated using one-way ANOVA with Tukey's multiple comparisons test.
Figure 22A:
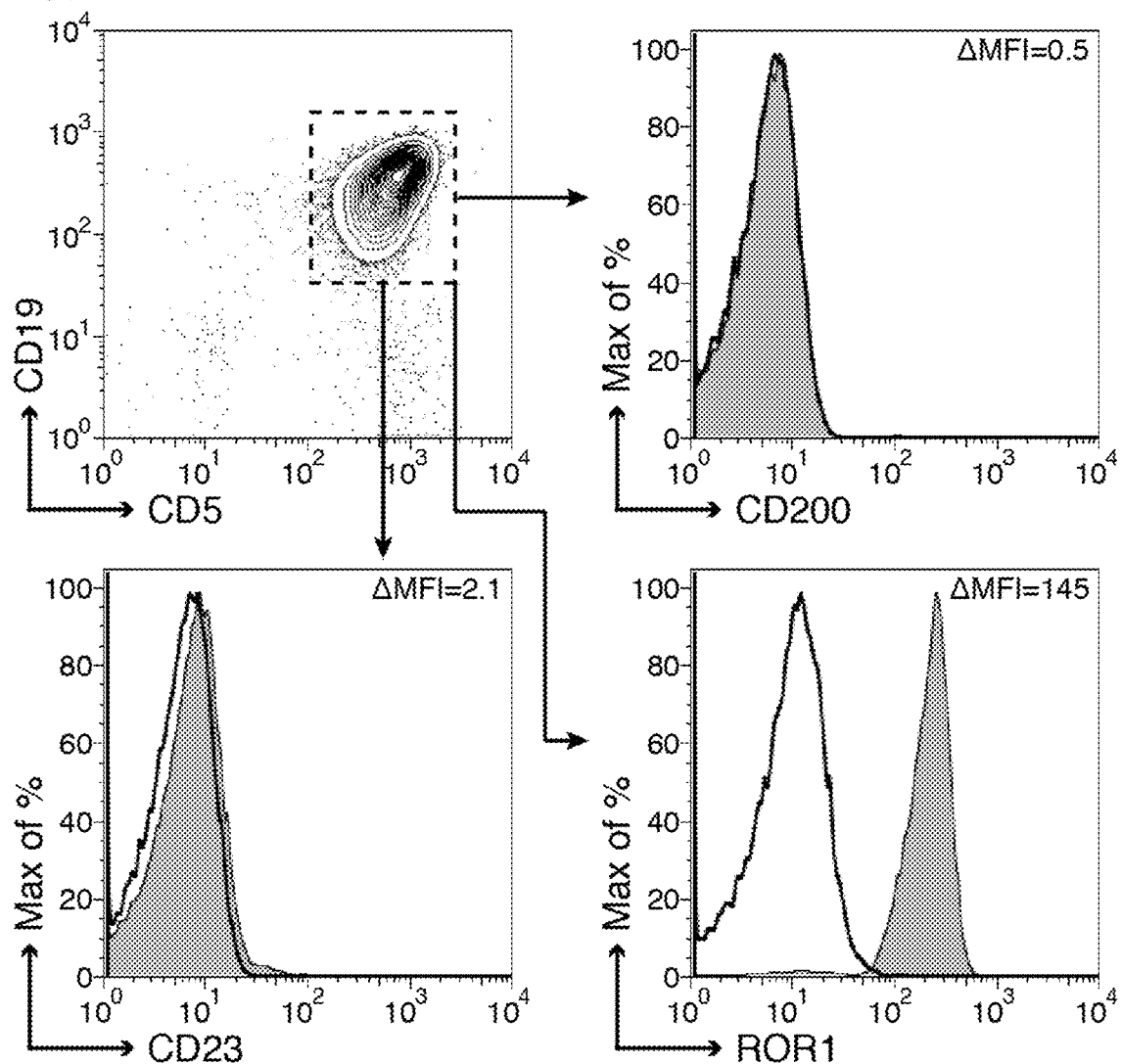
FIGS. 22A-22C. Antigen expression in primary MCL and Wnt5a level in MCL patient plasma.
Figure 22B:
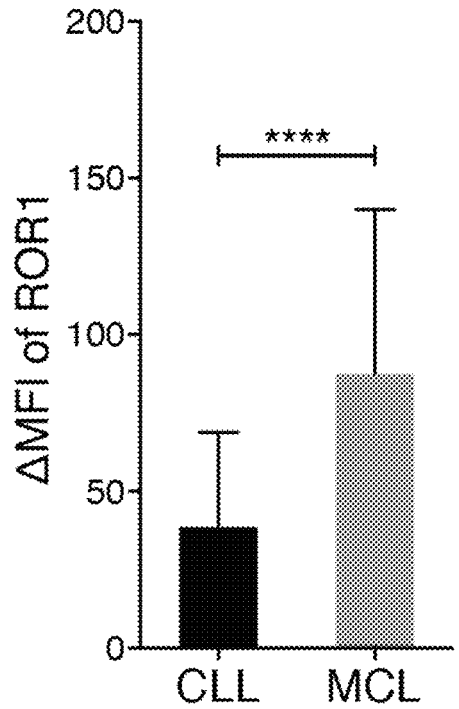
Figure 22C:
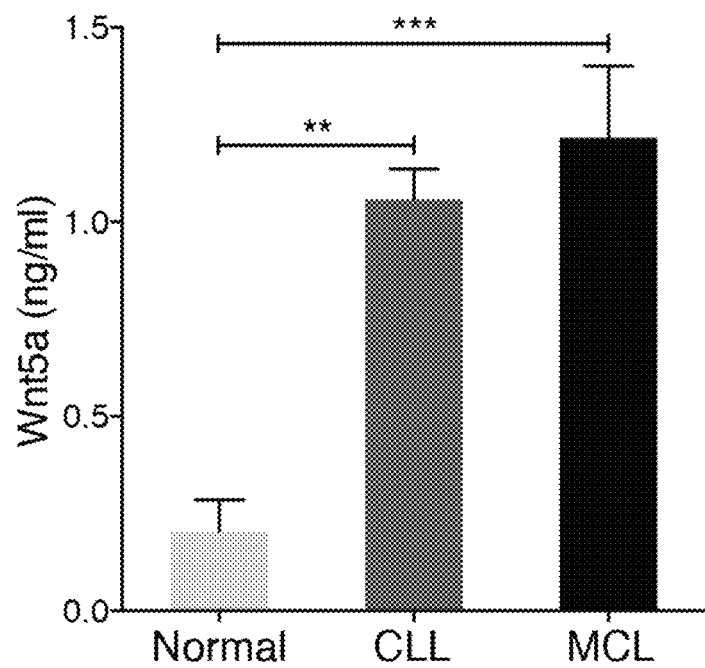

Again, Applicants induced proliferation of ROR-1×TCL1 leukemia cells by co-culturing the cells with HeLacD154 in the presence of recombinant IL-4/10. Exogenous Wnt5a significantly enhanced the percentage of numbers of cell divisions (FIG. 15C). As with human CLL cells, Wnt5a and/or IL-4/10 alone could not induce proliferation of ROR-1$^+$ leukemia cells of ROR-1×TCL1 transgenic mice (FIG. 15C), indicating a dependency on CD154 for this effect. In agreement with earlier studies, Wnt5a did not enhance the proliferation of ROR-1-negative TCL1-leukemia cells co-cultured with HeLa$_{CD154}$ cells and IL-4/10 (FIG. 21A), indicating a dependency on ROR-1 for this effect. Treatment with ibrutinib could not inhibit the capacity of Wnt5a to enhance the proliferation of CD154-induced ROR-1×TCL1 leukemia-cell proliferation. On the other hand, cirmtuzumab blocked the capacity of Wnt5a to enhance ROR-1×TCL1 leukemia cells proliferation in response to CD154 and IL-4/10 (FIG. 15C).

Figure 19A:
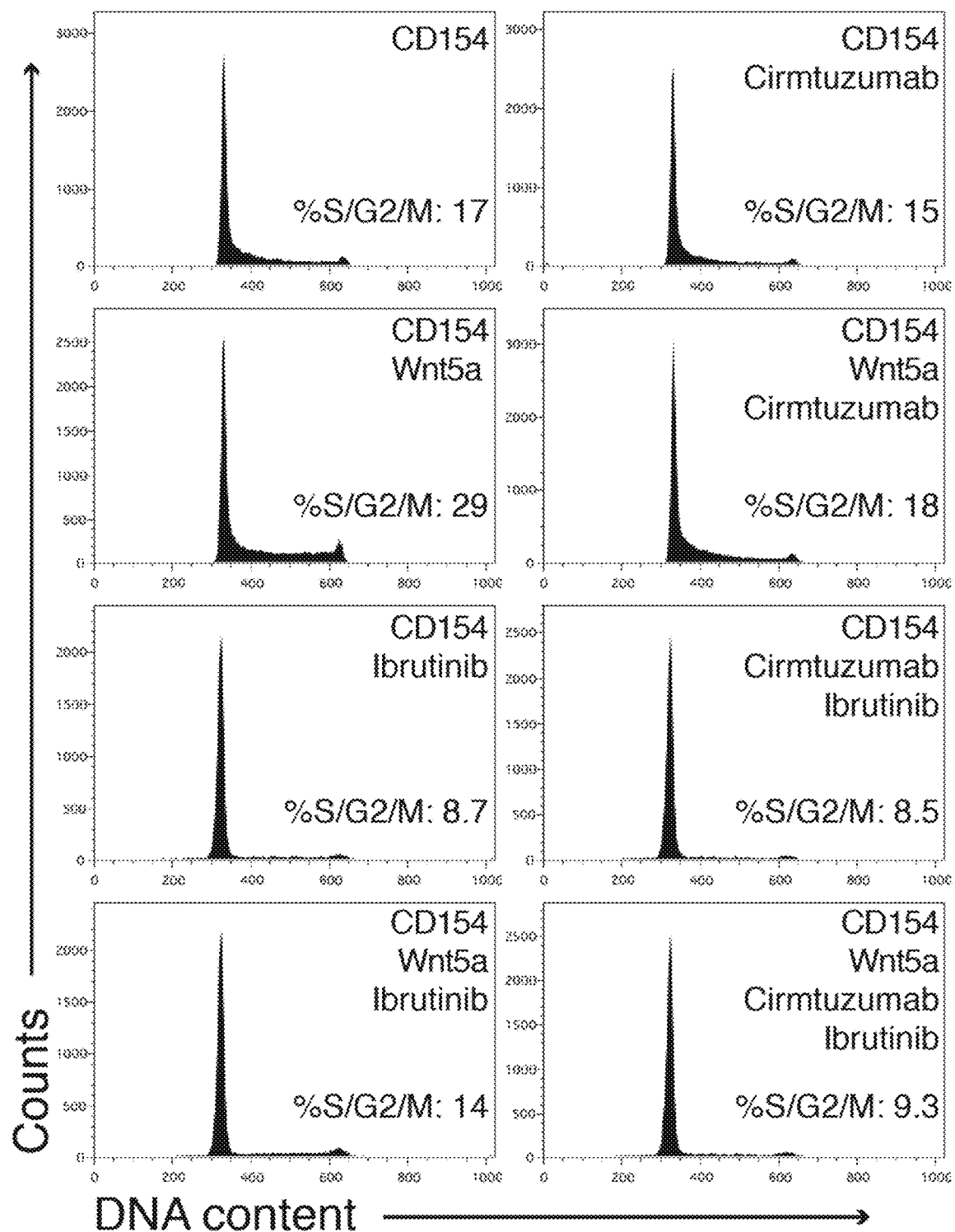
Figure 19B:
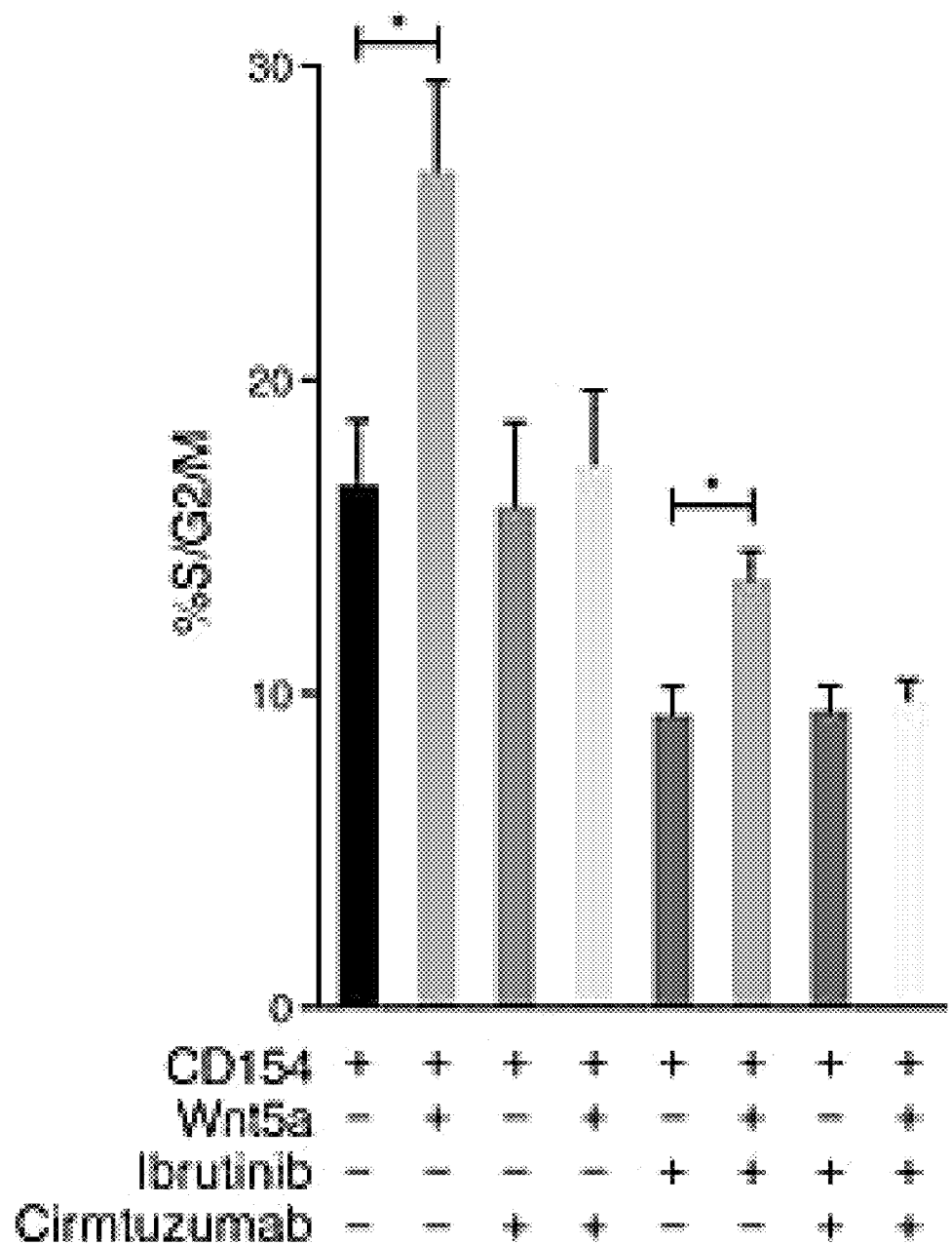

As noted for human CLL cells, cell-cycle analysis on permeabilized ROR-1×TCL1 leukemia cells using PI demonstrated that Wnt5a could increase the fraction of CD154-stimulated ROR-1+ leukemia cells in S/G2/M (FIGS. 19A-19B). Moreover, the capacity of Wnt5a to enhance the fraction of ROR-1+ leukemia cells in S/G2/M could be inhibited by treatment with cirmtuzumab, but not ibrutinib (FIGS. 19A-19B).

Figure 16A:
FIGS. 16A-16C. Additive inhibitory effect of treatment with cirmtuzumab and ibrutinib in immunodeficient mice engrafted histocompatible ROR-1$^+$ leukemia.
Figure 16B:
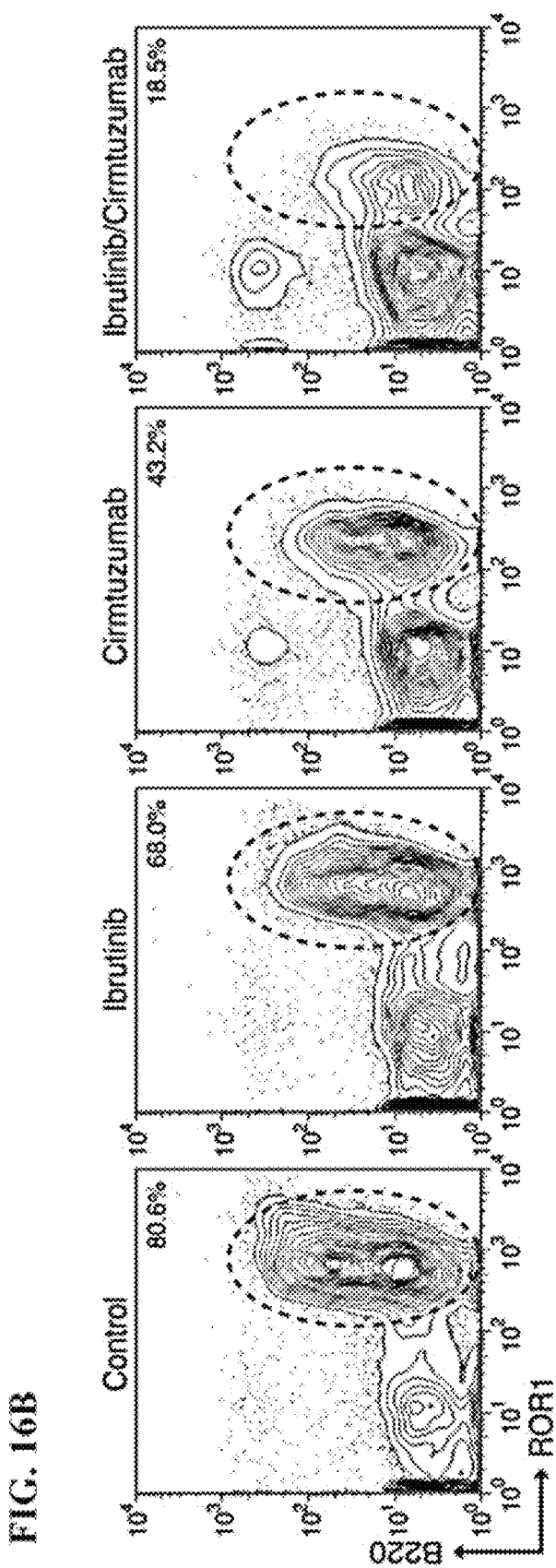
Figure 16C:
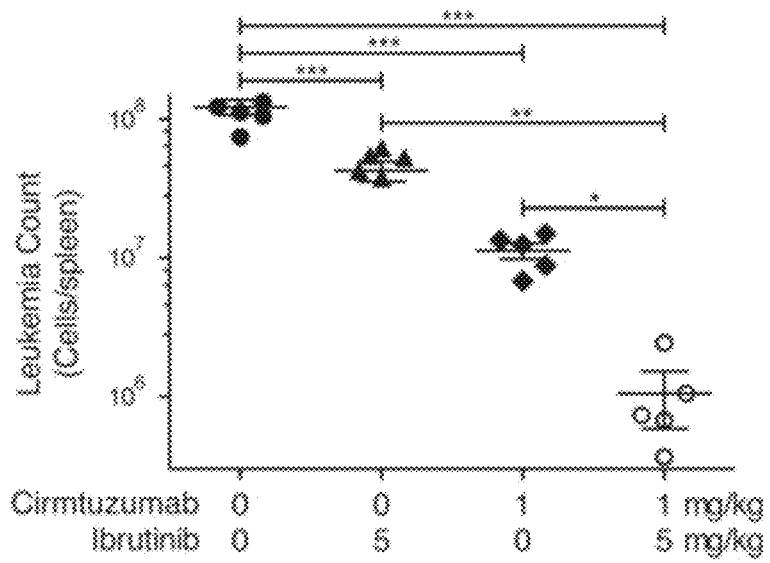
Figure 20A:
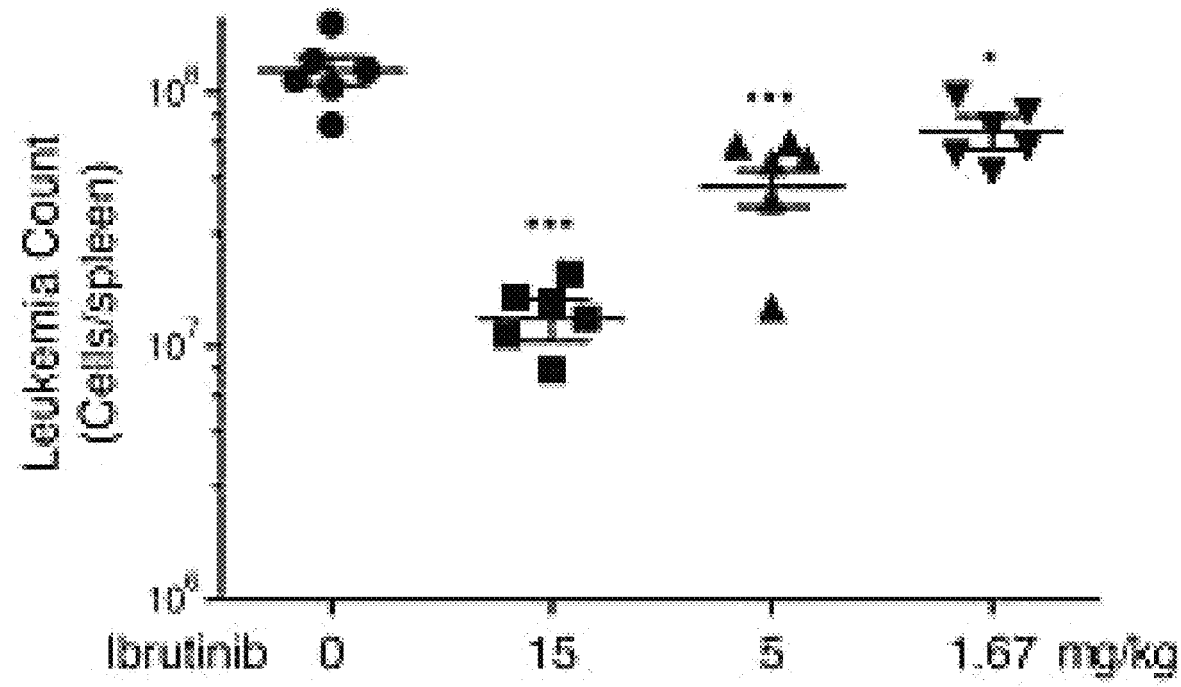
FIGS. 20A-20B. Dose-Dependent Inhibitory Effect of Cirmtuzumab or Ibrutinib on ROR-1×TCL1 Leukemia Engrafted Mice.
Figure 20B:
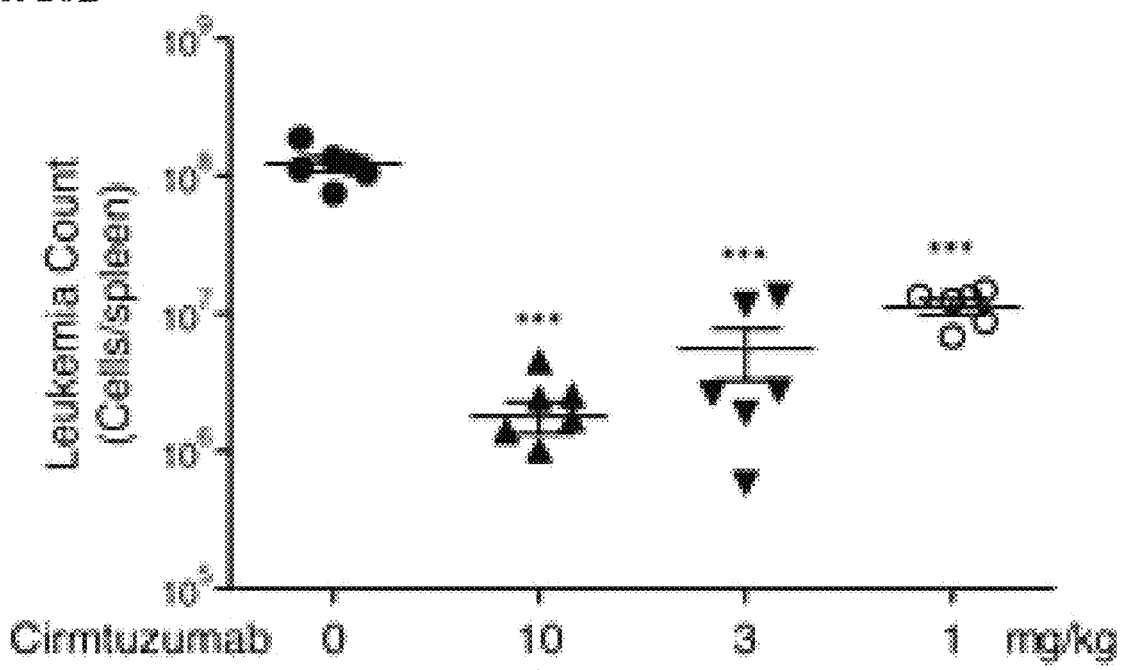

Treatment of immunodeficient mice engrafted with ROR-1×TCL1 leukemia with cirmtuzumab and/or ibrutinib. Applicants examined the capacity of cirmtuzumab and/or ibrutinib to inhibit ROR-1×TCL1 leukemia cell engraftment in $Rag2^{-/-}\gamma_c^{-/-}$ mice. Applicants engrafted each animal with $2 \times 10^4$ ROR-1×TCL1 leukemia cells and then administered daily ibrutinib at 15, 5, 1.67 mg/kg via gavage, or provided a single dose of cirmtuzumab at 1, 3, or 10 mg/kg via intravenous injection. After 25 days, the animals were sacrificed and the spleen of each animal was examined. Ibrutinib (FIG. 20A) or cirmtuzumab (FIG. 20B) reduced the numbers of splenic leukemia cells in a dose-dependent manner. Applicants selected the cirmtuzumab dose of 1 mg/kg and the daily dose of ibrutinib 5 mg/kg for combination studies. While the engrafted mice treated with cirmtuzumab or ibrutinib alone had significantly smaller spleens than the engrafted animals that did not receive any treatment, the mice treated with the combination of cirmtuzumab and ibrutinib had the greatest reductions in spleen size (FIG. 16A). Furthermore, the mean proportion and number of leukemia cells in the spleen were significantly lower in mice treated with cirmtuzumab or ibrutinib compared to engrafted mice that did not receive treatment (FIGS. 16B-16C). However, the engrafted animals that were treated with cirmtuzumab and ibrutinib had significantly lower proportions and numbers of leukemia cells per spleen than all other groups (FIGS. 16B-16C).

Figure 17A:
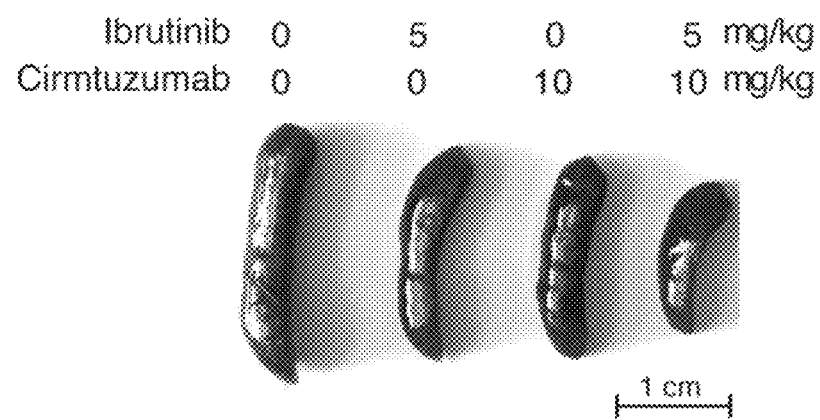
FIGS. 17A-17C. Additive inhibitory effect of treatment with cirmtuzumab and ibrutinib in immunocompetent mice engrafted histocompatible ROR-1$^+$ leukemia.
Figure 17B:
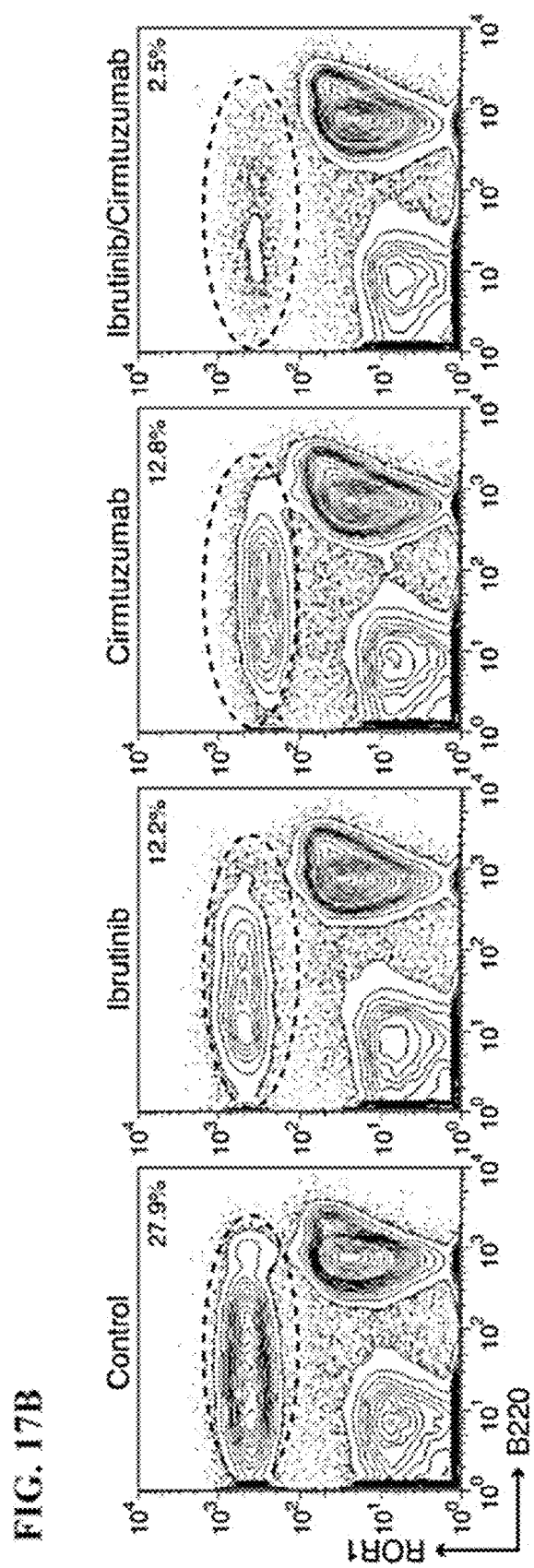
Figure 17C:
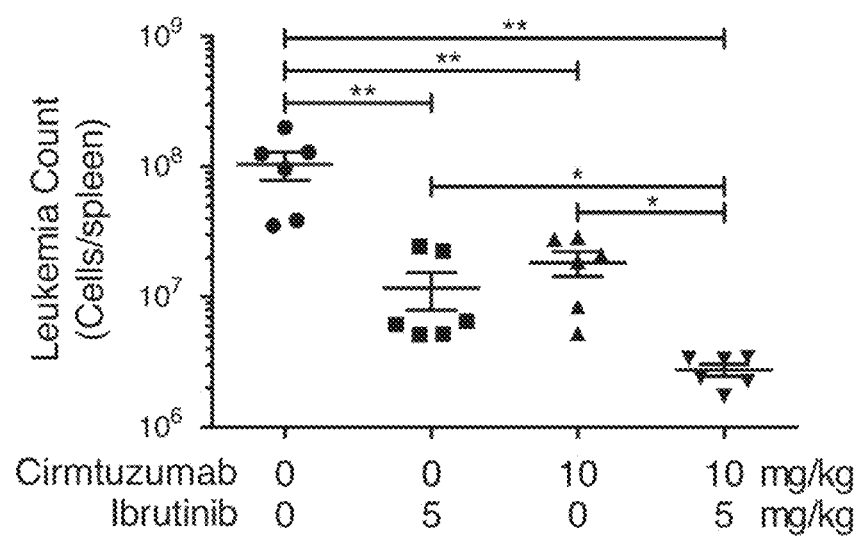

Treatment of immunocompetent mice engrafted with ROR-1×TCL1 leukemia with cirmtuzumab and/or ibrutinib. Applicants examined the capacity of cirmtuzumab and/or ibrutinib to inhibit engraftment of ROR-1×TCL1 leukemia cells (CD5B220$^{low}$ROR-1$^+$) in immunocompetent human-ROR-1 transgenic (ROR-1-Tg) mice. Applicants injected $2 \times 10^4$ ROR-1×TCL1 leukemia cells to ROR-1-Tg mice, and administered no treatment, daily doses of ibrutinib at 5 mg/kg via gavage, or weekly doses of cirmtuzumab at 10 mg/kg via intravenous injection. After 28 days, the animals were sacrificed and the spleen of each animal was examined. While the engrafted mice treated with cirmtuzumab or ibrutinib alone had significantly smaller spleens than the engrafted animals that did not receive any treatment, the mice treated with the combination of cirmtuzumab and ibrutinib had the greatest reductions in spleen size (FIG. 17A). Furthermore, the mean proportion and leukemia cell number in the spleen was significantly lower in mice treated with cirmtuzumab or ibrutinib than in mice that did not receive treatment (FIGS. 17B-17C). However, the engrafted animals that were treated with cirmtuzumab and ibrutinib had significantly lower proportions and numbers of leukemia cells per spleen than all other groups (FIGS. 17B-17C).

Discussion

In this study, Applicants examined the CLL cells of patients undergoing treatment with ibrutinib, which is highly effective at inhibiting BCR-signaling through its capacity to inhibit BTK. First, Applicants noted that the CLL cells of patients treated with ibrutinib had activated Rac1, which diminished over time in culture in serum-free media unless Applicants supplemented the media with exogenous Wnt5a. Moreover, Applicants found that Wnt5a could induce CLL to activate Rac1, as noted in a variety of cell types, including CLL cells. Subsequent studies showed that Wnt5a could induce Rac1 activation even in CLL cells that were treated with ibrutinib at supra-physiologic concentrations, which exceeded the levels required to achieve 100% occupancy and inhibition of BTK and BCR-signaling. The Wnt5a-signaling noted in this study was dependent upon ROR-1, as indicated by the capacity of cirmtuzumab to inhibit Wnt5a-induced activation of Rac1. Applicants conclude that ibrutinib cannot block ROR-1-dependent, Wnt5a-induced activation of Rac1, which serves as an intracellular signal transducer that can influence multiple signaling pathways.

Activated Rac1 might mitigate the effectiveness of anti-cancer therapy. Prior studies found that activated Rac1 can enhance resistance of CLL cells to cytotoxic drugs. One study found that activated T cells and fibroblasts could induce CLL cells to activate Rac1 and acquire resistance to the cytotoxic effects of fludarabine monophosphate; inhibition of activated Rac1 could restore the sensitivity of these CLL cells to this drug. In another study, Rac1 was found to interact with and enhance the function of Bcl2, which is over-expressed in CLL. Another study involving acute leukemia cells found that treatment with NSC-23766, an inhibitor of activated Rac1, could enhance the cytotoxicity of Bcl2 antagonists for leukemia cells. Finally loss of p53 in lymphoma cells has been associated with increased activation of Rac1, which could be inhibited by NSC-23766 or a dominant-negative form of Rac1, Rac1N17, leading to a dose-dependent increase in the rate of spontaneous or drug-induced apoptosis. Conceivably, the activated Rac1 observed in CLL cells of patients treated with ibrutinib provides an ancillary signal, which enhances the survival of leukemia cells of patients treated with ibrutinib.

Furthermore, Wnt5a-signaling also could promote leukemia-cell proliferation in patients treated with ibrutinib. The functional consequences of Wnt5-signaling in part are demonstrated by the ability of Wnt5a to enhance proliferation induced by CD154, which can induce CLL proliferation in vitro in the presence of exogenous IL4/10 or IL-21. Although ibrutinib partially could inhibit CD154-induced CLL cell proliferation, possibly due to its capacity to inhibit BCR and BCR-independent pathways, Applicants found that ibrutinib could not inhibit the capacity of Wnt5a to enhance CD154-induced CLL proliferation via ROR-1-dependent signaling, which could, however, be blocked by treatment with cirmtuzumab.

Wnt5a most likely is produced by cells in the CLL microenvironment, but also plasma of patients with CLL has high levels of Wnt5a. Wnt5a also might be produced by the CLL cells themselves, allowing for autocrine activation. Indeed, one study found that CLL cells that may express high levels of Wnt5a apparently have increased motility and chemotactic responses, presumably due to Wnt5a-autocrine signaling. Applicants also noted in an earlier study that Wnt5a could enhance the migration of CLL cells toward chemokine via activation of RhoA. However, because BTK plays a prominent role in CLL signaling via chemokine receptors such as CXCR4, Applicants focused attention on the capacity of Wnt5a to activate Rac1, which could enhance proliferation induced by CD154 via signaling pathways that are relatively independent of BTK.

Because the Wnt5a-ROR-1 signaling pathway appears intact in CLL cells treated with ibrutinib, Applicants examined for additive, if not synergistic, effects of treatment with ibrutinib and cirmtuzumab. For mice engrafted with histocompatible ROR-1+ leukemia, or human CLL xenografts, Applicants found that treatment with both cirmtuzumab and ibrutinib was significantly more effective than treatment with either agent alone in clearing leukemia cells in vivo. This study indicates that cirmtuzumab may enhance the activity of ibrutinib in the treatment of patients with CLL or other ROR-1+ B-cell malignancies.

Combination therapies are often more effective in treating patients with cancer. Investigations are ongoing to evaluate the activity of ibrutinib in combination with other drugs, such as venetoclax or anti-CD20 mAbs. Because cirmtuzumab and ibrutinib target independent signaling pathways, they have apparent synergistic effects in clearing leukemia cells from the mouse models. By targeting more than one signaling pathway leading to leukemia-cell growth/survival, combined therapy with cirmtuzumab and ibrutinib also could mitigate the risk of acquiring resistance to inhibitors of BTK, as sometimes occurs in patients who receive ibrutinib monotherapy.

Taken together, from the perspective of therapeutic efficacy and drug resistance, these preclinical observations provide a rationale for the combination therapy with cirmtuzumab with ibrutinib, or other inhibitors of BTK such as acalabrutinib, for patients with CLL or other B-cell malignancies that express ROR-1.

Figure 23A:
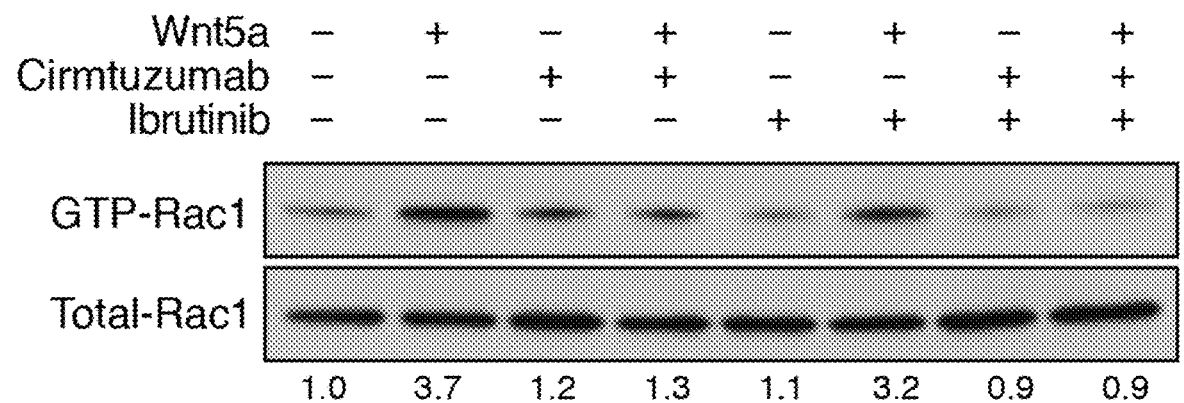
FIGS. 23A-23D. Analysis of Rac1 activation and cell-cycle in MCL cells.

Example 4. Combination of Anti-ROR-1 Antibody and Ibrutinib for Mantle Cell Lymphoma A recent study by Applicants' group demonstrated that CLL cells of patients treated with ibrutinib had activated Rac1. Moreover, Wnt5a could induce Rac1 activation and enhance proliferation of CLL cells treated with ibrutinib at concentrations that were effective in completely inhibiting BTK and BCR-signaling. Wnt5a-induced Rac1 activation could be blocked by cirmtuzumab (UC-961), an anti-ROR-1 mAb. Applicants found that treatment with cirmtuzumab and ibrutinib was significantly more effective than treatment with either agent alone in clearing leukemia cells in vivo. This study indicates that cirmtuzumab may enhance the activity of ibrutinib in the treatment of patients with CLL or other ROR-1+ B-cell malignancies. Thus, Applicants examined primary lymphoma cells of patients with MCL for Wnt5a-induced ROR-1-dependent activation of Rac1. MCL cells were cultured with ibrutinib, cirmtuzumab or both ibrutinib and cirmtuzumab for 2 h, and then stimulated with exogenous Wnt5a for 30 min. For comparison, cells from the same MCL sample were cultured without Wnt5a in parallel. As noted for CLL cells, Wnt5a induced activation of primary MCL cells in a ROR-1-dependent fashion. For example, Wnt5a induced Rac1 activation in the primary MCL cells (FIG. 23A). Cirmtuzumab, but not ibrutinib, could inhibit the capacity of Wnt5a to induce Rac1 activation in primary MCL cells, similar to what Applicants observed in primary CLL cells.

Figure 23B:
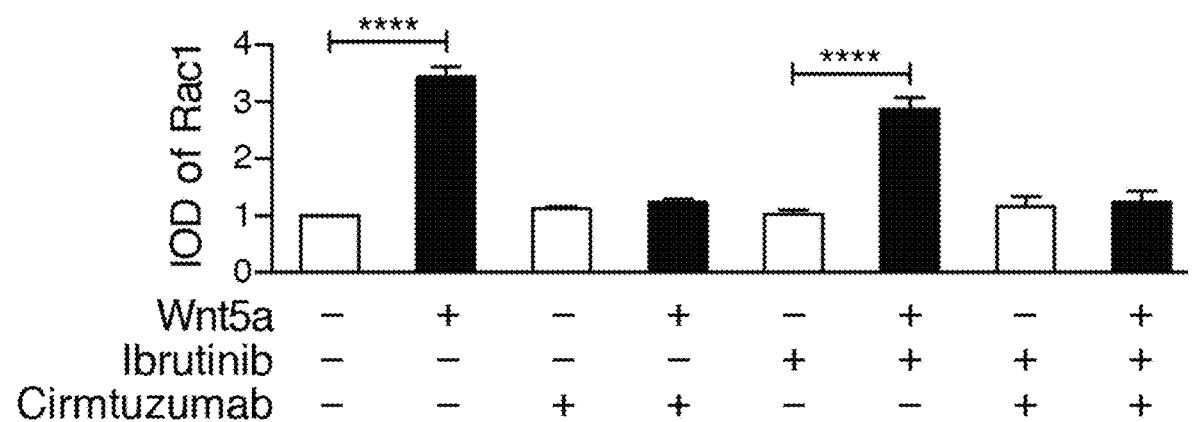
Figure 23C:
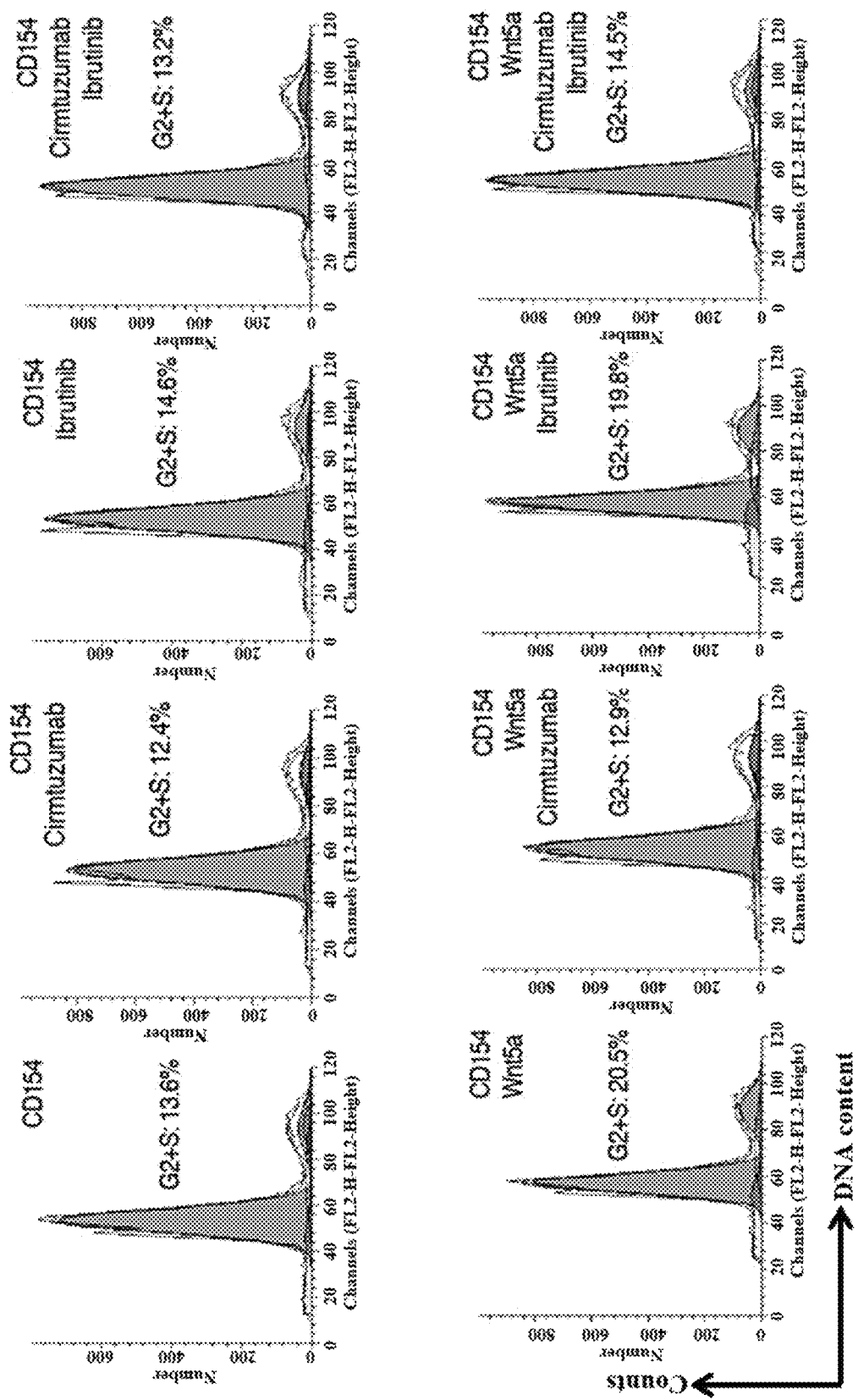
Figure 23D:
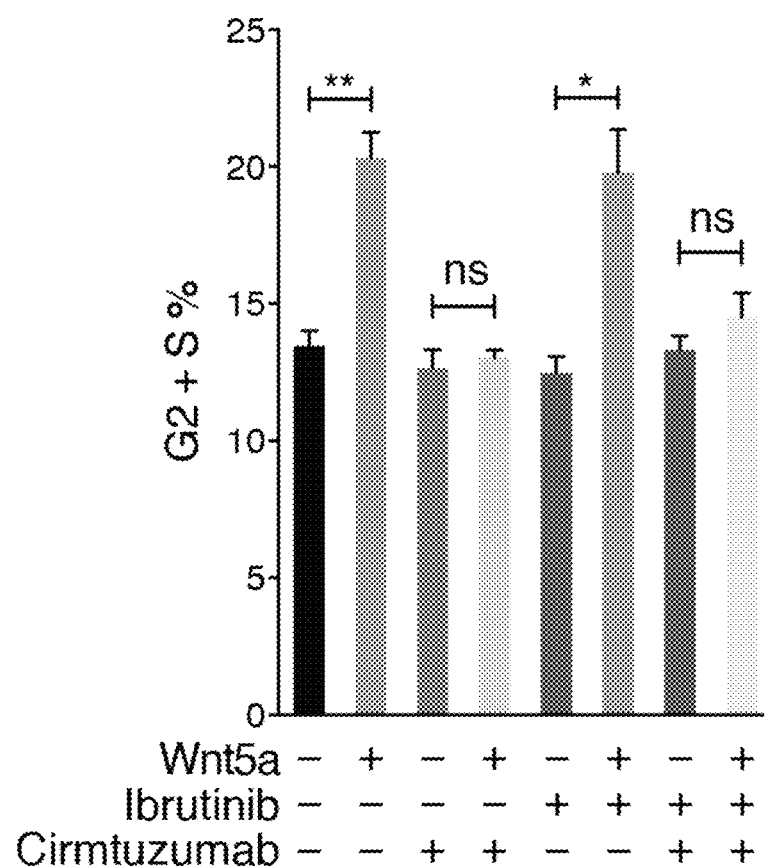

Activation of Rac1-GTPase can enhance proliferation, whereas loss of Rac1 results in impaired hematopoietic-cell growth. Propidium Iodide (PI) is the most commonly used dye for DNA content/cell cycle analysis. To evaluate the responsiveness of MCL cells to CD40 ligation and IL-4 exposure, Applicants induced proliferation of primary MCL cells by co-culturing the lymphoma cells with HeLa cells expressing CD154 (HeLaCD154) and recombinant IL-4 and IL-10. Addition of exogenous Wnt5a to co-cultures of MCL cells with HeLaCD154 cells and IL-4/10 significantly enhanced the proportion of MCL cells in S/G2 phase, as assessed using PI-based cell cycle studies, as noted for CLL cells. Applicants also performed cell-cycle analysis on permeabilized MCL cells using PI and found that Wnt5a stimulation significantly increased the fraction of CD154-stimulated MCL cells in S/G2 (FIG. 23B). The capacity of Wnt5a to enhance the proportion of primary MCL cells in S/G2 could be inhibited by treatment with cirmtuzumab, but not with ibrutinib, as noted previously for CLL cells.

These data demonstrate the functional importance of ROR-1 signaling in MCL and the ability of cirmtuzumab to inhibit ROR-1-mediated oncogenic activity in this lymphoma. The activity of cirmtuzumab in MCL is identical to what Applicants observed in CLL, for which Applicants found cirmtuzumab to have synergistic anti-tumor activity with ibrutinib in clearing leukemia cells in 3 different animal models.

Example 5. Candidate Drugs for the Treatment of Chronic Lymphocytic Leukemia and B-Cell Non-Hodgkin Lymphoma The novel BTK inhibitor ibrutinib and phosphatidyl-4-5-biphosphate 3-kinase-δ inhibitor idelalisib (CAL-101) are candidate drugs for the treatment of chronic lymphocytic leukemia and B-cell non-Hodgkin lymphoma, either alone or in combination with anti-CD20 antibodies Pretreatment with ibrutinib for 1 hour did not increase direct cell death of cell lines or chronic lymphocytic leukemia samples mediated by anti-CD20 antibodies. Pre-treatment with ibrutinib did not inhibit complement activation or complement-mediated lysis. In contrast, ibrutinib strongly inhibited all cell-mediated mechanisms induced by antiCD20 antibodies rituximab, ofatumumab or obinutuzumab, either in purified systems or whole blood assays. Activation of natural killer cells, and antibody-dependent cellular cytotoxicity by these cells, as well as phagocytosis by macrophages or neutrophils can be inhibited by ibrutinib with a half maximal effective concentration of 0.3-3 µM. Analysis of anti-CD20 mediated activation of natural killer cells isolated from patients on continued oral ibrutinib treatment suggests that repeated drug dosing inhibits these cells in vivo. It has been shown that the phosphatidyl-4-5-biphosphate 3-kinase-δ inhibitor idelalisib similarly inhibits the immune cell-mediated mechanisms induced by anti-CD20 antibodies, although the effects of this drug at 10 µM were weaker than those observed with ibrutinib at the same concentration. Without wishing to be bound by any theory, it is believed that the design of combined treatment schedules of antiCD20 antibodies with these kinase inhibitors should consider the multiple negative interactions between these two classes of drugs.

REFERENCES

Stevenson F K, Krysov S, Davies A J, Steele A J, Packham G. B-cell receptor signaling in chronic lymphocytic leukemia. Blood 2011 Oct. 20; 118: 4313-4320.

Burger J A, Tedeschi A, Barr P M, Robak T, Owen C, Ghia P, et al. Ibrutinib as Initial Therapy for Patients with Chronic Lymphocytic Leukemia. N Engl J Med 2015 Dec. 17; 373: 2425-2437.

Byrd J C, Furman R R, Coutre S E, Flinn I W, Burger J A, Blum K A, et al. Targeting BTK with ibrutinib in relapsed chronic lymphocytic leukemia. N Engl J Med 2013 Jul. 4; 369: 32-42.

Byrd J C, O'Brien S, James D F. Ibrutinib in relapsed chronic lymphocytic leukemia. N Engl J Med 2013 Sep. 26; 369: 1278-1279.

Komarova N L, Burger J A, Wodarz D. Evolution of ibrutinib resistance in chronic lymphocytic leukemia (CLL). Proc Natl Acad Sci USA 2014 Sep. 23; 111: 13906-13911.

Fukuda T, Chen L, Endo T, Tang L, Lu D, Castro J E, et al. Antisera induced by infusions of autologous Ad-CD154-leukemia B cells identify ROR-1 as an oncofetal antigen and receptor for Wnt5a. Proc Natl Acad Sci USA 2008 Feb. 26; 105: 3047-3052.

Widhopf G F, 2nd, Cui B, Ghia E M, Chen L, Messer K, Shen Z, et al. ROR-1 can interact with TCL1 and enhance leukemogenesis in Emu-TCL1 transgenic mice. Proc Natl Acad Sci USA 2014 Jan. 14; 111: 793-798.

Hofbauer S W, Krenn P W, Ganghammer S, Asslaber D, Pichler U, Oberascher K, et al. Tiam1/Rac1 signals contribute to the proliferation and chemoresistance, but not motility, of chronic lymphocytic leukemia cells. Blood 2014 Apr. 3; 123: 2181-2188.

Kaucka M, Plevova K, Pavlova S, Janovska P, Mishra A, Verner J, et al. The planar cell polarity pathway drives pathogenesis of chronic lymphocytic leukemia by the regulation of B-lymphocyte migration. Cancer Res 2013 Mar. 1; 73: 1491-1501.

Yu J, Chen L, Cui B, Widhopf G F, 2nd, Shen Z, Wu R, et al. Wnt5a induces ROR-1/ROR2 heterooligomerization to enhance leukemia chemotaxis and proliferation. J Clin Invest 2015 Dec. 21.

Choi M Y, Widhopf GF, 2nd, Wu C C, Cui B, Lao F, Sadarangani A, et al. Pre-clinical Specificity and Safety of UC-961, a First-In-Class Monoclonal Antibody Targeting ROR-1. Clin Lymphoma Myeloma Leuk 2015 June; 15 Suppl: S167-169.

Nishita M, Itsukushima S, Nomachi A, Endo M, Wang Z, Inaba D, et al. Ror2/Frizzled complex mediates Wnt5a-induced AP-1 activation by regulating Dishevelled polymerization. Mol Cell Biol 2010 July; 30: 3610-3619.

Naskar D, Maiti G, Chakraborty A, Roy A, Chattopadhyay D, Sen M. Wnt5a-Rac1-NF-kappaB homeostatic circuitry sustains innate immune functions in macrophages. J Immunol 2014 May 1; 192: 4386-4397.

Zhu Y, Shen T, Liu J, Zheng J, Zhang Y, Xu R, et al. Rab35 is required for Wnt5a/Dvl2-induced Rac1 activation and cell migration in MCF-7 breast cancer cells. Cell Signal 2013 May; 25: 1075-1085.

Ren L, Campbell A, Fang H, Gautam S, Elavazhagan S, Fatehchand K, et al. Analysis of the Effects of the Bruton's tyrosine kinase (BTK) Inhibitor Ibrutinib on Monocyte Fcgamma Receptor (FcgammaR) Function. J Biol Chem 2016 Feb. 5; 291: 3043-3052.

Honigberg L A, Smith A M, Sirisawad M, Verner E, Loury D, Chang B, et al. The Bruton tyrosine kinase inhibitor PCI-32765 blocks B-cell activation and is efficacious in models of autoimmune disease and B-cell malignancy. Proc Natl Acad Sci USA 2010 Jul. 20; 107: 13075-13080.

Rushworth S A, Murray M Y, Zaitseva L, Bowles K M, MacEwan D J. Identification of Bruton's tyrosine kinase as a therapeutic target in acute myeloid leukemia. Blood 2014 Feb. 20; 123: 1229-1238.

Di Paolo J A, Huang T, Balazs M, Barbosa J, Barck K H, Bravo B J, et al. Specific BTK inhibition suppresses B cell- and myeloid cell-mediated arthritis. Nat Chem Biol 2011 January; 7: 41-50.

de Jong J, Sukbuntherng J, Skee D, Murphy J, O'Brien S, Byrd J C, et al. The effect of food on the pharmacokinetics of oral ibrutinib in healthy participants and patients with chronic lymphocytic leukemia. Cancer Chemother Pharmacol 2015 May; 75: 907-916.

Advani R H, Buggy J J, Sharman J P, Smith S M, Boyd T E, Grant B, et al. Bruton tyrosine kinase inhibitor ibrutinib (PCI-32765) has significant activity in patients with relapsed/refractory B-cell malignancies. J Clin Oncol 2013 Jan. 1; 31: 88-94.

Etienne-Manneville S, Hall A. Rho GTPases in cell biology. Nature 2002 Dec. 12; 420: 629-635.

Gu Y, Filippi M D, Cancelas J A, Siefring J E, Williams E P, Jasti A C, et al. Hematopoietic cell regulation by Rac1 and Rac2 guanosine triphosphatases. Science 2003 Oct. 17; 302: 445-449.

Fecteau J F, Corral L G, Ghia E M, Gaidarova S, Futalan D, Bharati I S, et al. Lenalidomide inhibits the proliferation of CLL cells via a cereblon/p21(WAF1/Cip1)-dependent mechanism independent of functional p53. Blood 2014 Sep. 4; 124: 1637-1644.

Zhang S, Wu C C, Fecteau J F, Cui B, Chen L, Zhang L, et al. Targeting chronic lymphocytic leukemia cells with a humanized monoclonal antibody specific for CD44. Proc Natl Acad Sci USA 2013 Apr. 9; 110: 6127-6132.

Herishanu Y, Perez-Galan P, Liu D, Biancotto A, Pittaluga S, Vire B, et al. The lymph node microenvironment promotes B-cell receptor signaling, NF-kappaB activation, and tumor proliferation in chronic lymphocytic leukemia. Blood 2011 Jan. 13; 117: 563-574.

Burger J A. Nurture versus nature: the microenvironment in chronic lymphocytic leukemia. Hematology Am Soc Hematol Educ Program 2011; 2011: 96-103.

Chiorazzi N, Rai K R, Ferrarini M. Chronic lymphocytic leukemia. N Engl J Med 2005 Feb. 24; 352: 804-815.

Rossi D, Spina V, Bomben R, Rasi S, Dal-Bo M, Bruscaggin A, et al. Association between molecular lesions and specific B-cell receptor subsets in chronic lymphocytic leukemia. Blood 2013 Jun. 13; 121: 4902-4905.

Ghia P, Chiorazzi N, Stamatopoulos K. Microenvironmental influences in chronic lymphocytic leukaemia: the role of antigen stimulation. J Intern Med 2008 December; 264: 549-562.

Herishanu Y, Katz B Z, Lipsky A, Wiestner A. Biology of chronic lymphocytic leukemia in different microenvironments: clinical and therapeutic implications. Hematol Oncol Clin North Am 2013 April; 27: 173-206.

Woyach J A, Bojnik E, Ruppert A S, Stefanovski M R, Goettl V M, Smucker K A, et al. Bruton's tyrosine kinase (BTK) function is important to the development and expansion of chronic lymphocytic leukemia (CLL). Blood 2014 Feb. 20; 123: 1207-1213.

Herman S E, Mustafa R Z, Gyamfi J A, Pittaluga S, Chang S, Chang B, et al. Ibrutinib inhibits BCR and NF-kappaB signaling and reduces tumor proliferation in tissue-resident cells of patients with CLL. Blood 2014 May 22; 123: 3286-3295.

Cheng S, Ma J, Guo A, Lu P, Leonard J P, Coleman M, et al. BTK inhibition targets in vivo CLL proliferation through its effects on B-cell receptor signaling activity. Leukemia 2014 March; 28: 649-657.

Mathews Griner L A, Guha R, Shinn P, Young R M, Keller J M, Liu D, et al. High-throughput combinatorial screening identifies drugs that cooperate with ibrutinib to kill activated B-cell-like diffuse large B-cell lymphoma cells. Proc Natl Acad Sci USA 2014 Feb. 11; 111: 2349-2354.

Guo A, Lu P, Galanina N, Nabhan C, Smith S M, Coleman M, et al. Heightened BTK-dependent cell proliferation in unmutated chronic lymphocytic leukemia confers increased sensitivity to ibrutinib. *Oncotarget* 2016 Jan. 26; 7: 4598-4610.

Woodcock J, Griffin J P, Behrman R E. Development of novel combination therapies. N Engl J Med 2011 Mar. 17; 364: 985-987.

Cervantes-Gomez F, Lamothe B, Woyach J A, Wierda W G, Keating M J, Balakrishnan K, et al. Pharmacological and Protein Profiling Suggests Venetoclax (ABT-199) as Optimal Partner with Ibrutinib in Chronic Lymphocytic Leukemia. Clin Cancer Res 2015 Aug. 15; 21: 3705-3715.

Zhao X, Bodo J, Sun D, Durkin L, Lin J, Smith M R, et al. Combination of ibrutinib with ABT-199: synergistic effects on proliferation inhibition and apoptosis in mantle cell lymphoma cells through perturbation of BTK, AKT and BCL2 pathways. Br J Haematol 2015 March; 168: 765-768.

de Rooij M F, Kuil A, Kater A P, Kersten M J, Pals S T, Spaargaren M. Ibrutinib and idelalisib synergistically target BCR-controlled adhesion in MCL and CLL: a rationale for combination therapy. Blood 2015 Apr. 2; 125: 2306-2309.

Da Roit F, Engelberts P J, Taylor R P, Breij E C, Gritti G, Rambaldi A, et al. Ibrutinib interferes with the cell-mediated anti-tumor activities of therapeutic CD20 antibodies: implications for combination therapy. Haematologica 2015 January; 100: 77-86.

Skarzynski M, Niemann C U, Lee Y S, Martyr S, Maric I, Salem D, et al. Interactions between Ibrutinib and Anti-CD20 Antibodies: Competing Effects on the Outcome of Combination Therapy. Clin Cancer Res 2016 Jan. 1; 22: 86-95.

Woyach J A, Furman R R, Liu T M, Ozer H G, Zapatka M, Ruppert A S, et al. Resistance mechanisms for the Bruton's tyrosine kinase inhibitor ibrutinib. N Engl J Med 2014 Jun. 12; 370: 2286-2294.

Yuan Y, Shen H, Franklin D S, Scadden D T, Cheng T. In vivo self-renewing divisions of haematopoietic stem cells are increased in the absence of the early G1-phase inhibitor, p18INK4C. Nat Cell Biol 2004 May; 6: 436-442.

Shen H, Yu H, Liang P H, Cheng H, XuFeng R, Yuan Y, et al. An acute negative bystander effect of gamma-irradiated recipients on transplanted hematopoietic stem cells. Blood 2012 Apr. 12; 119: 3629-3637.

Ghia P, Chiorazzi N, Stamatopoulos K. Microenvironmental influences in chronic lymphocytic leukaemia: the role of antigen stimulation. J Intern Med 2008 December; 264: 549-562.

Herishanu Y, Katz B Z, Lipsky A, Wiestner A. Biology of chronic lymphocytic leukemia in different microenvironments: clinical and therapeutic implications. Hematol Oncol Clin North Am 2013 April; 27: 173-206.

Burger J A. Nurture versus nature: the microenvironment in chronic lymphocytic leukemia. Hematology Am Soc Hematol Educ Program 2011; 2011: 96-103.

Stevenson F K, Krysov S, Davies A J, Steele A J, Packham G. B-cell receptor signaling in chronic lymphocytic leukemia. Blood 2011 Oct. 20; 118: 4313-4320.

Burger J A, Tedeschi A, Barr P M, Robak T, Owen C, Ghia P, et al. Ibrutinib as Initial Therapy for Patients with Chronic Lymphocytic Leukemia. N Engl J Med 2015 Dec. 17; 373: 2425-2437.

Byrd J C, Furman R R, Coutre S E, Flinn I W, Burger J A, Blum K A, et al. Targeting BTK with ibrutinib in relapsed chronic lymphocytic leukemia. N Engl J Med 2013 Jul. 4; 369: 32-42.

Byrd J C, O'Brien S, James D F. Ibrutinib in relapsed chronic lymphocytic leukemia. N Engl J Med 2013 Sep. 26; 369: 1278-1279.

Komarova N L, Burger J A, Wodarz D. Evolution of ibrutinib resistance in chronic lymphocytic leukemia (CLL). Proc Natl Acad Sci USA 2014 Sep. 23; 111: 13906-13911.

Fukuda T, Chen L, Endo T, Tang L, Lu D, Castro J E, et al. Antisera induced by infusions of autologous Ad-CD154-leukemia B cells identify ROR-1 as an oncofetal antigen and receptor for Wnt5a. Proc Natl Acad Sci USA 2008 Feb. 26; 105: 3047-3052.

Widhopf G F, 2nd, Cui B, Ghia E M, Chen L, Messer K, Shen Z, et al. ROR-1 can interact with TCL1 and enhance leukemogenesis in Emu-TCL1 transgenic mice. Proc Natl Acad Sci USA 2014 Jan. 14; 111: 793-798.

Hofbauer S W, Krenn P W, Ganghammer S, Asslaber D, Pichler U, Oberascher K, et al. Tiam1/Rac1 signals contribute to the proliferation and chemoresistance, but not motility, of chronic lymphocytic leukemia cells. Blood 2014 Apr. 3; 123: 2181-2188.

Kaucka M, Plevova K, Pavlova S, Janovska P, Mishra A, Verner J, et al. The planar cell polarity pathway drives pathogenesis of chronic lymphocytic leukemia by the regulation of B-lymphocyte migration. Cancer Res 2013 Mar. 1; 73: 1491-1501.

Yu J, Chen L, Cui B, Widhopf G F, 2nd, Shen Z, Wu R, et al. Wnt5a induces ROR-1/ROR2 heterooligomerization to enhance leukemia chemotaxis and proliferation. J Clin Invest 2015 Dec. 21.

Choi M Y, Widhopf G F, 2nd, Wu C C, Cui B, Lao F, Sadarangani A, et al. Pre-clinical Specificity and Safety of UC-961, a First-In-Class Monoclonal Antibody Targeting ROR-1. Clin Lymphoma Myeloma Leuk 2015 June; 15 Suppl: S167-169.

Honigberg L A, Smith A M, Sirisawad M, Verner E, Loury D, Chang B, et al. The Bruton tyrosine kinase inhibitor PCI-32765 blocks B-cell activation and is efficacious in models of autoimmune disease and B-cell malignancy. Proc Natl Acad Sci USA 2010 Jul. 20; 107: 13075-13080.

Rushworth S A, Murray M Y, Zaitseva L, Bowles K M, MacEwan D J. Identification of Bruton's tyrosine kinase as a therapeutic target in acute myeloid leukemia. Blood 2014 Feb. 20; 123: 1229-1238.

Ren L, Campbell A, Fang H, Gautam S, Elavazhagan S, Fatehchand K, et al. Analysis of the Effects of the Bruton's tyrosine kinase (BTK) Inhibitor Ibrutinib on Monocyte Fcgamma Receptor (FcgammaR) Function. J Biol Chem 2016 Feb. 5; 291: 3043-3052.

Di Paolo J A, Huang T, Balazs M, Barbosa J, Barck K H, Bravo B J, et al. Specific BTK inhibition suppresses B cell- and myeloid cell-mediated arthritis. Nat Chem Biol 2011 January; 7: 41-50.

de Jong J, Sukbuntherng J, Skee D, Murphy J, O'Brien S, Byrd J C, et al. The effect of food on the pharmacokinetics of oral ibrutinib in healthy participants and patients with chronic lymphocytic leukemia. Cancer Chemother Pharmacol 2015 May; 75: 907-916.

Advani R H, Buggy J J, Sharman J P, Smith S M, Boyd T E, Grant B, et al. Bruton tyrosine kinase inhibitor ibrutinib (PCI-32765) has significant activity in patients with relapsed/refractory B-cell malignancies. J Clin Oncol 2013 Jan. 1; 31: 88-94.

Etienne-Manneville S, Hall A. Rho GTPases in cell biology. Nature 2002 Dec. 12; 420: 629-635.

Gu Y, Filippi M D, Cancelas J A, Siefring J E, Williams E P, Jasti A C, et al. Hematopoietic cell regulation by Rac1 and Rac2 guanosine triphosphatases. *Science* 2003 Oct. 17; 302: 445-449.

Fecteau J F, Corral L G, Ghia E M, Gaidarova S, Futalan D, Bharati I S, et al. Lenalidomide inhibits the proliferation of CLL cells via a cereblon/p21(WAF1/Cip1)-dependent mechanism independent of functional p53. *Blood* 2014 Sep. 4; 124: 1637-1644.

Zhang S, Wu C C, Fecteau J F, Cui B, Chen L, Zhang L, et al. Targeting chronic lymphocytic leukemia cells with a humanized monoclonal antibody specific for CD44. *Proc Natl Acad Sci USA* 2013 Apr. 9; 110: 6127-6132.

Herman S E, Mustafa R Z, Gyamfi J A, Pittaluga S, Chang S, Chang B, et al. Ibrutinib inhibits BCR and NF-kappaB signaling and reduces tumor proliferation in tissue-resident cells of patients with CLL. *Blood* 2014 May 22; 123: 3286-3295.

Cheng S, Ma J, Guo A, Lu P, Leonard J P, Coleman M, et al. BTK inhibition targets in vivo CLL proliferation through its effects on B-cell receptor signaling activity. *Leukemia* 2014 March; 28: 649-657.

Nishita M, Itsukushima S, Nomachi A, Endo M, Wang Z, Inaba D, et al. Ror2/Frizzled complex mediates Wnt5a-induced AP-1 activation by regulating Dishevelled polymerization. *Mol Cell Biol* 2010 July; 30: 3610-3619.

Naskar D, Maiti G, Chakraborty A, Roy A, Chattopadhyay D, Sen M. Wnt5a-Rac1-NF-kappaB homeostatic circuitry sustains innate immune functions in macrophages. *J Immunol* 2014 May 1; 192: 4386-4397.

Zhu Y, Shen T, Liu J, Zheng J, Zhang Y, Xu R, et al. Rab35 is required for Wnt5a/Dvl2-induced Rac1 activation and cell migration in MCF-7 breast cancer cells. *Cell Signal* 2013 May; 25: 1075-1085.

Velaithan R, Kang J, Hirpara J L, Loh T, Goh B C, Le Bras M, et al. The small GTPase Rac1 is a novel binding partner of Bcl-2 and stabilizes its antiapoptotic activity. *Blood* 2011 Jun. 9; 117: 6214-6226.

Roberts A W, Seymour J F, Brown J R, Wierda W G, Kipps T J, Khaw S L, et al. Substantial susceptibility of chronic lymphocytic leukemia to BCL2 inhibition: results of a phase I study of navitoclax in patients with relapsed or refractory disease. *J Clin Oncol* 2012 Feb. 10; 30: 488-496.

Mizukawa B, Wei J, Shrestha M, Wunderlich M, Chou F S, Griesinger A, et al. Inhibition of Rac GTPase signaling and downstream prosurvival Bcl-2 proteins as combination targeted therapy in MLL-AF9 leukemia. *Blood* 2011 Nov. 10; 118: 5235-5245.

Bosco E E, Ni W, Wang L, Guo F, Johnson J F, Zheng Y. Rac1 targeting suppresses p53 deficiency-mediated lymphomagenesis. Blood 2010 Apr. 22; 115: 3320-3328.

Pascutti M F, Jak M, Tromp J M, Derks I A, Remmerswaal E B, Thijssen R, et al. IL-21 and CD40L signals from autologous T cells can induce antigen-independent proliferation of CLL cells. *Blood* 2013 Oct. 24; 122: 3010-3019.

Guo A, Lu P, Galanina N, Nabhan C, Smith S M, Coleman M, et al. Heightened BTK-dependent cell proliferation in unmutated chronic lymphocytic leukemia confers increased sensitivity to ibrutinib. Oncotarget 2016 Jan. 26; 7: 4598-4610.

Janovska P, Poppova L, Plevova K, Plesingerova H, Behal M, Kaucka M, et al. Autocrine Signaling by Wnt-5a Deregulates Chemotaxis of Leukemic Cells and Predicts Clinical Outcome in Chronic Lymphocytic Leukemia. *Clin Cancer Res* 2016 Jan. 15; 22: 459-469.

O'Hayre M, Salanga C L, Kipps T J, Messmer D, Dorrestein P C, Handel T M. Elucidating the CXCL12/CXCR4 signaling network in chronic lymphocytic leukemia through phosphoproteomics analysis. *PLoS One* 2010; 5: e11716.

Woodcock J, Griffin J P, Behrman R E. Development of novel combination therapies. N Engl J Med 2011 Mar. 17; 364: 985-987.

Da Roit F, Engelberts P J, Taylor R P, Breij E C, Gritti G, Rambaldi A, et al. Ibrutinib interferes with the cell-mediated anti-tumor activities of therapeutic CD20 antibodies: implications for combination therapy. *Haematologica* 2015 January; 100: 77-86.

Skarzynski M, Niemann C U, Lee Y S, Martyr S, Maric I, Salem D, et al. Interactions between Ibrutinib and Anti-CD20 Antibodies: Competing Effects on the Outcome of Combination Therapy. *Clin Cancer Res* 2016 Jan. 1; 22: 86-95.

Woyach J A, Furman R R, Liu T M, Ozer H G, Zapatka M, Ruppert A S, et al. Resistance mechanisms for the Bruton's tyrosine kinase inhibitor ibrutinib. *N Engl J Med* 2014 Jun. 12; 370: 2286-2294.

Wu J, Zhang M, Liu D. Acalabrutinib (ACP-196): a selective second-generation BTK inhibitor. *J Hematol Oncol* 2016; 9: 21.

Byrd J C, Harrington B, O'Brien S, Jones J A, Schuh A, Devereux S, et al. Acalabrutinib (ACP-196) in Relapsed Chronic Lymphocytic Leukemia. *N Engl J Med* 2016 Jan. 28; 374: 323-332.

Zhang B, Chernoff J, Zheng Y. Interaction of Rac1 with GTPase-activating proteins and putative effectors. A comparison with Cdc42 and RhoA. *J Biol Chem* 1998 Apr. 10; 273: 8776-8782.

Yuan Y, Shen H, Franklin D S, Scadden D T, Cheng T. In vivo self-renewing divisions of haematopoietic stem cells are increased in the absence of the early G1-phase inhibitor, p18INK4C. *Nat Cell Biol* 2004 May; 6: 436-442.

Shen H, Yu H, Liang P H, Cheng H, XuFeng R, Yuan Y, et al. An acute negative bystander effect of gamma-irradiated recipients on transplanted hematopoietic stem cells. *Blood* 2012 Apr. 12; 119: 3629-3637.

Honigberg L A, Smith A M, Sirisawad M, Verner E, Loury D, Chang B, et al. The Bruton tyrosine kinase inhibitor PCI-32765 blocks B-cell activation and is efficacious in models of autoimmune disease and B-cell malignancy. *Proc Natl Acad Sci USA* 2010 Jul. 20; 107: 13075-13080.

Di Paolo J A, Huang T, Balazs M, Barbosa J, Barck K H, Bravo B J, et al. Specific BTK inhibition suppresses B cell- and myeloid cell-mediated arthritis. *Nat Chem Biol* 2011 January; 7: 41-50.

Zhang B, Chernoff J, Zheng Y. Interaction of Rac1 with GTPase-activating proteins and putative effectors. A comparison with Cdc42 and RhoA. *J Biol Chem* 1998 Apr. 10; 273: 8776-8782.

Yu J, Chen L, Cui B, Widhopf G F, 2nd, Shen Z, Wu R, et al. Wnt5a induces ROR-1/ROR2 heterooligomerization to enhance leukemia chemotaxis and proliferation. *J Clin Invest* 2015 Dec. 21.

Fecteau J F, Corral L G, Ghia E M, Gaidarova S, Futalan D, Bharati I S, et al. Lenalidomide inhibits the proliferation of CLL cells via a cereblon/p21(WAF1/Cip1)-dependent mechanism independent of functional p53. *Blood* 2014 Sep. 4; 124: 1637-1644.

Yuan Y, Shen H, Franklin D S, Scadden D T, Cheng T. In vivo self-renewing divisions of haematopoietic stem cells are increased in the absence of the early G1-phase inhibitor, p18INK4C. *Nat Cell Biol* 2004 May; 6: 436-442.

Shen H, Yu H, Liang P H, Cheng H, XuFeng R, Yuan Y, et al. An acute negative bystander effect of gamma-irradiated recipients on transplanted hematopoietic stem cells. *Blood* 2012 Apr. 12; 119: 3629-3637.

Castillo R, Mascarenhas J, Telford W, Chadburn A, Friedman S M, Schattner E J. Proliferative response of mantle cell lymphoma cells stimulated by CD40 ligation and IL-4. *Leukemia* 2000 February; 14(2): 292-298.

Visser H P, Tewis M, Willemze R, Kluin-Nelemans J C. Mantle cell lymphoma proliferates upon IL-10 in the CD40 system. *Leukemia* 2000 August; 14(8): 1483-1489.

Byrd J C, Furman R R, Coutre S E, Flinn I W, Burger J A, Blum K A, et al. Targeting BTK with ibrutinib in relapsed chronic lymphocytic leukemia. *N Engl J Med* 2013 Jul. 4; 369(1): 32-42.

de Rooij M F, Kuil A, Geest C R, Eldering E, Chang B Y, Buggy J J, et al. The clinically active BTK inhibitor PCI-32765 targets B-cell receptor- and chemokine-controlled adhesion and migration in chronic lymphocytic leukemia. *Blood* 2012 Mar. 15; 119(11): 2590-2594.

Chang B Y, Francesco M, De Rooij M F, Magadala P, Steggerda S M, Huang M M, et al. Egress of CD19(+) CD5(+) cells into peripheral blood following treatment with the Bruton tyrosine kinase inhibitor ibrutinib in mantle cell lymphoma patients. *Blood* 2013 Oct. 3; 122 (14): 2412-2424.

Spaargaren M, de Rooij M F, Kater A P, Eldering E. BTK inhibitors in chronic lymphocytic leukemia: a glimpse to the future. *Oncogene* 2015 May 7; 34(19): 2426-2436.

Wang M L, Rule S, Martin P, Goy A, Auer R, Kahl B S, et al. Targeting BTK with ibrutinib in relapsed or refractory mantle-cell lymphoma. *N Engl J Med* 2013 Aug. 8; 369(6): 507-516.

Woyach J A, Furman R R, Liu T M, Ozer H G, Zapatka M, Ruppert A S, et al. Resistance mechanisms for the Bruton's tyrosine kinase inhibitor ibrutinib. *N Engl J Med* 2014 Jun. 12; 370(24): 2286-2294.

Byrd J C, Brown J R, O'Brien S, Barrientos J C, Kay N E, Reddy N M, et al. Ibrutinib versus ofatumumab in previously treated chronic lymphoid leukemia. *N Engl J Med* 2014 Jul. 17; 371(3): 213-223.

Fukuda T, Chen L, Endo T, Tang L, Lu D, Castro J E, et al. Antisera induced by infusions of autologous Ad-CD154-leukemia B cells identify ROR-1 as an oncofetal antigen and receptor for Wnt5a. *Proc Natl Acad Sci USA* 2008 Feb. 26; 105(8): 3047-3052.

Hofbauer S W, Krenn P W, Ganghammer S, Asslaber D, Pichler U, Oberascher K, et al. Tiam1/Rac1 signals contribute to the proliferation and chemoresistance, but not motility, of chronic lymphocytic leukemia cells. *Blood* 2014 Apr. 3; 123(14): 2181-2188.

Kaucka M, Plevova K, Pavlova S, Janovska P, Mishra A, Verner J, et al. The planar cell polarity pathway drives pathogenesis of chronic lymphocytic leukemia by the regulation of B-lymphocyte migration. *Cancer Res* 2013 Mar. 1; 73(5): 1491-1501.

Yu J, Chen L, Cui B, Widhopf G F, 2nd, Shen Z, Wu R, et al. Wnt5a induces ROR-1/ROR2 heterooligomerization to enhance leukemia chemotaxis and proliferation. *J Clin Invest* 2015 Dec. 21.

Yu J, Chen L, Cui B, Wu C, Choi M Y, Chen Y, et al. Cirmtuzumab inhibits Wnt5a-induced Rac1 activation in chronic lymphocytic leukemia treated with ibrutinib. *Leukemia* 2017 Jan. 3.

Krishan A. Rapid flow cytofluorometric analysis of mammalian cell cycle by propidium iodide staining. *J Cell Biol* 1975 July; 66(1): 188-193.

```
INFORMAL SEQUENCE LISTING
99961.1 CDR H1 (SEQ ID NO: 1): GYAFTAYN 99961.1 CDR H2 (SEQ ID NO: 2): FDPYDGGS 99961.1 CDR H3 (SEQ ID NO: 3):GWYYFDY 99961.1 CDR L1 (SEQ ID NO: 4): KSISKY 99961.1 CDR L2 (SEQ ID NO: 5): SGS 99961.1 CDR L3 (SEQ ID NO: 6): QQHDESPY

D10 CDR H1 (SEQ ID NO: 7): GFSLTSYG

D10 CDR H2 (SEQ ID NO: 8): IWAGGFT

D10 CDR H3 (SEQ ID NO: 9): RGSSYSMDY

D10 CDR L1 (SEQ ID NO: 10): SNVSY

D10 CDR L2 (SEQ ID NO: 11): EIS

D10 CDR L3 (SEQ ID NO: 12): QQWNYPLIT

Full-length human ROR-1 Protein (SEQ ID NO: 13):
MEIRPRRRGTRPPLLALLAALLLAARGAAAQETELSVSAELVPTSSWNISS

ELNKDSYLTLDEPMNNITTSLGQTAELHCKVSGNPPPTIRWFKNDAPVVQE

PRRLSFRSTIYGSRLRIRNLDTTDTGYFQCVATNGKEVVSSTGVLFVKFGP

PPTASPGYSDEYEEDGFCQPYRGIACARFIGNRTVYMESLHMQGEIENQIT

AAFTMIGTSSHLSDKCSQFAIPSLCHYAFPYCDETSSVPKPRDLCRDECEI

LENVLCQTEYIFARSNPMILMRLKLPNCEDLPQPESPEAANCIRIGIPMAD

PINKNHKCYNSTGVDYRGTVSVTKSGRQCQPWNSQYPHTHTFTALRFPELN

GGHSYCRNPGNQKEAPWCFTLDENFKSDLCDIPACDSKDSKEKNKMEILYI

LVPSVAIPLAIALLFFFICVCRNNQKSSSAPVQRQPKHVRGQNVEMSMLNA

YKPKSKAKELPLSAVRFMEELGECAFGKIYKGHLYLPGMDHAQLVAIKTLK

DYNNPQQWMEFQQEASLMAELHHPNIVCLLGAVTQEQPVCMLFEYINQGDL

HEFLIMRSPHSDVGCSSDEDGTVKSSLDHGDFLHIAIQIAAGMEYLSSHFF

VHKDLAARNILIGEQLHVKISDLGLSREIYSADYYRVQSKSLLPIRWMPPE

AIMYGKFSSDSDIWSFGVVLWEIFSFGLQPYYGFSNQEVIEMVRKRQLLPC

SEDCPPRMYSLMTECWNEIPSRRPRFKDIHVRLRSWEGLSSHTSSTTPSGG

NATTQTTSLSASPVSNLSNPRYPNYMFPSQGITPQGQIAGFIGPPIPQNQR

FIPINGYPIPPGYAAFPAAHYQPTGPPRVIQHCPPPKSRSPSSASGSTSTG

HVTSLPSSGSNQEANIPLLPHMSIPNHPGGMGITVFGNKSQKPYKIDSKQA

SLLGDANIEGHTESMISAEL 21 amino acid stretch of human ROR-1 including
glutamic acid at position 138 (SEQ ID NO: 14):
VATNGKEVVSSTGVLFVKFGP 15 amino acid stretch of human ROR-1 including
glutamic acid at position 138 (SEQ ID NO. 15):
EVVSSTGVLFVKFGP
```

P Embodiments

Embodiment P1. A method of treating cancer in a subject in need thereof, said method comprising administering to said subject a therapeutically effective amount of a Bruton's tyrosine kinase (BTK) antagonist and an anti-ROR-1 antibody.

Embodiment P2. The method according to embodiment P1, wherein said BTK antagonist is CAL101, R406 or Ibrutinib.

Embodiment P3. The method according to one of embodiments P1-P2, wherein said BTK antagonist is Ibrutinib.

Embodiment P4. The method according to one of embodiments P1-P3, wherein said anti-ROR-1 antibody is cirmtuzumab.

Embodiment P5. The method according to one of embodiments P1-P4, wherein said BTK antagonist and anti-ROR-1 antibody are administered in a combined synergistic amount.

Embodiment P6. The method according to one of embodiments P1-P5, wherein said BTK antagonist and anti-ROR-1 antibody are administered simultaneously or sequentially.

Embodiment P7. The method according to one of embodiments P1-P6, wherein said cancer is a lymphoma or an adenocarcinoma.

Embodiment P8. The method according to one of embodiments P1-P7, wherein said lymphoma is chronic lymphocytic leukemia, small lymphocytic lymphoma, marginal cell B-cell lymphoma, or Burkitt's lymphoma.

Embodiment P9. The method according to one of embodiments P1-P8, wherein said adenocarcinoma is colon adenocarcinoma or breast adenocarcinoma.

Embodiment P10. A pharmaceutical composition comprising a Bruton's tyrosine kinase (BTK) antagonist, an anti-ROR-1 antibody and a pharmaceutically acceptable excipient, wherein said BTK antagonist and said anti-ROR-1 antibody are present in a combined synergistic amount, wherein said combined synergistic amount is effective to treat cancer in a subject in need thereof.

Embodiments

Embodiment 1. A method of treating cancer in a subject in need thereof, said method comprising administering to said subject a therapeutically effective amount of a Bruton's tyrosine kinase (BTK) antagonist and a tyrosine kinase-like orphan receptor 1 (ROR-1) antagonist.

Embodiment 2. The method of embodiment 1, wherein said BTK antagonist is a small molecule.

Embodiment 3. The method of embodiment 1 or 2, wherein said BTK antagonist is ibrutinib, idelalisib, fostamatinib, acalabrutinib, ONO/GS-4059, BGB-3111 or CC-292 (AVL-292).

Embodiment 4. The method of one of embodiments 1-3, wherein said BTK antagonist is ibrutinib.

Embodiment 5. The method of one of embodiments 1-4, wherein said ROR-1 antagonist is an antibody or a small molecule.

Embodiment 6. The method of one of embodiments 1-5, wherein said ROR-1 antagonist is an anti-ROR-1 antibody.

Embodiment 7. The method of one of embodiments 5-6, wherein said antibody comprises a humanized heavy chain variable region and a humanized light chain variable region, wherein said humanized heavy chain variable region comprises the sequences set forth in SEQ ID NO:1, SEQ ID NO:2, and SEQ ID NO:3; and wherein said humanized light chain variable region comprises the sequences set forth in SEQ ID NO:4, SEQ ID NO:5, and SEQ ID NO:6.

Embodiment 8. The method of one of embodiments 3-7, wherein said antibody is cirmtuzumab.

Embodiment 9. The method of one of embodiments 5-6, wherein said antibody comprises a humanized heavy chain variable region and a humanized light chain variable region, wherein said humanized heavy chain variable region comprises the sequences set forth in SEQ ID NO:7, SEQ ID NO:8, and SEQ ID NO:9; and wherein said humanized light chain variable region comprises the sequences set forth in SEQ ID NO:10, SEQ ID NO:11, and SEQ ID NO:12.

Embodiment 10. The method of one of embodiments 1-9, wherein said BTK antagonist and said ROR-1 antagonist are administered in a combined synergistic amount.

Embodiment 11. The method of one of embodiments 1-10, wherein said BTK antagonist and said ROR-1 antagonist are administered simultaneously or sequentially.

Embodiment 12. The method of one of embodiments 1-11, wherein said ROR-1 antagonist is administered at a first time point and said BTK antagonist is administered at a second time point, wherein said first time point precedes said second time point.

Embodiment 13. The method of one of embodiments 1-12, wherein said BTK antagonist and said ROR-1 antagonist are admixed prior to administration.

Embodiment 14. The method of one of embodiments 1-13, wherein said BTK antagonist is administered at an amount of about 1 mg/kg, 2 mg/kg, 5 mg/kg, 15 mg/kg or 10 mg/kg.

Embodiment 15. The method of one of embodiments 1-14, wherein said BTK antagonist is administered at an amount of about 5 mg/kg.

Embodiment 16. The method of one of embodiments 1-14, wherein said BTK antagonist is administered at an amount of about 420 mg.

Embodiment 17. The method of one of embodiments 1-16, wherein said ROR-1 antagonist is administered at an amount of about 1 mg/kg, 2 mg/kg, 3 mg/kg, 5 mg/kg or 10 mg/kg.

Embodiment 18. The method of one of embodiments 1-17, wherein said ROR-1 antagonist is administered at an amount of about 2 mg/kg.

Embodiment 19. The method of one of embodiments 1-15 or 17-18, wherein said BTK antagonist is administered at an amount of about 5 mg/kg and said ROR-1 antagonist is administered at about 2 mg/kg.

Embodiment 20. The method of one of embodiments 1-15 or 17, wherein said BTK antagonist is administered at an amount of about 5 mg/kg and said ROR-1 antagonist is administered at about 1 mg/kg.

Embodiment 21. The method of one of embodiments 1-20, wherein said BTK antagonist is administered daily over the course of at least 14 days.

Embodiment 22. The method of one of embodiments 1-21, wherein said BTK antagonist is administered daily over the course of about 28 days.

Embodiment 23. The method of one of embodiments 1-22, wherein said ROR-1 antagonist is administered once over the course of about 28 days.

Embodiment 24. The method of one of embodiments 1-23, wherein said BTK antagonist is administered intravenously.

Embodiment 25. The method of one of embodiments 1-24, wherein said ROR-1 antagonist is administered intravenously.

Embodiment 26. The method of one of embodiments 1-25, wherein said subject is a mammal.

Embodiment 27. The method of one of embodiments 1-26, wherein said subject is a human.

Embodiment 28. The method of one of embodiments 1-27, wherein said cancer is lymphoma, leukemia, myeloma, AML, B-ALL, T-ALL, renal cell carcinoma, colon cancer, colorectal cancer, breast cancer, epithelial squamous cell cancer, melanoma, stomach cancer, brain cancer, lung cancer, pancreatic cancer, cervical cancer, ovarian cancer, liver cancer, bladder cancer, prostate cancer, testicular cancer, thyroid cancer, head and neck cancer, uterine cancer, adenocarcinoma, or adrenal cancer.

Embodiment 29. The method of one of embodiments 1-28, wherein said cancer is chronic lymphocytic leukemia (CLL), small lymphocytic lymphoma, marginal cell B-Cell lymphoma, Burkitt's Lymphoma, or B cell leukemia.

Embodiment 30. A pharmaceutical composition comprising a BTK antagonist, a ROR-1 antagonist and a pharmaceutically acceptable excipient.

Embodiment 31. A pharmaceutical composition comprising a BTK antagonist, an anti-ROR-1 antibody and a pharmaceutically acceptable excipient, wherein said BTK antagonist and said anti-ROR-1 antibody are present in a combined synergistic amount, wherein said combined synergistic amount is effective to treat cancer in a subject in need thereof.

Embodiment 32. The pharmaceutical composition of embodiment 30 or 31, wherein said BTK antagonist is a small molecule.

Embodiment 33. The pharmaceutical composition of one of embodiments 30-32, wherein said BTK antagonist is ibrutinib, idelalisib, fostamatinib, acalabrutinib, ONO/GS-4059, BGB-3111 or CC-292 (AVL-292).

Embodiment 34. The pharmaceutical composition of one of embodiments 30-33, wherein said BTK antagonist is ibrutinib.

Embodiment 35. The pharmaceutical composition of one of embodiments 30-34, wherein said ROR-1 antagonist is an antibody or a small molecule.

Embodiment 36. The pharmaceutical composition of one of embodiments 30-35, wherein said ROR-1 antagonist is an anti-ROR-1 antibody.

Embodiment 37. The pharmaceutical composition of embodiment 35 or 36, wherein said antibody comprises a humanized heavy chain variable region and a humanized light chain variable region, wherein said humanized heavy chain variable region comprises the sequences set forth in SEQ ID NO:1, SEQ ID NO:2, and SEQ ID NO:3; and wherein said humanized light chain variable region comprises the sequences set forth in SEQ ID NO:4, SEQ ID NO:5, and SEQ ID NO:6.

Embodiment 38. The pharmaceutical composition of one of embodiments 35-37, wherein said antibody is cirmtuzumab.

Embodiment 39. The pharmaceutical composition of embodiment 35 or 36, wherein said antibody comprises a humanized heavy chain variable region and a humanized light chain variable region, wherein said humanized heavy chain variable region comprises the sequences set forth in SEQ ID NO:7, SEQ ID NO:8, and SEQ ID NO:9; and wherein said humanized light chain variable region comprises the sequences set forth in SEQ ID NO:10, SEQ ID NO:11, and SEQ ID NO:12.

What is claimed is:

1. A method of treating an ROR-1 expressing cancer or a cancer susceptible to a BTK antagonist in a subject in need thereof, said method comprising administering to said subject a therapeutically effective amount of an inhibitor of B-cell receptor (BCR) signaling and a tyrosine kinase-like orphan receptor 1 (ROR-1) antagonist, wherein said ROR-1 antagonist is an antibody comprising a heavy chain variable region and a light chain variable region, wherein said heavy chain variable region comprises the sequences set forth in SEQ ID NO: 1, SEQ ID NO:2, and SEQ ID NO:3; and wherein said light chain variable region comprises the sequences set forth in SEQ ID NO:4, SEQ ID NO:5, and SEQ ID NO:6.

2. The method of claim 1, wherein said inhibitor of BCR signaling is a small molecule.

3. The method of claim 1, wherein said inhibitor of BCR signaling is ibrutinib, idelalisib, fostamatinib, acalabrutinib, ONO/GS-4059, BGB-3111, or CC-292 (AVL-292).

4. The method of claim 1, wherein said antibody is cirmtuzumab.

5. The method of claim 1, wherein said subject is a human.

6. The method of claim 1, wherein said ROR-1 expressing cancer or said cancer susceptible to a BTK antagonist is lymphoma, leukemia, myeloma, AML, B-ALL, T-ALL, renal cell carcinoma, colon cancer, colorectal cancer, breast cancer, epithelial squamous cell cancer, melanoma, stomach cancer, brain cancer, lung cancer, pancreatic cancer, cervical cancer, ovarian cancer, liver cancer, bladder cancer, prostate cancer, testicular cancer, thyroid cancer, head and neck cancer, uterine cancer, adenocarcinoma, or adrenal cancer.

7. The method of claim 1, wherein said ROR-1 expressing cancer or said cancer susceptible to a BTK antagonist is chronic lymphocytic leukemia (CLL), small lymphocytic lymphoma, mantle cell lymphoma (MCL), marginal cell B-Cell lymphoma, Burkitt's Lymphoma, or B cell leukemia.

8. A method of treating an ROR-1 expressing cancer or a cancer susceptible to a BTK antagonist in a subject in need thereof, said method comprising administering to said subject a therapeutically effective amount of a Bruton's tyrosine kinase inhibitor (BTK) antagonist and a tyrosine kinase-like orphan receptor 1 (ROR-1) antagonist, wherein said ROR-1 antagonist is an antibody that specifically binds to ROR-1.

9. The method of claim 8, wherein said BTK antagonist is a small molecule.

10. The method of claim 8, wherein said BTK antagonist is ibrutinib, acalabrutinib, ONO/GS-4059, BGB-3111 or CC-292 (AVL-292).

11. The method of claim 8, wherein said subject is a human.

12. The method of claim 8, wherein said cancer is lymphoma, leukemia, myeloma, AML, B-ALL, T-ALL, renal cell carcinoma, colon cancer, colorectal cancer, breast cancer, epithelial squamous cell cancer, melanoma, stomach cancer, brain cancer, lung cancer, pancreatic cancer, cervical cancer, ovarian cancer, liver cancer, bladder cancer, prostate cancer, testicular cancer, thyroid cancer, head and neck cancer, uterine cancer, adenocarcinoma, or adrenal cancer.

13. The method of claim 8, wherein said cancer is chronic lymphocytic leukemia (CLL), small lymphocytic lymphoma, mantle cell lymphoma (MCL), marginal cell B-Cell lymphoma, Burkitt's Lymphoma, or B cell leukemia.

* * * * *

```
                        SEQUENCE LISTING

<160> NUMBER OF SEQ ID NOS: 15

<210> SEQ ID NO 1
    <211> LENGTH: 8
    <212> TYPE: PRT
    <213> ORGANISM: Artificial Sequence
    <220> FEATURE:
    <223> OTHER INFORMATION: Synthetic polypeptide

<400> SEQUENCE: 1

Gly Tyr Ala Phe Thr Ala Tyr Asn
    1               5

<210> SEQ ID NO 2
    <211> LENGTH: 8
    <212> TYPE: PRT
    <213> ORGANISM: Artificial Sequence
    <220> FEATURE:
    <223> OTHER INFORMATION: Synthetic polypeptide

<400> SEQUENCE: 2

Phe Asp Pro Tyr Asp Gly Gly Ser
    1               5

<210> SEQ ID NO 3
    <211> LENGTH: 7
    <212> TYPE: PRT
    <213> ORGANISM: Artificial Sequence
    <220> FEATURE:
    <223> OTHER INFORMATION: Synthetic polypeptide

<400> SEQUENCE: 3

Gly Trp Tyr Tyr Phe Asp Tyr
    1               5

<210> SEQ ID NO 4
```

```
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 4

Lys Ser Ile Ser Lys Tyr
1               5

<210> SEQ ID NO 5
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 5

Ser Gly Ser
1

<210> SEQ ID NO 6
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 6

Gln Gln His Asp Glu Ser Pro Tyr
1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 7

Gly Phe Ser Leu Thr Ser Tyr Gly
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 8

Ile Trp Ala Gly Gly Phe Thr
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 9

Arg Gly Ser Ser Tyr Ser Met Asp Tyr
1               5

<210> SEQ ID NO 10
<211> LENGTH: 5
```

```
<212> TYPE: PRT
<213> ORGANISM: Artificial Sequence
<220> FEATURE:
<223> OTHER INFORMATION: Synthetic polypeptide

<400> SEQUENCE: 10

Ser Asn Val Ser Tyr
1               5

<210> SEQ ID NO 11
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 11

Glu Ile Ser
1

<210> SEQ ID NO 12
<211> LENGTH: 9
<212> TYPE: PRT
<213> ORGANISM: Artificial  Sequence
<220> FEATURE:
<223> OTHER INFORMATION: Synthetic polypeptide

<400> SEQUENCE: 12

Gln Gln Trp Asn Tyr Pro Leu Ile Thr
1               5

<210> SEQ ID NO 13
<211> LENGTH: 937
<212> TYPE: PRT
<213> ORGANISM: Homo sapiens

<400> SEQUENCE: 13

Met His Arg Pro Arg Arg Arg Gly Thr Arg Pro Pro Leu Leu Ala Leu
1               5                   10                  15

Leu Ala Ala Leu Leu Leu Ala Ala Arg Gly Ala Ala Ala Gln Glu Thr
                20                  25                  30

Glu Leu Ser Val Ser Ala Glu Leu Val Pro Thr Ser Ser Trp Asn Ile
            35                  40                  45

Ser Ser Glu Leu Asn Lys Asp Ser Tyr Leu Thr Leu Asp Glu Pro Met
        50                  55                  60

Asn Asn Ile Thr Thr Ser Leu Gly Gln Thr Ala Glu Leu His Cys Lys
65                  70                  75                  80

Val Ser Gly Asn Pro Pro Pro Thr Ile Arg Trp Phe Lys Asn Asp Ala
                85                  90                  95

Pro Val Val Gln Glu Pro Arg Arg Leu Ser Phe Arg Ser Thr Ile Tyr
            100                 105                 110

Gly Ser Arg Leu Arg Ile Arg Asn Leu Asp Thr Thr Asp Thr Gly Tyr
        115                 120                 125

Phe Gln Cys Val Ala Thr Asn Gly Lys Glu Val Val Ser Ser Thr Gly
    130                 135                 140

Val Leu Phe Val Lys Phe Gly Pro Pro Thr Ala Ser Pro Gly Tyr
145                 150                 155                 160

Ser Asp Glu Tyr Glu Glu Asp Gly Phe Cys Gln Pro Tyr Arg Gly Ile
                165                 170                 175

Ala Cys Ala Arg Phe Ile Gly Asn Arg Thr Val Tyr Met Glu Ser Leu
            180                 185                 190
```

-continued

His Met Gln Gly Glu Ile Glu Asn Gln Ile Thr Ala Ala Phe Thr Met
            195                 200                 205

Ile Gly Thr Ser Ser His Leu Ser Asp Lys Cys Ser Gln Phe Ala Ile
        210                 215                 220

Pro Ser Leu Cys His Tyr Ala Phe Pro Tyr Cys Asp Glu Thr Ser Ser
225                 230                 235                 240

Val Pro Lys Pro Arg Asp Leu Cys Arg Asp Glu Cys Glu Ile Leu Glu
                245                 250                 255

Asn Val Leu Cys Gln Thr Glu Tyr Ile Phe Ala Arg Ser Asn Pro Met
                260                 265                 270

Ile Leu Met Arg Leu Lys Leu Pro Asn Cys Glu Asp Leu Pro Gln Pro
            275                 280                 285

Glu Ser Pro Glu Ala Ala Asn Cys Ile Arg Ile Gly Ile Pro Met Ala
        290                 295                 300

Asp Pro Ile Asn Lys Asn His Lys Cys Tyr Asn Ser Thr Gly Val Asp
305                 310                 315                 320

Tyr Arg Gly Thr Val Ser Val Thr Lys Ser Gly Arg Gln Cys Gln Pro
                325                 330                 335

Trp Asn Ser Gln Tyr Pro His Thr His Thr Phe Thr Ala Leu Arg Phe
                340                 345                 350

Pro Glu Leu Asn Gly Gly His Ser Tyr Cys Arg Asn Pro Gly Asn Gln
            355                 360                 365

Lys Glu Ala Pro Trp Cys Phe Thr Leu Asp Glu Asn Phe Lys Ser Asp
        370                 375                 380

Leu Cys Asp Ile Pro Ala Cys Asp Ser Lys Asp Ser Lys Glu Lys Asn
385                 390                 395                 400

Lys Met Glu Ile Leu Tyr Ile Leu Val Pro Ser Val Ala Ile Pro Leu
                405                 410                 415

Ala Ile Ala Leu Leu Phe Phe Phe Ile Cys Val Cys Arg Asn Asn Gln
            420                 425                 430

Lys Ser Ser Ser Ala Pro Val Gln Arg Gln Pro Lys His Val Arg Gly
        435                 440                 445

Gln Asn Val Glu Met Ser Met Leu Asn Ala Tyr Lys Pro Lys Ser Lys
    450                 455                 460

Ala Lys Glu Leu Pro Leu Ser Ala Val Arg Phe Met Glu Glu Leu Gly
465                 470                 475                 480

Glu Cys Ala Phe Gly Lys Ile Tyr Lys Gly His Leu Tyr Leu Pro Gly
                485                 490                 495

Met Asp His Ala Gln Leu Val Ala Ile Lys Thr Leu Lys Asp Tyr Asn
            500                 505                 510

Asn Pro Gln Gln Trp Met Glu Phe Gln Gln Glu Ala Ser Leu Met Ala
        515                 520                 525

Glu Leu His His Pro Asn Ile Val Cys Leu Leu Gly Ala Val Thr Gln
    530                 535                 540

Glu Gln Pro Val Cys Met Leu Phe Glu Tyr Ile Asn Gln Gly Asp Leu
545                 550                 555                 560

His Glu Phe Leu Ile Met Arg Ser Pro His Ser Asp Val Gly Cys Ser
                565                 570                 575

Ser Asp Glu Asp Gly Thr Val Lys Ser Ser Leu Asp His Gly Asp Phe
            580                 585                 590

Leu His Ile Ala Ile Gln Ile Ala Ala Gly Met Glu Tyr Leu Ser Ser
        595                 600                 605

```
His Phe Phe Val His Lys Asp Leu Ala Ala Arg Asn Ile Leu Ile Gly
610                 615                 620

Glu Gln Leu His Val Lys Ile Ser Asp Leu Gly Leu Ser Arg Glu Ile
625                 630                 635                 640

Tyr Ser Ala Asp Tyr Tyr Arg Val Gln Ser Lys Ser Leu Leu Pro Ile
            645                 650                 655

Arg Trp Met Pro Pro Glu Ala Ile Met Tyr Gly Lys Phe Ser Ser Asp
            660                 665                 670

Ser Asp Ile Trp Ser Phe Gly Val Val Leu Trp Glu Ile Phe Ser Phe
        675                 680                 685

Gly Leu Gln Pro Tyr Tyr Gly Phe Ser Asn Gln Glu Val Ile Glu Met
690                 695                 700

Val Arg Lys Arg Gln Leu Leu Pro Cys Ser Glu Asp Cys Pro Pro Arg
705                 710                 715                 720

Met Tyr Ser Leu Met Thr Glu Cys Trp Asn Glu Ile Pro Ser Arg Arg
                725                 730                 735

Pro Arg Phe Lys Asp Ile His Val Arg Leu Arg Ser Trp Glu Gly Leu
            740                 745                 750

Ser Ser His Thr Ser Ser Thr Thr Pro Ser Gly Gly Asn Ala Thr Thr
        755                 760                 765

Gln Thr Thr Ser Leu Ser Ala Ser Pro Val Ser Asn Leu Ser Asn Pro
770                 775                 780

Arg Tyr Pro Asn Tyr Met Phe Pro Ser Gln Gly Ile Thr Pro Gln Gly
785                 790                 795                 800

Gln Ile Ala Gly Phe Ile Gly Pro Pro Ile Pro Gln Asn Gln Arg Phe
                805                 810                 815

Ile Pro Ile Asn Gly Tyr Pro Ile Pro Pro Gly Tyr Ala Ala Phe Pro
            820                 825                 830

Ala Ala His Tyr Gln Pro Thr Gly Pro Pro Arg Val Ile Gln His Cys
        835                 840                 845

Pro Pro Pro Lys Ser Arg Ser Pro Ser Ser Ala Ser Gly Ser Thr Ser
850                 855                 860

Thr Gly His Val Thr Ser Leu Pro Ser Ser Gly Ser Asn Gln Glu Ala
865                 870                 875                 880

Asn Ile Pro Leu Leu Pro His Met Ser Ile Pro Asn His Pro Gly Gly
                885                 890                 895

Met Gly Ile Thr Val Phe Gly Asn Lys Ser Gln Lys Pro Tyr Lys Ile
            900                 905                 910

Asp Ser Lys Gln Ala Ser Leu Leu Gly Asp Ala Asn Ile His Gly His
        915                 920                 925

Thr Glu Ser Met Ile Ser Ala Glu Leu
930                 935
```

<210> SEQ ID NO 14
<211> LENGTH: 21
<212> TYPE: PRT
<213> ORGANISM: Homo sapiens

<400> SEQUENCE: 14

```
Val Ala Thr Asn Gly Lys Glu Val Ser Ser Thr Gly Val Leu Phe
1               5                   10                  15

Val Lys Phe Gly Pro
            20
```

<210> SEQ ID NO 15

```
<211> LENGTH: 15
<212> TYPE: PRT
<213> ORGANISM: Homo sapiens

<400> SEQUENCE: 15

Glu Val Val Ser Ser Thr Gly Val Leu Phe Val Lys Phe Gly Pro
1               5                   10                  15
```